US010827703B2

(12) United States Patent
Moehs et al.

(10) Patent No.: US 10,827,703 B2
(45) Date of Patent: *Nov. 10, 2020

(54) REDUCED GLUTEN GRAINS AND COMPOSITIONS THEREOF

(71) Applicant: Arcadia Biosciences, Inc., Davis, CA (US)

(72) Inventors: Charles Paul Moehs, Seattle, WA (US); William J. Austill, Seattle, WA (US); Dayna Loeffler, Seattle, WA (US); Jessica Mullenberg, Seattle, WA (US)

(73) Assignee: ARCADIA BIOSCIENCES, INC., Davis, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/564,636

(22) Filed: Sep. 9, 2019

(65) Prior Publication Data

US 2020/0000053 A1    Jan. 2, 2020

Related U.S. Application Data

(63) Continuation of application No. 15/994,601, filed on May 31, 2018, now Pat. No. 10,412,909, which is a continuation of application No. 15/577,588, filed as application No. PCT/US2016/035057 on May 31, 2016.

(60) Provisional application No. 62/327,822, filed on Apr. 26, 2016, provisional application No. 62/168,536, filed on May 29, 2015, provisional application No. 62/263,912, filed on Dec. 7, 2015.

(51) Int. Cl.
    *A01H 6/46*      (2018.01)
    *A01H 5/10*      (2018.01)
    *C12N 15/00*     (2006.01)

(52) U.S. Cl.
    CPC ............. *A01H 6/4678* (2018.05); *A01H 5/10* (2013.01)

(58) Field of Classification Search
    None
    See application file for complete search history.

(56) References Cited

U.S. PATENT DOCUMENTS

| 10,412,909 B2 * | 9/2019 | Moehs | A01H 1/06 |
| 2019/0000025 A1 * | 1/2019 | Moehs | A01H 5/10 |

FOREIGN PATENT DOCUMENTS

| WO | 2004/048406 A1 | 6/2004 |
| WO | 2013097940 A1 | 7/2013 |

OTHER PUBLICATIONS

Moehs et al, 2019, Plant Physiology, 179:1692-1703.*
Gil-Humanes et al, 2008, Journal of Cereal Science, 48:565-568.*
Rajendran et al, 2015, OMICS: A Journal of Integrative Biology, 19:261-275.*
Mitea et al, 2010, PLoS, 5:1-9.*
Dong et al, 2007, Plant Mol. Biol., 63:73-84.*
Non-Final Office Action for U.S. Appl. No. 15/577,588 dated Oct. 16, 2019; 13 pages.
Gil-Humanes, Javier, et al. "Reduced-gliadin wheat bread: an alternative to the gluten-free diet for consumers suffering gluten-related pathologies," PloS one 9.3 (2014): e90898. (Year: 2014).
Rajendran, Subin Raj Cheri Kunnumal, et al. "CRISPR-Cas9 based genome engineering: opportunities in agri-food-nutrition and healthcare." Omics: a journal of integrative biology 19.5 (2015): 261-275. (Year: 2015).
Dong, Guoqing, et al. "Wheat Dof transcription factor WPBF interacts with TaQM and activates transcription of an alpha-gliadin gene during wheat seed development." Plant Molecular Biology 63.1 (2007): 73-84. (Year: 2007).
Colomba et al, 2012, The Scientific World Journal, Article ID 837416:1-8.
International Search Report and Written Opinion for International Appln. No. PCT/US2016/035057, dated Nov. 4, 2016, 11 pages.
Kai Wang et al., Gene 527 (2013) 484-490.
Szaboles Makai et al., Funct Intergr Genomics (2015) 15:661-672.
Maoyun She et al., Funct Integr Genomics (2011) 11:23-35.
Yong-Sic Hwang et al., Plant Cell Physiol. 45(10): 1509-1518 (2004).
Montana Mena et al., The Plant Journal (1998) 16(1), 53-62.
Ravel, Catherine, et al. "Single nucleotide polymorphism, genetic mapping, and expression of genes coding for the DOF wheat prolamin-box binding factor." Functional & integrative genomics 6.4 (2006): 310-321. (Year: 2006).
Gil-Humanes, Javier, et al. "Silencing of y-gliadins by RNA interference (RNAi) in bread wheat." Journal of Cereal Science 48.3 (2008): 565-568 (Year: 2008).

* cited by examiner

*Primary Examiner* — Jason Deveau Rosen
(74) *Attorney, Agent, or Firm* — Hiusch Blackell LLP

(57) ABSTRACT

Plants with reduced gluten grains and compositions thereof are disclosed herein.

15 Claims, 6 Drawing Sheets

Specification includes a Sequence Listing.

SEQUENCE LISTING

```
<160> NUMBER OF SEQ ID NOS: 13

<210> SEQ ID NO 1
<211> LENGTH: 2024
<212> TYPE: DNA
<213> ORGANISM: Triticum aestivum

<400> SEQUENCE: 1
ctggcttgct cattttgcgg tagtgtttaa acatcggcta gccttacggg tataaaaagg      60
tgggcaactt caccctatcc catagcacta gaccaaagaa cacctatact ccatactacc     120
cttcgttcac ctggtgagct tcttcttcct ttgatctata tcacttacta tttctccctt     180
gtccagcttc ttcttcttcc tcgtgcatgc gacttttcct agataatatc ccgcactatc     240
gctcgccgca agatgtgcta gctagcgatc ttcactttaa tacctgttgt agatctaacc     300
acgggctatt ccaaaaaata tttgtcttgt ttgcgtgttc ctgtgtacat gcacgtatct     360
agatcttgat tttgaagaat tcataattaa ttcatgacct accttgtttg gtttgtgtaa     420
ttttgatgtt gtcgtatcaa ttttagcaaa ccactcgtag ctagaacaat agaggggggcg     480 atcgtatgtt tctgttttga aaagggggata tttccaggct ctgcatcggt tcatgcacac     540
agccgttacc acattcaata ggcactgatc catggatgca tgccagattt actagttttg     600
tatacaaagt tttactttt tgctttgatt tatgaaaagt tggatcagat tttgcagttc     660
tcttttatcc atgttggatt cactactttg tacccaagat tttatttatt ttgtcttggt     720
ttcttacctg cctggttagt aactaggaga tcctgggatt agactttcaa ggaatcctaa     780
tactagtgag tatagggaaa ggaagcttat tttaagctg cccaaaagaa tgggcgctta      840
gagttgtagt tgattaattg aatctgttct gtggatttga gaatttcaga cctgattcta     900
catgacattt tgagttaacc aatgattcta catgtctcac tccttgggat taacaattta     960
actttattta attcgatatg tgtgtacaca tgtgttgcag atggaggaag tgtttccgtc    1020
```

```
aaactccaag agcaaggccg gtcagatggc gggggaggcg acagcggcgg cggagaagaa    1080
gcctcggccg aagccagagc agaaggtgga atgccctcgg tgcaagtctg caacaccaa    1140 gttctgctac tacaacaact atagtatgtc tcagccccgc tacttctgca aggcctgccg    1200
ccgctactgg acccatggtg ctccctccg caacgtcccc atcggtggcg ctgccgcaa      1260 gcccaagcgc ccggggacct ccgacgccca aagctcggc gtggcctcct cgtcagaacc     1320
cacggttgtc atgccgccct cgacctgcac agggatgaac tttgccaacg tcctcccaac    1380
atttatgtct gctggttttg agattccaag cagccttcc ctgactgcct ttgggtcatc     1440
gtcatcgtcc aacacggcgg cagtgatgtc cctggtggg acgacgtcat ttctagacgt     1500
gttgagaggg ggcgcaggag ggcttcttga tggcagcctc agtcagaaca atggctacta   1560
ctatggtggg cctgccactg gatcaggcat tgggatgctg atgacgccgc cagtggcgtc    1620
atttggcatt ccaggtccga tgcagcaaca tggtgatctc gtggttggtg gaaatggaat    1680
aggtgctgca actgcttcaa tatttcaggg gggcactggc gaggaaggag atgatggtac   1740 gggggggcgtg atggggctcc aatggcagcc acaggttggc aatggtggag gtgctggtgt   1800
tgtatcagga ggcgtgcatc accttgggac tgggaacaat gtgacgatgg gcaacaacaa   1860
tatacacaac aacaacaata acaacagtgg gggtgatgac aacaatggtg cgtcatcgag    1920
ggattgctac tggatcaaca atggaggatc gaacccatgg cagagcctcc tcaacaacag    1980
ctccctgatg taagtgcaat aagaaaatgg gaaatggagg tcat                    2024

<210> SEQ ID NO 2
<211> LENGTH: 990
<212> TYPE: DNA
<213> ORGANISM: Triticum aestivum

<400> SEQUENCE: 2
atggaggaag tgtttccgtc aaactccaag agcaaggccg gtcagatggc ggggaggcg      60 acagcggcgg cggagaagaa gcctcggccg aagccagagc agaaggtgga atgccctcgg   120
tgcaagtctg caacaccaa gttctgctac tacaacaact atagtatgtc tcagccccgc    180
tacttctgca aggcctgccg ccgctactgg acccatggtg ctccctccg caacgtcccc    240 atcggtggcg ctgccgcaa gcccaagcgc ccggggacct ccgacgccca aagctcggc     300 gtggcctcct cgtcagaacc cacggttgtc atgccgccct cgacctgcac agggatgaac   360
tttgccaacg tcctcccaac atttatgtct gctggttttg agattccaag cagccttcc    420 ctgactgcct ttgggtcatc gtcatcgtcc aacacggcgg cagtgatgtc cctggtggg    480 acgacgtcat ttctagacgt gttgagaggg ggcgcaggag ggcttcttga tggcagcctc   540
agtcagaaca atggctacta ctatggtggg cctgccactg gatcaggcat tgggatgctg   600
atgacgccgc cagtggcgtc atttggcatt ccaggtccga tgcagcaaca tggtgatctc   660
gtggttggtg gaaatggaat aggtgctgca actgcttcaa tatttcaggg gggcactggc   720
gaggaaggag atgatggtac gggggggcgtg atggggctcc aatggcagcc acaggttggc   780
aatggtggag gtgctggtgt tgtatcagga ggcgtgcatc accttgggac tgggaacaat   840
gtgacgatgg gcaacaacaa tatacacaac aacaacaata acaacagtgg gggtgatgac   900
aacaatggtg cgtcatcgag ggattgctac tggatcaaca atggaggatc gaacccatgg   960
cagagcctcc tcaacaacag ctccctgatg                                    990

<210> SEQ ID NO 3
<211> LENGTH: 330
```

```
<212> TYPE: PRT
<213> ORGANISM: Triticum aestivum

<400> SEQUENCE: 3

Met Glu Glu Val Phe Pro Ser Asn Ser Lys Ser Lys Ala Gly Gln Met
1               5                   10                  15

Ala Gly Glu Ala Thr Ala Ala Glu Lys Lys Pro Arg Pro Lys Pro
            20                  25                  30

Glu Gln Lys Val Glu Cys Pro Arg Cys Lys Ser Gly Asn Thr Lys Phe
                35                  40                  45

Cys Tyr Tyr Asn Asn Tyr Ser Met Ser Gln Pro Arg Tyr Phe Cys Lys
            50                  55                  60

Ala Cys Arg Arg Tyr Trp Thr His Gly Gly Ser Leu Arg Asn Val Pro
65                  70                  75                  80

Ile Gly Gly Gly Cys Arg Lys Pro Lys Arg Pro Gly Thr Ser Asp Ala
                85                  90                  95

His Lys Leu Gly Val Ala Ser Ser Glu Pro Thr Val Val Met Pro
            100                 105                 110

Pro Ser Thr Cys Thr Gly Met Asn Phe Ala Asn Val Leu Pro Thr Phe
            115                 120                 125

Met Ser Ala Gly Phe Glu Ile Pro Ser Ser Leu Ser Leu Thr Ala Phe
130                 135                 140

Gly Ser Ser Ser Ser Asn Thr Ala Ala Val Met Ser Pro Gly Gly
145                 150                 155                 160

Thr Thr Ser Phe Leu Asp Val Leu Arg Gly Gly Ala Gly Gly Leu Leu
                165                 170                 175

Asp Gly Ser Leu Ser Gln Asn Asn Gly Tyr Tyr Gly Gly Pro Ala
                180                 185                 190

Thr Gly Ser Gly Ile Gly Met Leu Met Thr Pro Val Ala Ser Phe
            195                 200                 205

Gly Ile Pro Gly Pro Met Gln Gln His Gly Asp Leu Val Val Gly Gly
210                 215                 220

Asn Gly Ile Gly Ala Ala Thr Ala Ser Ile Phe Gln Gly Gly Thr Gly
225                 230                 235                 240

Glu Glu Gly Asp Asp Gly Thr Gly Gly Val Met Gly Leu Gln Trp Gln
                245                 250                 255

Pro Gln Val Gly Asn Gly Gly Ala Gly Val Val Ser Gly Gly Val
            260                 265                 270

His His Leu Gly Thr Gly Asn Asn Val Thr Met Gly Asn Asn Ile
            275                 280                 285

His Asn Asn Asn Asn Asn Ser Gly Gly Asp Asp Asn Asn Gly Ala
            290                 295                 300

Ser Ser Arg Asp Cys Tyr Trp Ile Asn Asn Gly Gly Ser Asn Pro Trp
305                 310                 315                 320

Gln Ser Leu Leu Asn Asn Ser Ser Leu Met
                325                 330

<210> SEQ ID NO 4
<211> LENGTH: 2028
<212> TYPE: DNA
<213> ORGANISM: Triticum aestivum

<400> SEQUENCE: 4
ctggcttgct cattttgcgg tagtgtttaa acattggctg gaattacggg tataaaagg     60 agggcaactt caccctatcc catagcacta gaccaaacaa ctcctatact ccatactacc   120
```

```
cttcattcac ctggtgagct tcttctttct ttgatttcta tcacttactc tttctccctc    180
gtccagcttc ttcttcttcc tcgtgcatgt gacttttgct agataatctc ccacattatc    240
gctcaatgca agccgtgcta gctagctagc gatctagcta gcgatcttca ctttaatacc    300
cgttgtagat ctaaccatgg gctattccaa aacatatttc tcttgtttgc gtgttcgtgt    360
gtacatgcat gcatctagat cttgattttg aggaattcat aagtaattcc tgacctacct    420
tgtttggttt gtttaatttt gatgttgttg tctcaatttt agcaaattgc tcgtagctag    480
aacaatagag ggggcggccg tatgtttccg ttttgaaaag gggatatttc caggctctgc    540
atcggttgat gcacacagcc gttaccacat tcaataggca ctgatccatg gatgcatgct    600
atatttacaa gttttctata gaattttttt ttatttatga aaaattggat cggtatagtt    660
cttctttatc catgtcggat tcactacttt gtacccaaga ttttatttat tttgtctcgg    720
tttcttacat gtctagttag gtaactagga gagcctggga ttaggctttc aaggaatcct    780
aatactagag actatgggga gagacagctt attctttaag ctgcgcaaaa gaatgggcgc    840
ttagagttgt agttgataaa ttgaatctgt tgtatggatt tgagaatttg agacctgatt    900
atgcacttat catgaaattt tgagttaacc aatgattcta catgtctcac tccttaggat    960
taacaattta acttaattta attcgatatg tgtgtacaca tgtgttgaag atggaggaag   1020
tgtttccgtc aaactccaag agcaaggctg gtcagatggc gggggaggcg acagcggcgg   1080
cggagaagaa gcctcggccg aagccagagc agaaggtgga atgccctcgg tgcaagtctg   1140
gcaacaccaa gttctgctac tacaacaact atagtatgtc tcagccccgc tacttctgca   1200
aggcctgccg ccgctactgg acccatggtg ggtccctccg taacgtcccc atcggtggtg   1260
gctgccgcaa gcccaagcgc tcggggacct ccgacgccca caagctcggc gtggcctcct   1320
cgtcggaaca cacggctgtc atgcccccct cgacctgcac agggataaac tttgccaatg   1380
tcctcccgac gttatgtctg ctggttttg agattccaag aagcctttcc ctgaccacct    1440
ttgggtcatc gtcgtcgtcc aacacgacgg ctgtcatgtc ccctggtggg acgacgtcat   1500
ttctagacgt gctgagaggg ggaacaggag ggcttcttga tggcaacctc ggtcagaaca   1560
atggctacta ctatggtggg tctagatcag gcattggat gctgatgacg ccgccagcgg    1620
cgtcatttgg cattccaggt ccaatgcagc agcatggcga tctcatggtt ggtggaaatg   1680
gaataggtgc cgcaactgct tcaatatttc aggggggcac tggtgaggaa ggagatgacg   1740
gcaaaggggc catgatgggg ctccaatggc agccacatgt tggtaatggt ggaggtggtg   1800
gtgttgtatc aggaggcgtg catcacccttg ggactgggaa caatgtgacg atgggcaaca   1860
acaacataaa caacaataac aataatggca gccacagtga tgacaacact ggtgggtcat   1920
cgagggattg ctactggatc aataatggag gatcgaaccc atggcaaagc ctcctcaata   1980
gcagctccct gatgtaagtg caagaagaaa atgcgaaatg gagatcat              2028
```

<210> SEQ ID NO 5
<211> LENGTH: 984
<212> TYPE: DNA
<213> ORGANISM: Triticum aestivum
<400> SEQUENCE: 5

```
atggaggaag tgtttccgtc aaactccaag agcaaggctg gtcagatggc gggggaggcg     60
acagcggcgg cggagaagaa gcctcggccg aagccagagc agaaggtgga atgccctcgg    120
tgcaagtctg gcaacaccaa gttctgctac tacaacaact atagtatgtc tcagccccgc    180
```

-continued

```
tacttctgca aggcctgccg ccgctactgg acccatggtg ggtccctccg taacgtcccc      240
atcggtggtg gctgccgcaa gcccaagcgc tcgggacct ccgacgccca caagctcggc       300
gtggcctcct cgtcggaaca cacggctgtc atgcccccct cgacctgcac agggataaac      360
tttgccaatg tcctcccgac gtttatgtct gctggttttg agattccaag aagcctttcc     420
ctgaccacct ttgggtcatc gtcgtcgtcc aacacgacgg ctgtcatgtc cctggtggg      480 acgacgtcat ttctagacgt gctgagaggg ggaacaggag ggcttcttga tggcaacctc     540
ggtcagaaca atggctacta ctatggtggg tctagatcag gcattgggat gctgatgacg      600
ccgccagcgg cgtcatttgg cattccaggt ccaatgcagc agcatggcga tctcatggtt     660
ggtggaaatg gaataggtgc cgcaactgct tcaatatttc aggggggcac tggtgaggaa      720
ggagatgacg gcaaagggc catgatgggg ctccaatggc agccacatgt tggtaatggt       780
ggaggtggtg gtgttgtatc aggaggcgtg catcaccttg gactgggaa caatgtgacg       840 atgggcaaca acaacataaa caacaataac aataatggca gccacagtga tgacaacact     900
ggtgggtcat cgagggattg ctactggatc aataatggag gatcgaaccc atggcaaagc     960
ctcctcaata gcagctccct gatg                                            984

<210> SEQ ID NO 6
<211> LENGTH: 328
<212> TYPE: PRT
<213> ORGANISM: Triticum aestivum

<400> SEQUENCE: 6

Met Glu Glu Val Phe Pro Ser Asn Ser Lys Ser Lys Ala Gly Gln Met
1               5                   10                  15

Ala Gly Glu Ala Thr Ala Ala Glu Lys Lys Pro Arg Pro Lys Pro
            20                  25                  30

Glu Gln Lys Val Glu Cys Pro Arg Cys Lys Ser Gly Asn Thr Lys Phe
        35                  40                  45

Cys Tyr Tyr Asn Asn Tyr Ser Met Ser Gln Pro Arg Tyr Phe Cys Lys
    50                  55                  60

Ala Cys Arg Arg Tyr Trp Thr His Gly Gly Ser Leu Arg Asn Val Pro
65                  70                  75                  80

Ile Gly Gly Gly Cys Arg Lys Pro Lys Arg Ser Gly Thr Ser Asp Ala
                85                  90                  95

His Lys Leu Gly Val Ala Ser Ser Glu His Thr Ala Val Met Pro
            100                 105                 110

Pro Ser Thr Cys Thr Gly Ile Asn Phe Ala Asn Val Leu Pro Thr Phe
        115                 120                 125

Met Ser Ala Gly Phe Glu Ile Pro Arg Ser Leu Ser Leu Thr Thr Phe
    130                 135                 140

Gly Ser Ser Ser Ser Asn Thr Thr Ala Val Met Ser Pro Gly Gly
145                 150                 155                 160

Thr Thr Ser Phe Leu Asp Val Leu Arg Gly Thr Gly Gly Leu Leu
                165                 170                 175

Asp Gly Asn Leu Gly Gln Asn Asn Gly Tyr Tyr Tyr Gly Gly Ser Arg
            180                 185                 190

Ser Gly Ile Gly Met Leu Met Thr Pro Pro Ala Ala Ser Phe Gly Ile
        195                 200                 205

Pro Gly Pro Met Gln Gln His Gly Asp Leu Met Val Gly Gly Asn Gly
    210                 215                 220

Ile Gly Ala Ala Thr Ala Ser Ile Phe Gln Gly Gly Thr Gly Glu Glu
```

```
                225                 230                 235                 240
Gly Asp Asp Gly Lys Gly Ala Met Met Gly Leu Gln Trp Gln Pro His
                245                 250                 255

Val Gly Asn Gly Gly Gly Gly Val Val Ser Gly Gly Val His His
            260                 265                 270

Leu Gly Thr Gly Asn Asn Val Thr Met Gly Asn Asn Ile Asn Asn
                275                 280                 285

Asn Asn Asn Asn Gly Ser His Ser Asp Asp Asn Thr Gly Gly Ser Ser
            290                 295                 300

Arg Asp Cys Tyr Trp Ile Asn Asn Gly Gly Ser Asn Pro Trp Gln Ser
305                 310                 315                 320

Leu Leu Asn Ser Ser Ser Leu Met
                325

<210> SEQ ID NO 7
<211> LENGTH: 2081
<212> TYPE: DNA
<213> ORGANISM: Triticum aestivum

<400> SEQUENCE: 7
```

| | | | | |
|---|---|---|---|---|
| ctggcttgct cattctgcgg tagtgtttaa acatcagcta gccttacggg tataaaaagg | 60 |
| tgggcaactt caccctatcc catagcacta gaccaaacaa cacctatact ccatactacc | 120 |
| cttcattcac ctggtgagat tcttcttcct ttgatctcta tcacttactc tttctccctt | 180 |
| cttcttcttc ttcttcttct tcttcttctt cttcttcttc ttcttcttct tcttcttctt | 240 |
| cctcgtgcat gctactttg ctacataatc tcctgcagta tcgctcgccg caagctgtgc | 300 |
| tagctagcta gcgatcttca ctttaagacc cgttgtagat ctagccacgg gctattccaa | 360 |
| aaaatatttc tcttgtttgc gtgttcctgt gtacatgcat gtatttagat cttgatcttg | 420 |
| aagaattcat actgaattca tgacctacct tgtttggttt gtgtaatttt gatgttgttg | 480 |
| tatcaatttt agcaaaccgc tcgtagctag aacaatagag ggggcggccg tatgtttcca | 540 |
| tttcgaaaag gggatatttc caggctctgc atcggttcat gcacacagcc gttaccacat | 600 |
| tcaataggca ctaatccatg gatgcatgcc agatttacta gttttgttta caaagtttta | 660 |
| tttttttttg ctttgattta cgaaaaattg gatcggattt tgcagttctt ttttatccat | 720 |
| gttggattca ctactttgaa cccaagattt tatttatttt gtctcggttt cttacacgcc | 780 |
| tggttaggta actaggagat cctgggatta ggctttcaag gaatcctaat actagagagt | 840 |
| atggggagag gcaccttatt ttttaagttg cccaaaagaa tgggcgctta gagttgtagc | 900 |
| taattaattg aatctgttgt atggatctga gaatttgaga cctgattatg cacttatcat | 960 |
| gacattttga gtcaaccaat gattctacat gtctcactcc ttaggattaa caattttaact | 1020 |
| taatttaatt cgatatgtgt gtacacatgt gttgtagatg gaggaagtgt ttccgtcaaa | 1080 |
| ctccaagagc aaggcaggtc agatggcggg ggaggcgata gcggggcggg agaagaagcc | 1140 |
| tcggccaaag ccagagcaga aggtggaatg ccctcggtgc aagtctggca acaccaagtt | 1200 |
| ctgctactac aacaactata gtatgtctca gccccgctac ttctgcaagg cctgccgccg | 1260 |
| ctactggacc catggtggct ccctccgcaa cgtcccatc ggtggtggct gccgcaagcc | 1320 |
| caagcgctcg ggacctccg acgcccacaa gctcggcgtg gcctcctcac cggaacccac | 1380 |
| gactgtcgtg cccccctcga cctgcacagg gatgaacttt gcgaacgtcc tcccgacgtt | 1440 |
| tatgtctgtt ggttttgaga ttccaagcag cctttcccta accgcctttg ggtcatcatc | 1500 |
| gtcgtccaac acggcggcga tgatgtcccc tggtgggacg acgtcatttc tagacgtgct | 1560 |

```
aagaggggt gcaggagggc ttcttgatgg cagcctcagt cagaacaatg gctactacta      1620
tggtgggcca gccattggat caggcaatgg gatgctgatg acgccgccag cggtgtcatt     1680
tggcattcca gttccgatgc agcagcatgg tgatctcgtg gttggtggaa atggaatagg     1740
tgccgcaact gcttcaatat ttcaaggggc cactagcgag gaaggagatg acggcatggg    1800
gggcgtgatg gggctccaat ggcaaccaca ggttggcaat ggtggaggtg gtggtggtgt    1860
atcaggaggc gtgcatcacc ttgggactgg gaacaatgtg acgatgggca acagcaacat    1920
acacaacaac aacaataacg acagcggcgg tgatgacaac aatggtgggt catcgaggga    1980
ttgctactgg atcaacaatg gaggatcaaa cccatggcag agcctcctca acagcagctc    2040
cctgatgtaa gtgcaagaag aaaatgggaa atggaggtca t                         2081
```

<210> SEQ ID NO 8
<211> LENGTH: 990
<212> TYPE: DNA
<213> ORGANISM: Triticum aestivum

<400> SEQUENCE: 8

```
atggaggaag tgtttccgtc aaactccaag agcaaggcag gtcagatggc gggggaggcg     60
atagcggggg cggagaagaa gcctcggcca agccagagc agaaggtgga atgccctcgg      120
tgcaagtctg gcaacaccaa gttctgctac tacaacaact atagtatgtc tcagccccgc    180
tacttctgca aggcctgccg ccgctactgg acccatggtg gctccctccg caacgtcccc    240
atcggtggtg gctgccgcaa gcccaagcgc tcggggacct ccgacgccca caagctcggc    300
gtggcctcct caccggaacc cacgactgtc gtgcccccct cgacctgcac agggatgaac    360
tttgcgaacg tcctcccgac gtttatgtct gttggttttg agattccaag cagcctttcc    420
ctaaccgcct ttgggtcatc atcgtcgtcc aacacgcgg cgatgatgtc ccctggtggg     480
acgacgtcat ttctagacgt gctaagaggg ggtgcaggag ggcttcttga tggcagcctc    540
agtcagaaca atggctacta ctatggtggg ccagccattg gatcaggcaa tgggatgctg    600
atgacgccgc cagcggtgtc atttggcatt ccagttccga tgcagcagca tggtgatctc    660
gtggttggtg gaaatggaat aggtgccgca actgcttcaa tatttcaagg ggccactagc    720
gaggaaggag atgacggcat ggggggcgtg atgggctcc aatggcaacc acaggttggc    780
aatggtggag gtggtggtgg tgtatcagga ggcgtgcatc accttgggac tgggaacaat    840
gtgacgatgg gcaacagcaa catacacaac aacaacaata cgacagcgg cggtgatgac    900 aacaatggtg ggtcatcgag ggattgctac tggatcaaca atggaggatc aaacccatgg    960
cagagcctcc tcaacagcag ctccctgatg                                      990
```

<210> SEQ ID NO 9
<211> LENGTH: 330
<212> TYPE: PRT
<213> ORGANISM: Triticum aestivum

<400> SEQUENCE: 9

```
Met Glu Glu Val Phe Pro Ser Asn Ser Lys Ser Lys Ala Gly Gln Met
1               5                   10                  15

Ala Gly Glu Ala Ile Ala Gly Ala Glu Lys Lys Pro Arg Pro Lys Pro
            20                  25                  30

Glu Gln Lys Val Glu Cys Pro Arg Cys Lys Ser Gly Asn Thr Lys Phe
        35                  40                  45

Cys Tyr Tyr Asn Asn Tyr Ser Met Ser Gln Pro Arg Tyr Phe Cys Lys
```

```
            50                  55                  60
Ala Cys Arg Arg Tyr Trp Thr His Gly Gly Ser Leu Arg Asn Val Pro
 65                  70                  75                  80

Ile Gly Gly Gly Cys Arg Lys Pro Lys Arg Ser Gly Thr Ser Asp Ala
                 85                  90                  95

His Lys Leu Gly Val Ala Ser Ser Pro Glu Pro Thr Thr Val Val Pro
            100                 105                 110

Pro Ser Thr Cys Thr Gly Met Asn Phe Ala Asn Val Leu Pro Thr Phe
            115                 120                 125

Met Ser Val Gly Phe Glu Ile Pro Ser Ser Leu Ser Leu Thr Ala Phe
        130                 135                 140

Gly Ser Ser Ser Ser Asn Thr Ala Ala Met Met Ser Pro Gly Gly
145                 150                 155                 160

Thr Thr Ser Phe Leu Asp Val Leu Arg Gly Ala Gly Gly Leu Leu
            165                 170                 175

Asp Gly Ser Leu Ser Gln Asn Asn Gly Tyr Tyr Tyr Gly Gly Pro Ala
            180                 185                 190

Ile Gly Ser Gly Asn Gly Met Leu Met Thr Pro Pro Ala Val Ser Phe
            195                 200                 205

Gly Ile Pro Val Pro Met Gln Gln His Gly Asp Leu Val Val Gly Gly
    210                 215                 220

Asn Gly Ile Gly Ala Ala Thr Ala Ser Ile Phe Gln Gly Ala Thr Ser
225                 230                 235                 240

Glu Glu Gly Asp Asp Gly Met Gly Gly Val Met Gly Leu Gln Trp Gln
                245                 250                 255

Pro Gln Val Gly Asn Gly Gly Gly Gly Gly Val Ser Gly Gly Val
            260                 265                 270

His His Leu Gly Thr Gly Asn Asn Val Thr Met Gly Asn Ser Asn Ile
            275                 280                 285

His Asn Asn Asn Asn Asp Ser Gly Gly Asp Asp Asn Asn Gly Gly
        290                 295                 300

Ser Ser Arg Asp Cys Tyr Trp Ile Asn Asn Gly Gly Ser Asn Pro Trp
305                 310                 315                 320

Gln Ser Leu Leu Asn Ser Ser Ser Leu Met
                325                 330

<210> SEQ ID NO 10
<211> LENGTH: 189
<212> TYPE: DNA
<213> ORGANISM: Triticum aestivum

<400> SEQUENCE: 10
aagccagagc agaaggtgga atgccctcgg tgcaagtctg gcaacaccaa gttctgctac      60
tacaacaact atagtatgtc tcagccccgc tacttctgca aggcctgccg ccgctactgg     120
acccatggtg ctcccctccg caacgtcccc atcggtggtg ctgccgcaa gcccaagcgc      180 tcggggacc                                                            189

<210> SEQ ID NO 11
<211> LENGTH: 63
<212> TYPE: PRT
<213> ORGANISM: Triticum aestivum

<400> SEQUENCE: 11

Lys Pro Glu Gln Lys Val Glu Cys Pro Arg Cys Lys Ser Gly Asn Thr
 1               5                  10                  15
```

Lys Phe Cys Tyr Tyr Asn Asn Tyr Ser Met Ser Gln Pro Arg Tyr Phe
            20                  25                  30

Cys Lys Ala Cys Arg Arg Tyr Trp Thr His Gly Gly Ser Leu Arg Asn
        35                  40                  45

Val Pro Ile Gly Gly Cys Arg Lys Pro Lys Arg Ser Gly Thr
    50                  55                  60

<210> SEQ ID NO 12
<211> LENGTH: 1011
<212> TYPE: DNA
<213> ORGANISM: Hordeum vulgare

<400> SEQUENCE: 12

```
atggaggaag tgttttcgtc caactccaag agcaaggccg gtcagatggc gggagaggcg      60
gtggcggcgg ccgagaagaa gtctcggccg aagccagagc agaaggtgga gtgcctcgg     120
tgcaagtctg gtaacaccaa gttctgctac tacaacaact acagcatgtc ccagccgcgc    180
tacttctgca aggcctgccg ccgctactgg acccatggtg gctccctccg caacgtcccc    240
atcggtggtg gttgccgcaa gcccaaacgc ccggggacct ctgacgccca caagctcggc    300
atggcctcct catcggaacc cacgggtgtc gtgcccccct cgaactgcac agggatgaac    360
tttgctaacg tcctcccgac gtttatgtct ggtggctttg acattcaaag cagcctctcc    420
ctgacaactt ttgggtcatc atcctcatcc aacccgacgg ggttgatgtc ccccggtggg    480
acgacttcat ttctggatgt gctgagaggt ggtgcaggag gcttcttga tggcagcctc     540
ggtccaaaca atggctacta ctatggtggg catgccaatg atcaggcat gggatgttg      600
atgactccgc aacggtatc gtttggcatt ccaagtccga tgcaacaaca tggcggtctc    660
gtggttggtg gaaatggaat aggtggcaca acttcttcaa catttcaggg caacgctggc    720
gaggaaggag acgatggtac ggggtccatt atggggctcc agtggcagcc acatgttggt    780
aatggtggcg gtggtggtgt tggattagga ggcgcgcatc atcttgggac tgggaacaat    840
gtgacgatgg gcaacaacaa caataataac aaccagaaca caataacgg cggcggtgct    900
ggtgatgacg acgatggtgg gtcatcgagg gattgctact ggatcaacaa tggaggatcg    960
aacccatggc agagcctcct caacagcacc tccctgatct catacacacc a            1011
```

<210> SEQ ID NO 13
<211> LENGTH: 337
<212> TYPE: PRT
<213> ORGANISM: Hordeum vulgare

<400> SEQUENCE: 13

Met Glu Glu Val Phe Ser Ser Asn Ser Lys Ser Lys Ala Gly Gln Met
1               5                   10                  15

Ala Gly Glu Ala Val Ala Ala Ala Glu Lys Lys Ser Arg Pro Lys Pro
            20                  25                  30

Glu Gln Lys Val Glu Cys Pro Cys Lys Ser Gly Asn Thr Lys Phe
            35                  40                  45

Cys Tyr Tyr Asn Asn Tyr Ser Met Ser Gln Pro Arg Tyr Phe Cys Lys
50                  55                  60

Ala Cys Arg Arg Tyr Trp Thr His Gly Gly Ser Leu Arg Asn Val Pro
65                  70                  75                  80

Ile Gly Gly Gly Cys Arg Lys Pro Lys Arg Pro Gly Thr Ser Asp Ala
                85                  90                  95

His Lys Leu Gly Met Ala Ser Ser Ser Glu Pro Thr Gly Val Val Pro

-continued

```
               100                 105                 110
Pro Ser Asn Cys Thr Gly Met Asn Phe Ala Asn Val Leu Pro Thr Phe
            115                 120                 125

Met Ser Gly Gly Phe Asp Ile Gln Ser Ser Leu Ser Leu Thr Thr Phe
            130                 135                 140

Gly Ser Ser Ser Ser Asn Pro Thr Gly Leu Met Ser Pro Gly Gly
145             150                 155                 160

Thr Thr Ser Phe Leu Asp Val Leu Arg Gly Ala Gly Gly Leu Leu
                165                 170                 175

Asp Gly Ser Leu Gly Pro Asn Asn Gly Tyr Tyr Gly Gly His Ala
            180                 185                 190

Asn Gly Ser Gly Ile Gly Met Leu Met Thr Pro Pro Thr Val Ser Phe
            195                 200                 205

Gly Ile Pro Ser Pro Met Gln Gln His Gly Gly Leu Val Val Gly Gly
        210                 215                 220

Asn Gly Ile Gly Gly Thr Thr Ser Ser Thr Phe Gln Gly Asn Ala Gly
225                 230                 235                 240

Glu Glu Gly Asp Asp Gly Thr Gly Ser Ile Met Gly Leu Gln Trp Gln
                245                 250                 255

Pro His Val Gly Asn Gly Gly Gly Gly Val Gly Leu Gly Gly Ala
            260                 265                 270

His His Leu Gly Thr Gly Asn Asn Val Thr Met Gly Asn Asn Asn
            275                 280                 285

Asn Asn Asn Gln Asn Asn Asn Gly Gly Gly Ala Gly Asp Asp Asp
        290                 295                 300

Asp Gly Gly Ser Ser Arg Asp Cys Tyr Trp Ile Asn Asn Gly Gly Ser
305             310                 315                 320

Asn Pro Trp Gln Ser Leu Leu Asn Ser Thr Ser Leu Ile Ser Tyr Thr
                325                 330                 335

Pro
```

REDUCED GLUTEN GRAINS AND COMPOSITIONS THEREOF

CROSS-REFERENCE TO RELATED APPLICATIONS

This application is a continuation patent application of U.S. patent application Ser. No. 15/994,601 filed May 31, 2018, which is a continuation patent application of U.S. patent application Ser. No. 15/577,588 filed Nov. 28, 2017, which is a National Stage application of PCT/US2016/035057 filed May 31, 2016, which claims priority to U.S. Provisional Patent Application No. 62/327,822 filed Apr. 26, 2016, and U.S. Provisional Patent Application No. 62/263,912 filed Dec. 7, 2015, and U.S. Provisional Patent Application No. 62/168,536 filed May 29, 2015; each of the above referenced applications is incorporated herein by reference in its entirety.

STATEMENT REGARDING FEDERALLY SPONSORED RESEARCH OR DEVELOPMENT

This invention was made with government support under grant numbers 1R42DK097976-01 and 4R42DK097976-02 awarded by the National Institute of Health. The government has certain rights in the invention.

FIELD

In one embodiment, the disclosure relates to reduced gluten grains.

SUBMISSION OF SEQUENCE LISTING

The contents of the electronic submission of the text file Sequence Listing, which is named ARC-38939-A.txt, which was created May 8, 2018, and is 26.2 KB in size, is incorporated herein by reference in its entirety.

BACKGROUND

Wheat is the first important and strategic cereal crop for the majority of the world's population and is the most important staple food of about two billion people (36% of the world population). Worldwide, wheat provides nearly 55% of the carbohydrates and 20% of the food calories consumed globally (Breiman and Graur, 1995). Wheat exceeds in acreage and production every other grain crop (including rice, maize, etc.) and is cultivated over a wide range of climatic conditions. The understanding of wheat genetics and genome organization using molecular markers is of great value for genetic and plant breeding purposes.

Proteins are the most important component of wheat grain governing its end-use value. Grain storage protein (GSP) composition is known to determine dough cohesiveness and visco-elasticity. The most abundant GSPs in wheat are the gluten-forming gliadins and glutenins, which account for 60% to 80% of total grain protein.

Coeliac disease is a condition in which the lining of the small intestine is damaged by gluten, a mixture of different storage proteins found in the starchy endosperm of wheat, rye and barley grains as well as in closely related species. The gluten matrix consists of approximately equal mixtures of gliadin and glutenin proteins. Coeliac disease is primarily caused by the gliadin proteins. Specifically, in this disease the villi of the small intestine are destroyed and the lining becomes flattened, seriously impairing nutrient absorption. Typical symptoms are weight loss, foul-smelling diarrhea, vomiting, abdominal pain and swelling of the legs. The only cure currently available is a life-long gluten-free diet strictly avoiding all food and pharmaceutical compositions containing wheat, rye and barley. In addition to Coeliac disease, a number of humans suffer from general intolerance to glutens. The range of this intolerance varies greatly although there are no clear clinical symptoms as in coeliac disease.

Thus, there is a clinical need to reduce consumption of gluten and a corresponding need to develop wheat and other grains with reduced gluten. Although the need has been long felt, the identification of mutations in wheat genes that reduce gluten has proceeded slowly because, among other possible reasons, there is limited genetic diversity in today's commercial wheat cultivars and the wheat genome is complex. Bread wheat is a hexaploid, with three complete genomes termed A, B and D in the nucleus of each cell. Each of these genomes is almost twice the size of the human genome and consists of around 5,500 million nucleotides. On the other hand, durum wheat, also known as macaroni wheat or pasta wheat (*Triticum durum* or *Triticum turgidum* subsp. *durum*), is the major tetraploid species of wheat of commercial importance, which is widely cultivated today. Durum wheat has two complete genomes, A and B, and is widely used for making pasta.

The inventors have identified genes, wherein mutations and modification of said genes produce reduced gluten grains.

SUMMARY

In one embodiment, the disclosure relates to plants with one or more non-transgenic mutations in a gene that result in reduced gluten grains, including but not limited to grains from barley and wheat plants. In still another embodiment, the disclosure relates to plants with one or more transgenes that alters expression of a gene and/or activity of a protein, which results in reduced gluten grains. In another embodiment, the disclosure relates to transgenic plants with reduced gluten grains. In yet another embodiment, the disclosure relates to plants with modified genes, wherein the genes were modified by genomic editing and contribute to grains with reduced gluten as compared to grains from wild type plants.

In one embodiment, the grains discussed herein include wheat, barley and rye.

In one embodiment, the disclosure relates to plants with non-transgenic mutations in one or more wheat prolamin box binding factor (WPBF) genes, or homologous genes, which result in reduced gluten grains. In one embodiment, the disclosure relates to non-transgenic mutations in the WPBF gene, wherein said mutations result in reduced gluten grains.

In one embodiment, one or more mutations are in the WPBF gene of the A genome. In another embodiment, one or more mutations are in the WPBF gene of the B genome. In another embodiment, one or more mutations are in the WPBF gene of the D genome.

In one embodiment, the invention relates to multiple non-transgenic mutations in the WPBF gene including but not limited to 1, 2, 3, 4, 5, 6, 7, 8, 9, 10, and greater than 10 mutations.

In another embodiment, the invention relates to multiple non-transgenic mutations in the WPBF gene of the A genome including but not limited to 1, 2, 3, 4, 5, 6, 7, 8, 9, 10, and greater than 10 mutations and multiple mutations in the WPBF gene of the B genome including but not limited to 1, 2, 3, 4, 5, 6, 7, 8, 9, 10, and greater than 10 mutations.

In another embodiment, the invention relates to multiple non-transgenic mutations in the WPBF gene of the A genome including but not limited to 1, 2, 3, 4, 5, 6, 7, 8, 9, 10, and greater than 10 mutations and multiple mutations in the WPBF gene of the D genome including but not limited to 1, 2, 3, 4, 5, 6, 7, 8, 9, 10, and greater than 10 mutations.

In another embodiment, the invention relates to multiple non-transgenic mutations in the WPBF gene of the B genome including but not limited to 1, 2, 3, 4, 5, 6, 7, 8, 9, 10, and greater than 10 mutations and multiple mutations in the WPBF gene of the D genome including but not limited to 1, 2, 3, 4, 5, 6, 7, 8, 9, 10, and greater than 10 mutations.

In another embodiment, the invention relates to multiple non-transgenic mutations in the WPBF gene of the A genome including but not limited to 1, 2, 3, 4, 5, 6, 7, 8, 9, 10, and greater than 10 mutations and multiple mutations in the WPBF gene of the B genome including but not limited to 1, 2, 3, 4, 5, 6, 7, 8, 9, 10, and greater than 10 mutations and multiple mutations in the WPBF gene of the D genome including but not limited to 1, 2, 3, 4, 5, 6, 7, 8, 9, 10, and greater than 10 mutations.

In another embodiment, the disclosure relates to a wheat plant, wheat seeds, wheat plant parts, and progeny thereof with reduced gluten grains as compared to wild type wheat plant, wheat seeds, wheat plant parts, and progeny thereof.

In another embodiment, the disclosure relates to a wheat plant, wheat seeds, wheat plant parts, and progeny thereof with increased high molecular weight glutenins as compared to wild type wheat plant, wheat seeds, wheat plant parts, and progeny thereof.

In another embodiment, the disclosure relates to a wheat plant, wheat seeds, wheat plant parts, and progeny thereof with decreased low molecular weight glutenins as compared to wild type wheat plant, wheat seeds, wheat plant parts, and progeny thereof.

In another embodiment, the disclosure relates to a wheat plant, wheat seeds, wheat plant parts, and progeny thereof with decreased gliadins as compared to wild type wheat plant, wheat seeds, wheat plant parts, and progeny thereof.

In another embodiment, this invention relates to a wheat plant, wheat seeds, wheat plant parts, and progeny thereof having reduced gluten grains as compared to the wild type wheat plant, wherein the reduction in gluten is caused by a human-induced non-transgenic mutation in one or more of the wheat plant's WPBF genes. In another embodiment, the WPBF protein has reduced activity.

In another embodiment, the disclosure relates to a wheat plant containing one or more mutated WPBF genes, as well as seeds, pollen, plant parts and progeny of that plant.

In another embodiment, the disclosure relates to food and food products incorporating wheat seeds and wheat flour having reduced WPBF protein activity caused by a human-induced non-transgenic mutation in one or more WPBF genes.

In another embodiment, this disclosure relates to a wheat plant having reduced activity of one or more WPBF proteins compared to the wild type wheat plants, created by the steps of obtaining plant material from a parent wheat plant, inducing at least one mutation in at least one copy of a WPBF gene of the plant material by treating the plant material with a mutagen to create mutagenized plant material (e.g., seeds or pollen), analyzing progeny wheat plants to detect at least one mutation in at least one copy of a WPBF gene, selecting progeny wheat plants that have at least one mutation in at least one copy of a WPBF gene, crossing progeny wheat plants that have at least one mutation in at least one copy of a WPBF gene with other progeny wheat plants that have at least one mutation in a different copy of a WPBF gene, and repeating the cycle of identifying progeny wheat plants having mutations and crossing the progeny wheat plants having mutations with other progeny wheat plants having mutations to produce progeny wheat plants with reduced WPBF activity. In another embodiment, the method comprises growing or using the mutagenized plant material to produce progeny wheat plants.

In one embodiment, the disclosure relates to seeds from a wheat plant having an altered protein storage profile.

In one embodiment, the disclosure relates to a composition comprising wheat seeds having reduced WPBF protein activity caused by a mutation in one or more WPBF genes and a glutenase.

In yet another embodiment, the disclosure relates to a composition comprising wheat flour having reduced WPBF protein activity caused by a mutation in one or more WPBF genes and a glutenase.

In one embodiment, the disclosure relates to a composition comprising food and/or food products incorporating wheat seeds and wheat flour having reduced WPBF protein activity caused by a human-induced non-transgenic mutation in one or more WPBF genes and a glutenase.

In one embodiment, the disclosure relates to a composition comprising food and/or food products incorporating barley seeds and/or barley flour having reduced barley Dof transcription factor activity and a glutenase.

In yet another embodiment, the disclosure relates to a composition comprising food and/or food products incorporating ultra-low gluten barley and a glutenase.

In one embodiment, the glutenase is selected from the group consisting of Tolerase® G, Glutenase ALV003, GlutenEase, Glutenase Plus, Digest Gluten Plus, Gluten Cutter.

In another embodiment, the glutenase can be used with one or more additional enzymes including but not limited to amylase, glucoamylase, and DPP4 (dipeptidyl peptidase-4).

BRIEF DESCRIPTION OF THE SEQUENCE LISTING

SEQ ID NO. 1 shows the gene sequence for wheat prolamin box binding factor (WPBF) of the A genome (2,024base pairs).
SEQ ID NO. 2 shows the WPBF-A coding sequence of SEQ ID NO: 1 (990 base pairs).
SEQ ID NO. 3 shows the WPBF-A protein sequence of SEQ ID NO. 2 (330 amino acids).
SEQ ID NO. 4 shows the gene for wheat prolamin box binding factor (WPBF) gene of the B genome (2,027 base pairs).
SEQ ID NO. 5 shows the WPBF-B coding sequence of SEQ ID NO: 4 (984 base pairs).
SEQ ID NO. 6 shows the WPBF-B protein sequence of SEQ ID NO. 5 (328 amino acids).
SEQ ID NO. 7 shows the gene sequence for wheat prolamin box binding factor (WPBF) gene of the D genome (2,081 base pairs).
SEQ ID NO. 8 shows the WPBF-D coding sequence of SEQ ID NO: 7 (990 base pairs).
SEQ ID NO. 9 shows the WPBF-D protein sequence of SEQ ID NO. 8 (330 amino acids).
SEQ ID NO. 10 shows the nucleic acid sequence of the Dof region of the WPBF gene.
SEQ ID NO. 11 shows the amino acid sequence of the Dof region of the WPBF protein.

SEQ ID NO. 12 shows the Barley (*Hordeum vulgare*; Hv) DOF coding sequence (1,011 base pairs)

SEQ ID NO. 13 shows the protein sequence of SEQ ID NO. 12 (337 amino acids).

BRIEF DESCRIPTION OF THE DRAWINGS

FIG. 1B has a five-fold increase in protein loaded for the mutant low gluten barley lanes compared to the same lanes in FIG. 1A.

DETAILED DESCRIPTION

Definitions

Figure 1A:
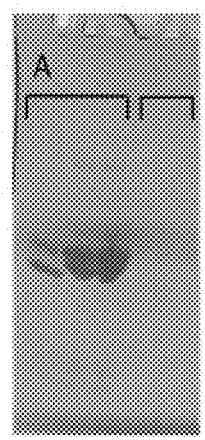
FIGS. 1A and 1B are photographs of an SDS polyacrylamide gel showing B, C, and D hordeins present in wild type barley and mutant low gluten barley.

The numerical ranges in this disclosure are approximate, and thus may include values outside of the range unless otherwise indicated. Numerical ranges include all values from and including the lower and the upper values, in increments of one unit, provided that there is a separation of at least two units between any lower value and any higher value. As an example, if a compositional, physical or other property, such as, for example, molecular weight, viscosity, etc., is from 100 to 1,000, it is intended that all individual values, such as 100, 101, 102, etc., and sub ranges, such as 100 to 144, 155 to 170, 197 to 200, etc., are expressly enumerated. For ranges containing values which are less than one or containing fractional numbers greater than one (e.g., 1.1, 1.5, etc.), one unit is considered to be 0.0001, 0.001, 0.01 or 0.1, as appropriate. For ranges containing single digit numbers less than ten (e.g., 1 to 5), one unit is typically considered to be 0.1. These are only examples of what is specifically intended, and all possible combinations of numerical values between the lowest value and the highest value enumerated, are to be considered to be expressly stated in this disclosure. Numerical ranges are provided within this disclosure for, among other things, relative amounts of components in a mixture, and various temperature and other parameter ranges recited in the methods.

As used herein, the term "allele" is any of one or more alternative forms of a gene, all of which relate to one trait or characteristic. In a diploid cell or organism, the two alleles of a given gene occupy corresponding loci on a pair of homologous chromosomes. In a tetraploid or hexaploid cell or organism, such as wheat, the two alleles of a given gene on one of the genomes occupy corresponding loci on a pair of homologous chromosomes and the two alleles of the same gene occupying the same loci on another of the genomes such as the A or B genomes of tetraploid, or the A, B or D genomes of hexaploid wheat are said to be homoeologous to the gene of the first genome and to be present on homoeologous chromosomes.

As used herein, the terms "altering," "increasing," "increased," "reducing," "reduced," "inhibited" or the like are considered relative terms, i.e. in comparison with the wild-type or unaltered state. The "level of a protein" refers to the amount of a particular protein, for example WPBF, which may be measured by any means known in the art such as, for example, Western blot analysis or other immunological means. As used herein, "transcription factor ("TF") activity" refers to the extent to which the TF activates the transcription of its target genes.

As used herein, "WPBF activity" may be measured by one or more of the following characteristics: (1) extent to which WPBF activates transcription; (2) the extent to which WPBF binds DNA; (3) the extent to which WPBF binds to co-activators and/or other transcriptional regulatory complexes; and (4) the stability of WPBF bound to DNA. It would be appreciated that the level of WPBF activity or the level of transcription factor activity might be altered in a mutant but not the expression level (amount) of the protein itself. Conversely, the amount of protein might be altered but the activity remain the same if a more or less active protein is produced. Reductions in both amount and activity are also possible such as, for example, when a gene encoding the enzyme is inactivated. In certain embodiments, the reduction in the level of protein or activity is by at least 10% or by at least 20% or by at least 30% or by at least 40% or by at least 50% or by at least 60% compared to the level of protein or activity in the endosperm of unmodified wheat, or by at least 70%, or by at least 80% or by at least 85% or by at least 90% or at least 95%. The reduction in the level of the protein or gene expression or level of WPBF activity or level of transcription factor activity may occur at any stage in the development of the grain, particularly during the grain filling stage, or at all stages of grain development through to maturity.

As used herein, amino acid or nucleotide sequence "identity" and "similarity" are determined from an optimal global alignment between the two sequences being compared. An optimal global alignment is achieved using, for example, the Needleman-Wunsch algorithm (Needleman and Wunsch, 1970, J. Mol. Biol. 48:443-453). Sequences may also be aligned using algorithms known in the art including but not limited to CLUSTAL V algorithm or the Blastn or BLAST 2 sequence programs.

As used herein, the term "barley" refers to any species of the Genus *Hordeum*, including progenitors thereof as well as progeny thereof produced by crosses with other species. A preferred form of barley is the species *Hordeum vulgare*.

As used herein, barley Dof transcription factor refers to Barley transcript MLOC_12852.2, a Dof transcription factor.

As used herein, a "modified barley Dof transcription factor gene" includes modification of the barley Dof transcription factor gene through non-transgenic mutations or transgenes or genomic editing or combinations thereof.

"Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the Blosum62 substitution matrix (Hentikoff and Hentikoff, 1992, Proc. Natl. Acad. Sci. USA 89: 10915-10919).

By the statement "sequence A is n % similar to sequence B," it is meant that n % of the positions of an optimal global alignment between sequences A and B consists of identical residues or nucleotides and conservative substitutions. By the statement "sequence A is n % identical to sequence B," it is meant that n % of the positions of an optimal global alignment between sequences A and B consists of identical residues or nucleotides.

As used herein, the term "gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found within an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit. A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

As used herein, the term "modified plant" includes a plant that has a non-transgenic mutation, or a plant containing a transgene, or a plant that has undergone genomic editing or combinations thereof.

As used herein, the term "plant" includes reference to an immature or mature whole plant, including a plant from which seed or grain or anthers have been removed. A seed or embryo that will produce the plant is also considered to be the plant.

As used herein, the term "plant parts" includes plant protoplasts, plant cell tissue cultures from which wheat plants can be regenerated, plant calli, plant clumps, and plant cells that are intact in plants or parts of plants, such as embryos, pollen, ovules, pericarp, seed, flowers, florets, heads, spikes, leaves, roots, root tips, anthers, and the like.

As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers, and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide.

As used herein, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, cDNA, single- and double-stranded RNA, and RNA that is a mixture of single- and double-stranded regions, hybrid molecules comprising DNA and RNA that may be single-stranded or, more typically, double-stranded, or triple-stranded regions, or a mixture of single- and double-stranded regions. The term "polynucleotide(s)" also embraces short nucleotides or fragments, often referred to as "oligonucleotides," that due to mutagenesis are not 100% identical but nevertheless code for the same amino acid sequence.

A "reduced or non-functional fragment," as is used herein, refers to a nucleic acid sequence that encodes a WPBF protein that has reduced biological activity as compared to the protein coding sequence of the whole nucleic acid sequence. In other words, it refers to a nucleic acid or fragment(s) thereof that substantially retains the capacity of encoding a WPBF polypeptide of the invention, but the encoded WPBF polypeptide has reduced activity.

The term "fragment," as used herein, refers to a polynucleotide sequence, (e.g, a PCR fragment) which is an isolated portion of the subject nucleic acid constructed artificially (e.g., by chemical synthesis) or by cleaving a natural product into multiple pieces, using restriction endonucleases or mechanical shearing, or a portion of a nucleic acid synthesized by PCR, DNA polymerase or any other polymerizing technique well known in the art, or expressed in a host cell by recombinant nucleic acid technology well known to one of skill in the art.

With reference to polynucleotides of the disclosure, the term "isolated polynucleotide" is sometimes used. This term, when applied to DNA, refers to a DNA molecule that is separated from sequences with which it is immediately contiguous (in the 5' and 3'directions) in the naturally occurring genome of the organism from which it was derived. For example, the "isolated polynucleotide" may comprise a PCR fragment. In another embodiment, the "isolated polynucleotide" may comprise a DNA molecule inserted into a vector, such as a plasmid or virus vector, or integrated into the genomic DNA of a prokaryote or eukaryote. An "isolated polynucleotide molecule" may also comprise a cDNA molecule.

As used herein, a single nucleotide polymorphism (SNP) is a single nucleotide base difference between two DNA according to nucleotide substitutions either as transitions (C/T or G/A) or transversions (C/G, A/T, C/A or T/G). Single base variants are considered to be SNPs as are single base insertions and deletions (in/dels) in the genome.

As used herein, Tolerase® G is a is a proline-specific digestive enzyme shown to be effective in helping digest gluten. Tolerase® G works on both low- and high-caloric meals.

As used herein, "transcription factor ("TF") activity" refers to the extent to which the TF activates the transcription of its target genes.

As used herein, a "transgenic plant" refers to a plant that contains a gene construct ("transgene") not found in a wild-type plant of the same species, variety or cultivar. A "transgene" as referred to herein has the normal meaning in the art of biotechnology and includes a genetic sequence that has been produced or altered by recombinant DNA or RNA technology and which has been introduced into the plant cell. The transgene may include genetic sequences derived from a plant cell. Typically, the transgene has been introduced into the plant by human manipulation such as, for example, by transformation but any method can be used as one of skill in the art recognizes.

As used herein, a "modified WPBF gene" includes modification of the WPBF gene through non-transgenic mutations or transgenes or genomic editing or combinations thereof.

As used herein, a "WPBF derivative" refers to a WPBF protein/peptide/polypeptide sequence that possesses biological activity that is substantially reduced as compared to the biological activity of the whole WPBF protein/peptide/polypeptide sequence. In other words, it refers to a polypeptide of a modified WPBF protein that has reduced WPBF activity. The term "WPBF derivative" encompasses the "fragments" or "chemical derivatives" of a modified WPBF protein/peptide.

A wheat plant is defined herein as any plant of a species of the genus Triticum, which species is commercially cultivated, including, for example, Triticum aestivum L. ssp. aestivum (common or bread wheat), other subspecies of Triticum aestivum, Triticum turgidum L. ssp. durum (durum wheat, also known as macaroni or pasta wheat), Triticum monococcum L. ssp. monococcum (cultivated einkorn or small spelt), Triticum timopheevi ssp. timopheevi, Triticum turgidum L. ssp. dicoccon (cultivated emmer), and other subspecies of Triticum turgidum (Feldman). The wheat may be hexaploid wheat having an AABBDD type genome, or tetraploid wheat having an AABB type genome. Since genetic variation in wheat transferred to certain related species, including rye and barley by hybridization, the disclosure also includes the hybrid species thus formed, including triticale that is a hybrid between bread wheat and rye. In one embodiment, the wheat plant is of the species Triticum aestivum, and preferably of the subspecies aestivum. Alternatively, since mutations or transgenes can be readily transferred from Triticum aestivum to durum wheat, the wheat is preferably Triticum turgidum L. ssp. durum.

In another embodiment, the disclosure describes wheat plants exhibiting reduced gluten grains as compared to wild type wheat plants without the inclusion of foreign nucleic acids in the wheat plant genome. In one embodiment, the disclosure relates to non-transgenic mutations in one or more WPBF genes.

In still another embodiment, the disclosure relates to a series of independent human-induced non-transgenic mutations in one or more WPBF genes; wheat plants having one or more of these mutations in at least one WPBF gene thereof; and a method of creating and identifying similar and/or additional mutations in at least one WPBF gene of wheat.

In yet another embodiment, the disclosure relates to a transgenic wheat plant with a transgene that reduces expression of the WPBF gene and/or activity of the WPBF protein, wherein said transgene contributed to grain having reduced gluten as compared to grain from a wild type plant.

In still another embodiment, the disclosure relates to wheat plant having a modified WPBF gene, wherein the WPBF gene is modified by genomic editing, and further wherein said modification contributes to grain having reduced gluten as compared to grain from a wild type plant.

I. Wheat Prolamin-Box Binding Factor

Wheat prolamin-box binding factor (WPBF), a DNA binding with one finger (DoF) transcription factor, functions as an activator of prolamin gene expression during seed development; WPBF is an activator of storage protein genes. During central endosperm development, the transcription of the genes encoding storage proteins is temporally and spatially regulated through a pathway that requires transcription factors that bind to specific DNA motifs, including the endosperm box (EB) and the ACAA motif. The EB consists of two distinct protein binding sites: the GCN4-like motif and the prolamin box.

The Dof proteins are plant transcription factors that have a highly conserved DNA-binding domain. The Dof domain, which is composed of about 50-60 amino acid residues, is similar to the Cys2/Cys2 zinc finger DNA-binding domain of GATA1 and steroid hormone receptors, but has a longer putative loop as compared to zinc-finger domains.

In one embodiment, the disclosure relates to reducing expression of the WPBF gene and/or reducing activity of the WPBF protein. In one embodiment, the disclosure relates to plants with reduced expression of the WPBF gene and/or reducing activity of the WPBF protein. In one embodiment, reducing expression of the WPBF gene or reducing activity of the WPBF protein can be accomplished by non-transgenic mutations, transgenes, or genomic editing.

In one embodiment, the disclosure relates to modifying the WPBF gene through non-transgenic mutations, or transgenes or genomic editing.

A. Glutenins

Wheat gluten is a binary mixture of gliadin and glutenin. The glutenins, which include both high molecular weight (HMW) glutenin subunits and low molecular weight (LMW) glutenin subunits, comprise an economically important class of wheat seed storage proteins. The apparent molecular weights of the individual HMW glutenin polypeptides or subunits range from 90 to 200 kDa. These subunits crosslink by disulfide bonds among themselves and with LMW glutenin polypeptides to form polymers exceeding one million daltons in molecular weight. HMW glutenins constitute 8-10%, while LMW glutenins constitute 15-20% of the total endosperm protein. Both HMW and LMW glutenin proteins play important functional roles in determining the end-uses of wheat flour.

In wheat, HMW glutenins are encoded at the Glu-1 loci on the long arms of the group 1 chromosomes. Each locus consists of two separate genes, encoding an x-type and a y-type subunit, respectively. Both the quantity and identity of specific HMW glutenin alleles contribute to the differences in bread-making quality of various cultivars. For instance, deletion of glutenin genes results in a decrease in the overall levels of HMW glutenins, which results in decreases in bread-making quality.

In one aspect, the disclosure relates to modified plants that have an increased amount of high molecular weight glutenins as compared to wild type plants. In one embodiment, the disclosure relates to compositions and methods for increasing the amount of high molecular weight glutenins in grains. In another embodiment, the disclosure relates to modification of the wheat prolamin box binding factor gene to increase the amount of high molecular weight glutenins in grains. In still another embodiment, the disclosure relates to one or more mutations in the WPBF gene or modifications of the WPBF gene to increase the amount of high molecular weight glutenins in grains.

In one embodiment, the disclosure relates to plants, including barley, rye, and wheat, with one or more mutations in the WPBF gene or modifications of the WPBF gene that have about 5%, or 10%, or 15%, or 20%, or 25%, or 30%, or 40%, or 50%, or 60%, or 70%, or 80%, or 85%, or 90%, or 95% or more high molecular weight glutenins as compared to grains in wild type plants.

In one embodiment, the disclosure relates to plants, including barley, rye, and wheat, with one or more mutations in the WPBF gene or modifications of the WPBF gene that have about from about 5% to about 20%, or from about 20% to about 40%, or from about 40% to about 60%, or from about 60% to about 80%, or from 80% to about 95% more high molecular weight glutenins as compared to grains in wild type plants.

In one aspect, the disclosure relates to modified plants that have a decreased amount of low molecular weight glutenins as compared to wild type plants. In one embodiment, the disclosure relates to compositions and methods for decreasing the amount of low molecular weight glutenins in grains. In another embodiment, the disclosure relates to modification of the wheat prolamin box binding factor gene to decrease the amount of low molecular weight glutenins in grains as compared to wild type grains. In still another embodiment, the disclosure relates to one or more mutations in the WPBF gene or modifications of the WPBF gene to decrease the amount of low molecular weight glutenins in grains as compared to wild type grains.

In one embodiment, the disclosure relates to plants, including barley, rye, and wheat, with one or more mutations in the WPBF gene or modifications of the WPBF gene that have about less than 5%, or less than 10%, or less than 15%, or less than 20%, or less than 25%, or less than 30%, or less than 40%, or less than 50%, or less than 60%, or less than 70%, or less than 80%, or less than 85%, or less than 90%, or less than 95% of the amount of low molecular weight glutenins found in wild type grains.

In one embodiment, the disclosure relates to plants, including barley, rye, and wheat, with one or more mutations in the WPBF gene or modifications of the WPBF gene that have about from about 5% to about 20%, or from about 20% to about 40%, or from about 40% to about 60%, or from about 60% to about 80%, or from 80% to about 95% less low molecular weight glutenins as compared to grains in wild type plants.

B. Gliadin

Gliadin is the alcohol-soluble protein fraction of wheat gluten. Gliadins are typically rich in glutamine and proline, particularly in the N-terminal part. For example, the first 100 amino acids of alpha- and gamma-gliadins contain about 35% and about 20% of glutamine and proline residues, respectively.

In one aspect of the disclosure, modified plants are provided that differ from their naturally occurring counterparts by having reduced amounts of gliadins as compared to wild type plants. In one embodiment, the disclosure relates to compositions and methods for decreasing the amount of gliadins in grains. In another embodiment, the disclosure relates to modification of the WPBF gene to decrease the amount of gliadins in grains as compared to wild type grains. In still another embodiment, the disclosure relates to one or more mutations in the WPBF gene to decrease the amount of gliadins in grains as compared to wild type grains.

In one embodiment, the disclosure relates to plants, including barley, rye, and wheat, with one or more mutations in the WPBF gene or modifications of the WPBF gene that have about less than 5%, or less than 10%, or less than 15%, or less than 20%, or less than 25%, or less than 30% or less than 40% or less than 50%, or less than 60%, or less than 70%, or less than 80%, or less than 85%, or less than 90%, or less than 95% of the amount of gliadins in wild type grains.

In one embodiment, the disclosure relates to plants, including barley, rye, and wheat, with one or more mutations in the WPBF gene or modifications of the WPBF gene that have about from about 5% to about 20%, or from about 20% to about 40%, or from about 40% to about 60%, or from about 60% to about 80%, or from 80% to about 95% less gliadins as compared to grains in wild type plants.

II Mutations of the WPBF Gene

A. WPBF Gene

In one embodiment, the disclosure relates to one or more non-transgenic mutations in the WPBF gene. In another embodiment, the disclosure relates to one or more mutations in the WPBF gene. In one embodiment, the disclosure relates to multiple non-transgenic mutations in the WPBF gene including but not limited to 1, 2, 3, 4, 5, 6, 7, 8, 9, 10, and greater than 10 mutations.

In another embodiment, the WPBF gene may contain one or more non-transgenic mutations recited in Tables 1-3 and corresponding mutations in homoeologues and combinations thereof.

In another embodiment, the disclosure relates to corresponding mutations to the one or more non-transgenic mutations disclosed herein in the WPBF gene in a corresponding homoeologue. By way of example, an identified mutation in the WPBF gene of the A genome may be a beneficial mutation in the WPBF gene of the B and/or D genome. One of ordinary skill in the art will understand that the mutation in the homoeologue may not be in the exact same location.

One of ordinary skill in the art understands that there may be natural variation in the genetic sequences of the WPBF genes in different wheat varieties.

The inventors have determined that to achieve reduced gluten in grains from plants, mutations that reduce WPBF gene function are desirable. Preferred mutations include missense and nonsense changes, including mutations that prematurely truncate the translation of one or more WPBF proteins from messenger RNA, such as those mutations that create a stop codon within the coding region of an WPBF messenger RNA. Such mutations include insertions, repeat sequences, splice junction mutations, modified open reading frames (ORFs) and point mutations.

In still another embodiment, one or more mutations are in the WPBF gene of the A genome. In another embodiment, one or more mutations are in the WPBF gene of the B genome. In still another embodiment, one or more mutations are in the WPBF gene of the D genome. In yet another embodiment, one or more mutations are in the WPBF genes of the A and B genomes. In still another embodiment, one or more mutations are in the WPBF genes of the A and D genomes. In another embodiment, one or more mutations are in the WPBF genes of the B and D genomes. In yet another embodiment, one or more mutations are in the WPBF genes of the A, B, and D genomes.

1. A Genome

In one embodiment, the disclosure relates to multiple non-transgenic mutations in the WPBF gene of the A genome including but not limited to 1, 2, 3, 4, 5, 6, 7, 8, 9, 10, and greater than 10 mutations. In one embodiment, one or more non-transgenic mutations are in both alleles of the WPBF gene in the A genome. In another embodiment, the non-transgenic mutations are identical in both alleles of the WPBF gene of the A genome. In one embodiment, the mutations are homozygous.

In yet another embodiment, one or mutations are in the DoF region in the WPBF gene of the A genome. In still another embodiment, one or more mutations are in the DoF region in the WPBF gene that alter DNA binding of WPBF protein. In yet another embodiment, one or more mutations are in the DoF region in the WPBF gene that do not alter DNA binding but alter function of WPBF in another manner.

The following mutations identified in Tables 1-3 are exemplary of the mutations created and identified according to various embodiments disclosed herein. They are offered by way of illustration, not limitation. It is to be understood that the mutations below are merely exemplary and that similar mutations are also contemplated.

Table 1 provides a list of representative mutations in the WPBF gene in the A genome. One exemplary mutation is G41A, resulting in a change from guanine to adenine at nucleotide position 41 identified according to its position in the sequence of SEQ ID NO: 2. This mutation results in a change from glycine to aspartic acid at amino acid position 14 identified according to its position in the expressed protein (SEQ ID NO: 3). One of skill in the art will understand that for certain alleles the nucleotide acid position may vary slightly due to upstream un-translated regions. All nucleic acid changes that result in amino acid changes recited in Tables 1-3 are encompassed herein.

TABLE 1

Representative mutations in the WPBF gene in the A genome

| Wheat | Gene | Mutation | Nucleotide |
|---|---|---|---|
| Kronos | WPBF-A | M1I | G3A |
| Kronos | WPBF-A | E3K | G7A |
| Kronos | WPBF-A | V4M | G10A |
| Kronos | WPBF-A | P6S | C16T |
| Kronos | WPBF-A | G14S | G40A |
| Kronos | WPBF-A | G14D | G41A |
| Kronos | WPBF-A | A17T | G49A |
| Kronos | WPBF-A | E19K | G55A |
| Kronos | WPBF-A | A20T | G58A |
| Kronos | WPBF-A | A22T | G64A |
| Kronos | WPBF-A | A23T | G67A |
| Kronos | WPBF-A | A24T | G70A |
| Kronos | WPBF-A | P28S | C82T |
| Kronos | WPBF-A | P30S | C88T |
| Kronos | WPBF-A | P32S | C94T |
| Kronos | WPBF-A | E33K | G97A |
| Kronos | WPBF-A | Q34L | A101T |
| Kronos | WPBF-A | V36M | G106A |
| Kronos | WPBF-A | E37K | G109A |
| Kronos | WPBF-A | P39S | C115T |
| Kronos | WPBF-A | G44D | G131A |
| Kronos | WPBF-A | T46I | C137T |
| Kronos | WPBF-A | C49Y | G146A |
| Kronos | WPBF-A | M56I | G168A |
| Kronos | WPBF-A | S57F | C170T |
| Kronos | WPBF-A | R60L | G179T |
| Kronos | WPBF-A | W70* | G210A |
| Kronos | WPBF-A | G73D | G218A |
| Kronos | WPBF-A | G74D | G221A |
| Kronos | WPBF-A | S75F | C224T |
| Kronos | WPBF-A | L76F | C226T |
| Kronos | WPBF-A | P80S | C238T |
| Kronos | WPBF-A | P80L | C239T |
| Kronos | WPBF-A | G84S | G250A |
| Kronos | WPBF-A | G84D | G251A |
| Kronos | WPBF-A | P88L | C263T |
| Kronos | WPBF-A | P91S | C271T |
| Kronos | WPBF-A | G92E | G275A |
| Kronos | WPBF-A | A96V | C287T |
| Kronos | WPBF-A | L99F | C295T |
| Kronos | WPBF-A | S103F | C308T |
| Kronos | WPBF-A | E106K | G316A |
| Kronos | WPBF-A | P113S | C337T |
| Kronos | WPBF-A | P113L | C338T |
| Kronos | WPBF-A | T115I | C344T |
| Kronos | WPBF-A | V124I | G370A |
| Kronos | WPBF-A | L125F | C373T |
| Kronos | WPBF-A | P126S | C376T |
| Kronos | WPBF-A | A131V | C392T |
| Kronos | WPBF-A | S140F | C4219T |

TABLE 1-continued

Representative mutations in the WPBF gene in the A genome

| Wheat | Gene | Mutation | Nucleotide |
|---|---|---|---|
| Kronos | WPBF-A | A143V | C428T |
| Kronos | WPBF-A | A143V | C428T |
| Kronos | WPBF-A | G145E | G434A |
| Kronos | WPBF-A | S146L | C437T |
| Kronos | WPBF-A | S148L | C443T |
| Kronos | WPBF-A | A153T | G457A |
| Kronos | WPBF-A | S157F | C470T |
| Kronos | WPBF-A | P158S | C472T |
| Kronos | WPBF-A | G160E | G479A |
| Kronos | WPBF-A | T161M | C482T |
| Kronos | WPBF-A | T162M | C485T |
| Kronos | WPBF-A | R169K | G506A |
| Kronos | WPBF-A | G171D | G512A |
| Kronos | WPBF-A | G174R | G520A |
| Kronos | WPBF-A | L175F | C523T |
| Kronos | WPBF-A | G178D | G533A |
| Kronos | WPBF-A | G185D | G554A |
| Kronos | WPBF-A | G189D | G566A |
| Kronos | WPBF-A | P203S | C607T |
| Kronos | WPBF-A | P203L | C608T |
| Kronos | WPBF-A | P204S | C610T |
| Kronos | WPBF-A | G209D | G626A |
| Kronos | WPBF-A | P211S | C631T |
| Kronos | WPBF-A | M214I | G642A |
| Kronos | WPBF-A | G226E | G677A |
| Kronos | WPBF-A | A229T | G685A |
| Kronos | WPBF-A | T231I | C692T |
| Kronos | WPBF-A | G237R | G709A |
| Kronos | WPBF-A | G252R | G754A |
| Kronos | WPBF-A | W255* | G764A |
| Kronos | WPBF-A | G262D | G785A |
| Kronos | WPBF-A | G271S | G811A |
| Kronos | WPBF-A | H274Y | C820C |
| Kronos | WPBF-A | M283I | G849A |
| Kronos | WPBF-A | G284D | G851A |
| Express | WPBF-A | G18R | G52A |
| Express | WPBF-A | V36M | G106A |
| Express | WPBF-A | C66Y | G197A |
| Express | WPBF-A | P80L | C239T |
| Express | WPBF-A | G92R | G274A |
| Express | WPBF-A | S103F | C308T |
| Express | WPBF-A | V109I | G325A |
| Express | WPBF-A | G145E | G434A |

In one embodiment, the disclosure relates to a polynucleotide of the WPBF gene in the A genome with one or more non-transgenic mutations listed in Table 1 and corresponding to SEQ ID NO: 2. In another embodiment, the polynucleotide with one or more non-transgenic mutations listed in Table 1 has 85%, 86%, 87%, 88%, 89%, 90%, 91%, 92%, 93%, 94%, 95%, 96%, 97%, 98%, 99% or greater than 99% identity to SEQ ID NO: 2.

In still another embodiment, the polynucleotide with one or more non-transgenic mutation listed in Table 1 codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity to SEQ ID NO: 3.

```
SEQ ID NO. 1:
Wheat Prolamin Box Binding Factor (WPBF) A genome
(the nucleotide sequence may differ very slightly
in different wheat cultivars-different alleles):
CTGGCTTGCTCATTTTGCGGTAGTGTTTAAACATCGGCTAGCCTTACGGG

TATAAAAAGGTGGGCAACTTCACCCTATCCCATAGCACTAGACCAAAGAA

CACCTATACTCCATACTACCCTTCGTTCACCTGGTGAGCTTCTTCTTCCT

TTGATCTATATCACTTACTATTTCTCCCTTGTCCAGCTTCTTCTTCTTCC
```

-continued

TCGTGCATGCGACTTTTTCTAGATAATATCCCGCACTATCGCTCGCCGCA
AGATGTGCTAGCTAGCGATCTTCACTTTAATACCTGTTGTAGATCTAACC
ACGGGCTATTCCAAAAAATATTTGTCTTGTTTGCGTGTTCCTGTGTACAT
GCACGTATCTAGATCTTGATTTTGAAGAATTCATAATTAATTCATGACCT
ACCTTGTTTGGTTTGTGTAATTTTGATGTTGTCGTATCAATTTTAGCAAA
CCACTCGTAGCTAGAACAATAGAGGGGGCGATCGTATGTTTCTGTTTTGA
AAAGGGGATATTTCCAGGCTCTGCATCGGTTCATGCACACAGCCGTTACC
ACATTCAATAGGCACTGATCCATGGATGCATGCCAGATTTACTAGTTTTG
TATACAAAGTTTTACTTTTTTGCTTTGATTTATGAAAAGTTGGATCAGAT
TTTGCAGTTCTCTTTTATCCATGTTGGATTCACTACTTTGTACCCAAGAT
TTTATTTATTTTGTCTTGGTTTCTTACCTGCCTGGTTAGTAACTAGGAGA
TCCTGGGATTAGACTTTCAAGGAATCCTAATACTAGTGAGTATAGGGAAA
GGAAGCTTATTTTTAAGCTGCCCAAAAGAATGGGCGCTTAGAGTTGTAGT
TGATTAATTGAATCTGTTCTGTGGATTTGAGAATTTCAGACCTGATTCTA
CATGACATTTTGAGTTAACCAATGATTCTACATGTCTCACTCCTTGGGAT
TAACAATTTAACTTTATTTAATTCGATATGTGTGTACACATGTGTTGCAG
ATGGAGGAAGTGTTTCCGTCAAACTCCAAGAGCAAGGCCGGTCAGATGGC
GGGGGAGGCGACAGCGGCGGCGGAGAAGAAGCCTCGGCCGAAGCCAGAGC
AGAAGGTGGAATGCCCTCGGTGCAAGTCTGGCAACACCAAGTTCTGCTAC
TACAACAACTATAGTATGTCTCAGCCCCGCTACTTCTGCAAGGCCTGCCG
CCGCTACTGGACCCATGGTGGCTCCCTCCGCAACGTCCCCATCGGTGGCG
GCTGCCGCAAGCCCAAGCGCCCGGGGACCTCCGACGCCCACAAGCTCGGC
GTGGCCTCCTCGTCAGAACCCACGGTTGTCATGCCGCCCTCGACCTGCAC
AGGGATGAACTTTGCCAACGTCCTCCCAACATTTATGTCTGCTGGTTTTG
AGATTCCAAGCAGCCTTTCCCTGACTGCCTTTGGGTCATCGTCATCGTCC
AACACGGCGGCAGTGATGTCCCCTGGTGGGACGACGTCATTTCTAGACGT
GTTGAGAGGGGGCGCAGGAGGGCTTCTTGATGGCAGCCTCAGTCAGAACA
ATGGCTACTACTATGGTGGGCCTGCCACTGGATCAGGCATTGGGATGCTG
ATGACGCCGCCAGTGGCGTCATTTGGCATTCCAGGTCCGATGCAGCAACA
TGGTGATCTCGTGGTTGGTGGAAATGGAATAGGTGCTGCAACTGCTTCAA

TATTTCAGGGGGGCACTGGCGAGGAAGGAGATGATGGTACGGGGGGCGTG

ATGGGGCTCCAATGGCAGCCACAGGTTGGCAATGGTGGAGGTGCTGGTGT

TGTATCAGGAGGCGTGCATCACCTTGGGACTGGGAACAATGTGACGATGG

GCAACAACAATATACACAACAACAACAATAACAACAGTGGGGGTGATGAC

AACAATGGTGCGTCATCGAGGGATTGCTACTGGATCAACAATGGAGGATC

GAACCCATGGCAGAGCCTCCTCAACAACAGCTCCCTGATGTAAGTGCAAT

AAGAAAATGGGAAATGGAGGTCAT

SEQ ID NO. 2
Wheat Prolamin Box Binding Factor (WPBF) A coding region:
ATGGAGGAAGTGTTTCCGTCAAACTCCAAGAGCAAGGCCGGTCAGATGGC

GGGGGAGGCGACAGCGGCGGCGGAGAAGAAGCCTCGGCCGAAGCCAGAGC

-continued

AGAAGGTGGAATGCCCTCGGTGCAAGTCTGGCAACACCAAGTTCTGCTAC

TACAACAACTATAGTATGTCTCAGCCCCGCTACTTCTGCAAGGCCTGCCG

CCGCTACTGGACCCATGGTGGCTCCCTCCGCAACGTCCCCATCGGTGGCG

GCTGCCGCAAGCCCAAGCGCCCGGGGACCTCCGACGCCCACAAGCTCGGC

GTGGCCTCCTCGTCAGAACCCACGGTTGTCATGCCGCCCTCGACCTGCAC

AGGGATGAACTTTGCCAACGTCCTCCCAACATTTATGTCTGCTGGTTTTG

AGATTCCAAGCAGCCTTTCCCTGACTGCCTTTGGGTCATCGTCATCGTCC

AACACGGCGGCAGTGATGTCCCCTGGTGGGACGACGTCATTTCTAGACGT

GTTGAGAGGGGGCGCAGGAGGGCTTCTTGATGGCAGCCTCAGTCAGAACA

ATGGCTACTACTATGGTGGGCCTGCCACTGGATCAGGCATTGGGATGCTG

ATGACGCCGCCAGTGGCGTCATTTGGCATTCCAGGTCCGATGCAGCAACA

TGGTGATCTCGTGGTTGGTGGAAATGGAATAGGTGCTGCAACTGCTTCAA

TATTTCAGGGGGGCACTGGCGAGGAAGGAGATGATGGTACGGGGGGCGTG

ATGGGGCTCCAATGGCAGCCACAGGTTGGCAATGGTGGAGGTGCTGGTGT
TGTATCAGGAGGCGTGCATCACCTTGGGACTGGGAACAATGTGACGATGG
GCAACAACAATATACACAACAACAACAATAACAACAGTGGGGGTGATGAC
AACAATGGTGCGTCATCGAGGGATTGCTACTGGATCAACAATGGAGGATC
GAACCCATGGCAGAGCCTCCTCAACAACAGCTCCCTGATG

SEQ ID NO. 3:
WPBF-A amino acid sequence:
MEEVFPSNSKSKAGQMAGEATAAAEKKPRPKPEQKVECPRCKSGNTKFCY
YNNYSMSQPRYFCKACRRYWTHGGSLRNVPIGGGCRKPKRPGTSDAHKLG
VASSSEPTVVMPPSTCTGMNFANVLPTFMSAGFEIPSSLSLTAFGSSSSS
NTAAVMSPGGTTSFLDVLRGGAGGLLDGSLSQNNGYYYGGPATGSGIGML
MTPPVASFGIPGPMQQHGDLVVGGNGIGAATASIFQGGTGEEGDDGTGGV
MGLQWQPQVGNGGGAGVVSGGVHHLGTGNNVTMGNNNIHNNNNNNSGGDD
NNGASSRDCYWINNGGSNPWQSLLNNSSLM

2. B Genome

In one embodiment, the disclosure relates to multiple non-transgenic mutations in the WPBF gene of the B genome including but not limited to 1, 2, 3, 4, 5, 6, 7, 8, 9, 10, and greater than 10 mutations. In one embodiment, one or more non-transgenic mutations are in both alleles of the WPBF gene in the B genome. In another embodiment, the non-transgenic mutations are identical in both alleles of the WPBF gene of the B genome. In still another embodiment, the mutations are homozygous.

In yet another embodiment, one or mutations are in the DoF region in the WPBF gene of the B genome. In still another embodiment, one or more mutations are in the DoF region in the WPBF gene that alter DNA binding of WPBF protein. In yet another embodiment, one or more mutations are in the DoF region in the WPBF gene that do not alter DNA binding but alter function of WPBF in another manner.

Table 2 provides a representative list of mutations in the WPBF gene of the B genome, of wheat plants, Kronos and Express. Nucleotide and amino acid changes are identified according to their positions in SEQ ID NOs: 5 and 6, respectively. The "*" indicates a stop codon.

TABLE 2

Representative mutations in the WPBF gene of the B genome

| Wheat | Gene | Mutation | Nucleotide |
|---|---|---|---|
| Kronos | WPBF-B | V4E | T11A |
| Kronos | WPBF-B | S9F | C26T |
| Kronos | WPBF-B | A13T | G37A |
| Kronos | WPBF-B | M16I | G48A |
| Kronos | WPBF-B | A17T | G49A |
| Kronos | WPBF-B | G18R | G52A |
| Kronos | WPBF-B | E19K | G55A |
| Kronos | WPBF-B | A20T | G58A |
| Kronos | WPBF-B | A22T | G64A |
| Kronos | WPBF-B | A23T | G67A |
| Kronos | WPBF-B | A24T | G70A |
| Kronos | WPBF-B | A24V | C71T |
| Kronos | WPBF-B | P28L | C83T |
| Kronos | WPBF-B | P30S | C88T |
| Kronos | WPBF-B | P32L | C95T |
| Kronos | WPBF-B | E37K | G109A |
| Kronos | WPBF-B | C38Y | G113A |
| Kronos | WPBF-B | P39S | C115T |
| Kronos | WPBF-B | S43F | C128T |
| Kronos | WPBF-B | T46I | C137T |
| Kronos | WPBF-B | Q58* | C172T |
| Kronos | WPBF-B | P59S | C175T |
| Kronos | WPBF-B | T71I | C212T |
| Kronos | WPBF-B | G73S | G217A |
| Kronos | WPBF-B | G73D | G218A |
| Kronos | WPBF-B | G74R | G221A |
| Kronos | WPBF-B | R77H | G230A |
| Kronos | WPBF-B | P80S | C238T |
| Kronos | WPBF-B | P80L | C239T |
| Kronos | WPBF-B | G83S | G247A |
| Kronos | WPBF-B | P88L | C263T |
| Kronos | WPBF-B | G92E | G275A |
| Kronos | WPBF-B | S94F | C281T |
| Kronos | WPBF-B | A96V | C287T |
| Kronos | WPBF-B | A102T | G304A |
| Kronos | WPBF-B | A102V | C305T |
| Kronos | WPBF-B | S105L | C314T |
| Kronos | WPBF-B | E106K | G316A |
| Kronos | WPBF-B | A109T | G325A |
| Kronos | WPBF-B | A109V | C326T |
| Kronos | WPBF-B | M111I | G333A |
| Kronos | WPBF-B | G118E | G353A |
| Kronos | WPBF-B | A122V | C365T |
| Kronos | WPBF-B | L125F | C373T |
| Kronos | WPBF-B | P126S | C376T |
| Kronos | WPBF-B | P126L | C377T |
| Kronos | WPBF-B | M129I | G387A |
| Kronos | WPBF-B | P136S | C406T |
| Kronos | WPBF-B | P136L | C407T |
| Kronos | WPBF-B | L139F | C415T |
| Kronos | WPBF-B | S140F | C419T |
| Kronos | WPBF-B | T142I | C425T |
| Kronos | WPBF-B | T143I | C428T |
| Kronos | WPBF-B | G145E | G434A |
| Kronos | WPBF-B | S147L | C440T |
| Kronos | WPBF-B | S150F | C449T |
| Kronos | WPBF-B | M156I | G468A |
| Kronos | WPBF-B | G159D | G476A |
| Kronos | WPBF-B | G160E | G479A |
| Kronos | WPBF-B | S163L | C488T |
| Kronos | WPBF-B | R169K | G506A |
| Kronos | WPBF-B | G171R | G511A |
| Kronos | WPBF-B | G174E | G521A |
| Kronos | WPBF-B | L176F | C526T |
| Express | WPBF-B | E2K | G4A |
| Express | WPBF-B | E3K | G7A |
| Express | WPBF-B | E3D | A9T |
| Express | WPBF-B | A13T | G37A |
| Express | WPBF-B | G14D | G41A |
| Express | WPBF-B | M16I | G48A |
| Express | WPBF-B | A17T | G49A |
| Express | WPBF-B | G18R | G52A |
| Express | WPBF-B | G18E | G53A |
| Express | WPBF-B | A20T | G58A |
| Express | WPBF-B | A22T | G64A |
| Express | WPBF-B | A22V | G65A |
| Express | WPBF-B | A23T | G67A |
| Express | WPBF-B | A24T | G70A |
| Express | WPBF-B | P28L | C83T |
| Express | WPBF-B | P32T | C94A |
| Express | WPBF-B | P32S | C94T |
| Express | WPBF-B | E37K | G109A |
| Express | WPBF-B | C38Y | G113A |
| Express | WPBF-B | P39L | C116T |
| Express | WPBF-B | R40W | C118T |
| Express | WPBF-B | G44S | G130A |
| Express | WPBF-B | G44D | G131A |
| Express | WPBF-B | T46I | C137T |
| Express | WPBF-B | Q58* | C172T |
| Express | WPBF-B | P59S | C175T |
| Express | WPBF-B | P59L | C176T |
| Express | WPBF-B | R60C | C178T |
| Express | WPBF-B | R60H | G179A |
| Express | WPBF-B | C63Y | G188A |
| Express | WPBF-B | A65V | C194T |
| Express | WPBF-B | R68H | G203A |
| Express | WPBF-B | W70* | G209A |
| Express | WPBF-B | W70R | T208A |
| Express | WPBF-B | T71I | C212T |
| Express | WPBF-B | G73D | G218A |
| Express | WPBF-B | G73C | G217T |
| Express | WPBF-B | G73S | G217A |
| Express | WPBF-B | S75F | C224T |
| Express | WPBF-B | L76F | C226T |
| Express | WPBF-B | P80S | C238T |
| Express | WPBF-B | P80L | C239T |
| Express | WPBF-B | G82D | G245A |
| Express | WPBF-B | G83D | G248A |
| Express | WPBF-B | G84S | G250A |
| Express | WPBF-B | G84D | G251A |
| Express | WPBF-B | P88L | C263T |
| Express | WPBF-B | R90H | G269A |
| Express | WPBF-B | G92E | G275A |
| Express | WPBF-B | A96T | G286A |
| Express | WPBF-B | A96V | C287T |
| Express | WPBF-B | G100D | G299A |
| Express | WPBF-B | V101M | G301A |
| Express | WPBF-B | E106K | G316A |
| Express | WPBF-B | H107Y | C319T |
| Express | WPBF-B | A109T | G325A |
| Express | WPBF-B | P113S | C337T |
| Express | WPBF-B | P113L | C338T |
| Express | WPBF-B | T115I | C344T |
| Express | WPBF-B | G118E | G353A |
| Express | WPBF-B | A122S | G364T |
| Express | WPBF-B | V124I | G370A |
| Express | WPBF-B | L125F | C373T |
| Express | WPBF-B | P126S | C376T |
| Express | WPBF-B | P126L | C377T |
| Express | WPBF-B | A131T | G391A |
| Express | WPBF-B | G132S | G394A |
| Express | WPBF-B | G132D | G395A |
| Express | WPBF-B | P136S | C406T |
| Express | WPBF-B | G145E | G434A |
| Express | WPBF-B | A154T | G460A |
| Express | WPBF-B | M156I | G468A |
| Express | WPBF-B | P158S | C472A |
| Express | WPBF-B | G159D | G476A |
| Express | WPBF-B | T161M | C482T |
| Express | WPBF-B | D166N | G496A |
| Express | WPBF-B | G170R | G508A |
| Express | WPBF-B | G171R | G511A |
| Express | WPBF-B | G171E | G512A |
| Express | WPBF-B | G174R | G520A |
| Express | WPBF-B | G178D | G533A |
| Express | WPBF-B | Q182* | C544T |
| Express | WPBF-B | G185S | G553A |
| Express | WPBF-B | G185D | G554A |
| Express | WPBF-B | G189D | G566A |
| Express | WPBF-B | G190R | G568A |

In one embodiment, the disclosure relates to a polynucleotide of the WPBF gene in the B genome with one or more non-transgenic mutations listed in Table 2 and corresponding to SEQ ID NO: 5. In another embodiment, the polynucleotide with one or more non-transgenic mutations listed in Table 2 has 85%, 86%, 87%, 88%, 89%, 90%, 91%, 92%, 93%, 94%, 95%, 96%, 97%, 98%, 99% or greater than 99% identity to SEQ ID NO: 5.

In still another embodiment, the polynucleotide with one or more non-transgenic mutation listed in Table 2 codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity to SEQ ID NO: 6.

SEQ ID NO. 4 WPBF-B genome:
CTGGCTTGCTCATTTTGCGGTAGTGTTTAAACATTGGCTGGAATTACGGG
TATAAAAAGGAGGGCAACTTCACCCTATCCCATAGCACTAGACCAAACAA
CTCCTATACTCCATACTACCCTTCATTCACCTGGTGAGCTTCTTCTTTCT
TTGATTTCTATCACTTACTCTTTCTCCCTCGTCCAGCTTCTTCTTCTTCC
TCGTGCATGTGACTTTTGCTAGATAATCTCCCACATTATCGCTCAATGCA
AGCCGTGCTAGCTAGCTAGCGATCTAGCTAGCGATCTTCACTTTAATACC
CGTTGTAGATCTAACCATGGGCTATTCCAAAACATATTTCTCTTGTTTGC
GTGTTCGTGTGTACATGCATGCATCTAGATCTTGATTTTGAGGAATTCAT
AAGTAATTCCTGACCTACCTTGTTTGGTTTGTTTAATTTTGATGTTGTTG
TCTCAATTTTAGCAAATTGCTCGTAGCTAGAACAATAGAGGGGGCGGCCG
TATGTTTCCGTTTTGAAAAGGGGATATTTCCAGGCTCTGCATCGGTTGAT
GCACACAGCCGTTACCACATTCAATAGGCACTGATCCATGGATGCATGCT
ATATTTACAAGTTTTCTATAGAAATTTTTTTATTTATGAAAAATTGGAT
CGGTATAGTTCTTCTTTATCCATGTCGGATTCACTACTTTGTACCCAAGA
TTTTATTTATTTTGTCTCGGTTTCTTACATGTCTAGTTAGGTAACTAGGA
GAGCCTGGGATTAGGCTTTCAAGGAATCCTAATACTAGAGACTATGGGGA
GAGACAGCTTATTCTTTAAGCTGCGCAAAAGAATGGGCGCTTAGAGTTGT
AGTTGATAAATTGAATCTGTTGTATGGATTTGAGAATTTGAGACCTGATT
ATGCACTTATCATGAAATTTTGAGTTAACCAATGATTCTACATGTCTCAC
TCCTTAGGATTAACAATTTAACTTAATTTAATTCGATATGTGTGTACACA
TGTGTTGAAGATGGAGGAAGTGTTTCCGTCAAACTCCAAGAGCAAGGCTG
GTCAGATGGCGGGGGAGGCGACAGCGGCGGCGGAGAAGAAGCCTCGGCCG
AAGCCAGAGCAGAAGGTGGAATGCCCTCGGTGCAAGTCTGGCAACACCAA
GTTCTGCTACTACAACAACTATAGTATGTCTCAGCCCCGCTACTTCTGCA
AGGCCTGCCGCCGCTACTGGACCCATGGTGGGTCCCTCCGTAACGTCCCC
ATCGGTGGTGGCTGCCGCAAGCCCAAGCGCTCGGGGACCTCCGACGCCCA
CAAGCTCGGCGTGGCCTCCTCGTCGGAACACACGGCTGTCATGCCCCCCT
CGACCTGCACAGGGATAAACTTTGCCAATGTCCTCCCGACGTTTATGTCT
GCTGGTTTTGAGATTCCAAGAAGCCTTTCCCTGACCACCTTTGGGTCATC
GtcGTCGTCCAACACGACGGCTGTCATGTCCCCTGGTGGGACGACGTCAT
TTCTAGACGTGCTGAGAGGGGGAACAGGAGGGCTTCTTGATGGCAACCTC GGTCAGAACAATGGCTACTACTATGGTGGGTCTAGATCAGGCATTGGGAT
GCTGATGACGCCGCCAGCGGCGTCATTTGGCATTCCAGGTCCAATGCAGC
AGCATGGCGATCTCATGGTTGGTGGAAATGGAATAGGTGCCGCAACTGCT
TCAATATTTCAGGGGGGCACTGGTGAGGAAGGAGATGACGGCAAAGGGGC
CATGATGGGGCTCCAATGGCAGCCACATGTTGGTAATGGTGGAGGTGGTG
GTGTTGTATCAGGAGGCGTGCATCACCTTGGGACTGGGAACAATGTGACG
ATGGGCAACAACAACATAAACAACAATAACAATAATGGCAGCCACAGTGA
TGACAACACTGGTGGGTCATCGAGGGATTGCTACTGGATCAATAATGGAG
GATCGAACCCATGGCAAAGCCTCCTCAATAGCAGCTCCCTGATGTAAGTG
CAAGAAGAAAATGCGAAATGGAGATCAT SEQ ID NO. 5: WPBF-B coding sequence:
ATGGAGGAAGTGTTTCCGTCAAACTCCAAGAGCAAGGCTGGTCAGATGGC
GGGGGAGGCGACAGCGGCGGCGGAGAAGAAGCCTCGGCCGAAGCCAGAGC
AGAAGGTGGAATGCCCTCGGTGCAAGTCTGGCAACACCAAGTTCTGCTAC
TACAACAACTATAGTATGTCTCAGCCCCGCTACTTCTGCAAGGCCTGCCG
CCGCTACTGGACCCATGGTGGGTCCCTCCGTAACGTCCCCATCGGTGGTG
GCTGCCGCAAGCCCAAGCGCTCGGGGACCTCCGACGCCCACAAGCTCGGC
GTGGCCTCCTCGTCGGAACACACGGCTGTCATGCCCCCCTCGACCTGCAC
AGGGATAAACTTTGCCAATGTCCTCCCGACGTTTATGTCTGCTGGTTTTG
AGATTCCAAGAAGCCTTTCCCTGACCACCTTTGGGTCATCGtcGTCGTCC
AACACGACGGCTGTCATGTCCCCTGGTGGGACGACGTCATTTCTAGACGT
GCTGAGAGGGGAACAGGAGGGCTTCTTGATGGCAACCTCGGTCAGAACA
ATGGCTACTACTATGGTGGGTCTAGATCAGGCATTGGGATGCTGATGACG
CCGCCAGCGGCGTCATTTGGCATTCCAGGTCCAATGCAGCAGCATGGCGA
TCTCATGGTTGGTGGAAATGGAATAGGTGCCGCAACTGCTTCAATATTTC
AGGGGGGCACTGGTGAGGAAGGAGATGACGGCAAAGGGGCCATGATGGGG
CTCCAATGGCAGCCACATGTTGGTAATGGTGGAGGTGGTGGTGTTGTATC
AGGAGGCGTGCATCACCTTGGGACTGGGAACAATGTGACGATGGGCAACA
ACAACATAAACAACAATAACAATAATGGCAGCCACAGTGATGACAACACT
GGTGGGTCATCGAGGGATTGCTACTGGATCAATAATGGAGGATCGAACCC
ATGGCAAAGCCTCCTCAATAGCAGCTCCCTGATG SEQ ID NO. 6 WPBF B amino acid sequence:
MEEVFPSNSKSKAGQMAGEATAAAEKKPRPKPEQKVECPRCKSGNTKFCY
YNNYSMSQPRYFCKACRRYWTHGGSLRNVPIGGGCRKPKRSGTSDAHKLG
VASSSEHTAVMPPSTCTGINFANVLPTFMSAGFEIPRSLSLTTFGSSSSS
NTTAVMSPGGTTSFLDVLRGGTGGLLDGNLGQNNGYYYGGSRSGIGMLMT
PPAASFGIPGPMQQHGDLMVGGNGIGAATASIFQGGTGEEGDDGKGAMMG
LQWQPHVGNGGGGGVVSGGVHHLGTGNNVTMGNNNINNNNNNGSHSDDNT
GGSSRDCYWINNGGSNPWQSLLNSSSLM 3. D Genome In one embodiment, the disclosure relates to multiple non-transgenic mutations in the WPBF gene of the D genome including but not limited to 1, 2, 3, 4, 5, 6, 7, 8, 9, 10, and greater than 10 mutations. In one embodiment, one or more non-transgenic mutations are in both alleles of the WPBF gene in the D genome. In another embodiment, the non-transgenic mutations are identical in both alleles of the WPBF gene of the D genome.

Table 3 provides representative examples of mutations created and identified in the WPBF gene in the D genome of wheat plants, Express. Nucleotide and amino acid changes are identified according to their positions in SEQ ID NOs: 8 and 9, respectively.

TABLE 3

Representative list of mutations in the WPBF gene of the D genome

| Wheat | Gene | Mutation | Nucleotide |
|---|---|---|---|
| Express | WPBF-D | E2K | G4A |
| Express | WPBF-D | E3K | G7A |
| Express | WPBF-D | S7L | C20T |
| Express | WPBF-D | A13T | G37A |
| Express | WPBF-D | A13V | C38T |
| Express | WPBF-D | A17T | G49A |
| Express | WPBF-D | E19K | G55A |
| Express | WPBF-D | A20T | G58A |
| Express | WPBF-D | A22T | G64A |
| Express | WPBF-D | A24T | G70A |
| Express | WPBF-D | P28S | C82T |
| Express | WPBF-D | E37K | G109A |
| Express | WPBF-D | C38Y | G113A |
| Express | WPBF-D | P39S | C115T |
| Express | WPBF-D | P39L | C116T |
| Express | WPBF-D | C41S | T121A |
| Express | WPBF-D | G44D | G131A |
| Express | WPBF-D | C49Y | G146A |
| Express | WPBF-D | R60C | C1278T |
| Express | WPBF-D | C63Y | G188A |
| Express | WPBF-D | A65T | G193A |
| Express | WPBF-D | W70* | G209A |
| Express | WPBF-D | G73D | G218A |
| Express | WPBF-D | G74D | G221A |
| Express | WPBF-D | S75F | C224T |
| Express | WPBF-D | P80S | c238T |
| Express | WPBF-D | P80L | C239T |
| Express | WPBF-D | G82D | G245A |
| Express | WPBF-D | G83S | G247A |
| Express | WPBF-D | P88L | C263T |
| Express | WPBF-D | G92E | G275A |
| Express | WPBF-D | S94F | C281T |
| Express | WPBF-D | A96V | C287T |
| Express | WPBF-D | V101M | G301A |
| Express | WPBF-D | A102V | C305T |
| Express | WPBF-D | P105S | C313T |
| Express | WPBF-D | E106K | G316A |
| Express | WPBF-D | P107S | C319T |
| Express | WPBF-D | P107L | C320T |
| Express | WPBF-D | V111M | G331A |
| Express | WPBF-D | P112S | C334T |
| Express | WPBF-D | P113L | C338T |
| Express | WPBF-D | T115I | C344T |
| Express | WPBF-D | G118E | G353A |
| Express | WPBF-D | M119I | G357T |
| Express | WPBF-D | A122V | C365T |
| Express | WPBF-D | M129I | G387A |
| Express | WPBF-D | G132D | G395A |
| Express | WPBF-D | P136S | C406T |
| Express | WPBF-D | P136L | C407T |
| Express | WPBF-D | A143V | C428T |
| Express | WPBF-D | G145R | G433A |
| Express | WPBF-D | S150F | C449T |
| Express | WPBF-D | A153T | G457A |
| Express | WPBF-D | A154T | G460A |
| Express | WPBF-D | S157F | C470T |
| Express | WPBF-D | P158S | C472T |
| Express | WPBF-D | P158L | C473T |
| Express | WPBF-D | G159D | G476A |
| Express | WPBF-D | T161P | A481C |
| Express | WPBF-D | R169K | G506A |
| Express | WPBF-D | G170R | G508A |
| Express | WPBF-D | G171S | G511A |
| Express | WPBF-D | G171D | G512A |

TABLE 3-continued

Representative list of mutations in the WPBF gene of the D genome

| Wheat | Gene | Mutation | Nucleotide |
|---|---|---|---|
| Express | WPBF-D | G174R | G520A |
| Express | WPBF-D | G174E | G521A |
| Express | WPBF-D | L175F | C523T |
| Express | WPBF-D | G185S | G553A |
| Express | WPBF-D | G189D | G566A |
| Express | WPBF-D | P191S | C571T |
| Express | WPBF-D | A192V | C575T |
| Express | WPBF-D | G194E | G581A |
| Express | WPBF-D | G196D | G587A |
| Express | WPBF-D | G198E | G593A |
| Express | WPBF-D | P203S | C607T |
| Express | WPBF-D | P204S | C610T |
| Express | WPBF-D | A205T | G613A |
| Express | WPBF-D | V206M | G616A |
| Express | WPBF-D | G209S | G625A |
| Express | WPBF-D | G209D | G626A |
| Express | WPBF-D | V212I | G634A |
| Express | WPBF-D | M214I | G642A |
| Express | WPBF-D | Q215* | C643T |
| Express | WPBF-D | G218D | G653A |
| Express | WPBF-D | D219N | G655A |
| Express | WPBF-D | V221M | G661A |
| Express | WPBF-D | G223S | G667A |
| Express | WPBF-D | G223D | G668A |
| Express | WPBF-D | G228S | G682A |
| Express | WPBF-D | G228D | G683A |
| Express | WPBF-D | A232V | C695T |
| Express | WPBF-D | S233L | C698T |
| Express | WPBF-D | G237E | G710A |
| Express | WPBF-D | A238V | C713T |
| Express | WPBF-D | T239I | C716T |
| Express | WPBF-D | G243R | G727A |
| Express | WPBF-D | G243E | G728A |
| Express | WPBF-D | D244N | G730A |
| Express | WPBF-D | D245N | G733A |
| Express | WPBF-D | M247I | G741A |
| Express | WPBF-D | G248R | G742A |
| Express | WPBF-D | G248E | G743A |
| Express | WPBF-D | G249D | G746A |
| Express | WPBF-D | G264S | G790A |
| Express | WPBF-D | G264D | G791A |
| Express | WPBF-D | G265D | G794A |
| Express | WPBF-D | G266D | G797A |
| Express | WPBF-D | G267D | G800A |
| Express | WPBF-D | G270E | G809A |
| Express | WPBF-D | G276R | G826A |
| Express | WPBF-D | G278E | G833A |
| Express | WPBF-D | G304R | G910A |

In one embodiment, the disclosure relates to a polynucleotide of the WPBF gene in the D genome with one or more non-transgenic mutations listed in Table 3 and corresponding to SEQ ID NO: 8. In another embodiment, the polynucleotide with one or more non-transgenic mutations listed in Table 3 and has 85%, 86%, 87%, 88%, 89%, 90%, 91%, 92%, 93%, 94%, 95%, 96%, 97%, 98%, 99% or greater than 99% identity to SEQ ID NO: 8.

In still another embodiment, the polynucleotide with one or more non-transgenic mutation listed in Table 3 codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity to SEQ ID NO: 9.

SEQ ID NO. 7: WPBF-D genome:
CTGGCTTGCTCATTCTGCGGTAGTGTTTAAACATCAGCTAGCCTTACGGG

TATAAAAAGGTGGGCAACTTCACCCTATCCCATAGCACTAGACCAAACAA

CACCTATACTCCATACTACCCTTCATTCACCTGGTGAGATTCTTCTTCCT

```
TTGATCTCTATCACTTACTCTTTCTCCCTTCTTCTTCTTCTTCTTCT
TCTTCTTCTTCTTCTTCTTCTTCTTCTTCTTCTTCTTCCTCGTGCAT
GCTACTTTTGCTACATAATCTCCTGCAGTATCGCTCGCCGCAAGCTGTGC
TAGCTAGCTAGCGATCTTCACTTTAAGACCCGTTGTAGATCTAGCCACGG
GCTATTCCAAAAAATATTTCTCTTGTTTGCGTGTTCCTGTGTACATGCAT
GTATTTAGATCTTGATCTTGAAGAATTCATACTGAATTCATGACCTACCT
TGTTTGGTTTGTGTAATTTTGATGTTGTTGTATCAATTTTAGCAAACCGC
TCGTAGCTAGAACAATAGAGGGGGCGGCCGTATGTTTCCATTTCGAAAAG
GGGATATTTCCAGGCTCTGCATCGGTTCATGCACACAGCCGTTACCACAT
TCAATAGGCACTAATCCATGGATGCATGCCAGATTTACTAGTTTTGTTTA
CAAAGTTTTATTTTTTTTGCTTTGATTTACGAAAAATTGGATCGGATTT
TGCAGTTCTTTTTATCCATGTTGGATTCACTACTTTGAACCCAAGATTT
TATTTATTTTGTCTCGGTTTCTTACACGCCTGGTTAGGTAACTAGGAGAT
CCTGGGATTAGGCTTTCAAGGAATCCTAATACTAGAGAGTATGGGGAGAG
GCACCTTATTTTTTAAGTTGCCCAAAAGAATGGGCGCTTAGAGTTGTAGC
TAATTAATTGAATCTGTTGTATGGATCTGAGAATTTGAGACCTGATTATG
CACTTATCATGACATTTTGAGTCAACCAATGATTCTACATGTCTCACTCC
TTAGGATTAACAATTTAACTTAATTTAATTCGATATGTGTGTACACATGT
GTTGTAGATGGAGGAAGTGTTTCCGTCAAACTCCAAGAGCAAGGCAGGTC
AGATGGCGGGGAGGCGATAGCGGGGGCGGAGAAGAAGCCTCGGCCAAAG
CCAGAGCAGAAGGTGGAATGCCCTCGGTGCAAGTCTGGCAACACCAAGTT
CTGCTACTACAACAACTATAGTATGTCTCAGCCCCGCTACTTCTGCAAGG
CCTGCCGCCGCTACTGGACCCATGGTGGCTCCCTCCGCAACGTCCCCATC
GGTGGTGGCTGCCGCAAGCCCAAGCGCTCGGGGACCTCCGACGCCCACAA
GCTCGGCGTGGCCTCCTCACCGGAACCCACGACTGTCGTGCCCCCCTCGA
CCTGCACAGGGATGAACTTTGCGAACGTCCTCCCGACGTTTATGTCTGTT
GGTTTTGAGATTCCAAGCAGCCTTTCCCTAACCGCCTTTGGGTCATCAtc
GTCGTCCAACACGGCGGCGATGATGTCCCCTGGTGGGACGACGTCATTTC
TAGACGTGCTAAGAGGGGTGCAGGAGGGCTTCTTGATGGCAGCCTCAGT
CAGAACAATGGCTACTACTATGGTGGGCCAGCCATTGGATCAGGCAATGG
GATGCTGATGACGCCGCCAGCGGTGTCATTTGGCATTCCAGTTCCGATGC
AGCAGCATGGTGATCTCGTGGTTGGTGGAAATGGAATAGGTGCCGCAACT
GCTTCAATATTTCAAGGGGCCACTAGCGAGGAAGGAGATGACGGCATGGG
GGGCGTGATGGGCTCCAATGGCAACCACAGGTTGGCAATGGTGGAGGTG
GTGGTGGTGTATCAGGAGGCGTGCATCACCTTGGGACTGGGAACAATGTG
ACGATGGGCAACAGCAACATACACAACAACAACAATAACGACAGCGGCGG
TGATGACAACAATGGTGGGTCATCGAGGGATTGCTACTGGATCAACAATG
GAGGATCAAACCCATGGCAGAGCCTCCTCAACAGCAGCTCCCTGATGTAA
GTGCAAGAAGAAAATGGGAAATGGAGGTCAT
SEQ ID NO. 8: WPBF-D coding sequence:
ATGGAGGAAGTGTTTCCGTCAAACTCCAAGAGCAAGGCAGGTCAGATGGC
GGGGGAGGCGATAGCGGGGGCGGAGAAGAAGCCTCGGCCAAAGCCAGAGC
AGAAGGTGGAATGCCCTCGGTGCAAGTCTGGCAACACCAAGTTCTGCTAC
TACAACAACTATAGTATGTCTCAGCCCCGCTACTTCTGCAAGGCCTGCCG
CCGCTACTGGACCCATGGTGGCTCCCTCCGCAACGTCCCCATCGGTGGTG
GCTGCCGCAAGCCCAAGCGCTCGGGGACCTCCGACGCCCACAAGCTCGGC
GTGGCCTCCTCACCGGAACCCACGACTGTCGTGCCCCCCTCGACCTGCAC
AGGGATGAACTTTGCGAACGTCCTCCCGACGTTTATGTCTGTTGGTTTTG
AGATTCCAAGCAGCCTTTCCCTAACCGCCTTTGGGTCATCAtcGTCGTCC
AACACGGCGGCGATGATGTCCCCTGGTGGGACGACGTCATTTCTAGACGT
GCTAAGAGGGGTGCAGGAGGGCTTCTTGATGGCAGCCTCAGTCAGAACA
ATGGCTACTACTATGGTGGGCCAGCCATTGGATCAGGCAATGGGATGCTG
ATGACGCCGCCAGCGGTGTCATTTGGCATTCCAGTTCCGATGCAGCAGCA
TGGTGATCTCGTGGTTGGTGGAAATGGAATAGGTGCCGCAACTGCTTCAA
TATTTCAAGGGGCCACTAGCGAGGAAGGAGATGACGGCATGGGGGCGTG
ATGGGGCTCCAATGGCAACCACAGGTTGGCAATGGTGGAGGTGGTGGTGG
TGTATCAGGAGGCGTGCATCACCTTGGGACTGGGAACAATGTGACGATGG
GCAACAGCAACATACACAACAACAACAATAACGACAGCGGCGGTGATGAC
AACAATGGTGGGTCATCGAGGGATTGCTACTGGATCAACAATGGAGGATC
AAACCCATGGCAGAGCCTCCTCAACAGCAGCTCCCTGATG
SEQ ID NO. 9: WPBF-D amino acid sequence
MEEVFPSNSKSKAGQMAGEAIAGAEKKPRPKPEQKVECPRCKSGNTKFCY
YNNYSMSQPRYFCKACRRYWTHGGSLRNVPIGGGCRKPKRSGTSDAHKLG
VASSPEPTTVVPPSTCTGMNFANVLPTFMSVGFEIPSSLSLTAFGSSSSS
NTAAMMSPGGTTSFLDVLRGGAGGLLDGSLSQNNGYYYGGPAIGSGNGML
MTPPAVSFGIPVPMQQHGDLVVGGNGIGAATASIFQGATSEEGDDGMGGV
MGLQWQPQVGNGGGGGVSGGVHHLGTGNNVTMGNSNIHNNNNNDSGGDD
NNGGSSRDCYWINNGGSNPWQSLLNSSSLM
```

4. Dof Region

In one embodiment, the disclosure relates to multiple non-transgenic mutations in the Dof region of WPBF gene of the A, B, or D genome. In one embodiment, the disclosure relates to multiple non-transgenic mutations in the Dof region of WPBF gene of the A and B genome. In one embodiment, the disclosure relates to multiple non-transgenic mutations in the Dof region of WPBF gene of the A and D genome. In one embodiment, the disclosure relates to multiple non-transgenic mutations in the Dof region of WPBF gene of the B and D genome.

In yet another embodiment, the disclosure relates to one or more non-transgenic mutations in the Dof region as shown in SEQ ID NO. 10 of the WPBF gene.

In yet another embodiment, the disclosure relates to one or more non-transgenic mutations in the Dof region as shown in SEQ ID NO. 11 of the WPBF protein. One or more of the 63 amino acids shown in SEQ ID NO. 11 can be mutated. The mutations can be severe or conservative.

In one embodiment, the Q at position 28 of SEQ ID NO. 11 is mutated. In one embodiment, the glutamine (Q) at position 28 of SEQ ID NO. 11 can be mutated to a leucine (L).

SEQ ID NO. 10: Dof Region of WPBF Gene
AAGCCAGAGCAGAAGGTGGAATGCCCTCGGTGCAAGTCTGGCAACACCAA

GTTCTGCTACTACAACAACTATAGTATGTCTCAGCCCCGCTACTTCTGCA

AGGCCTGCCGCCGCTACTGGACCCATGGTGGCTCCCTCCGCAACGTCCCC

ATCGGTGGTGGCTGCCGCAAGCCCAAGCGCTCGGGGACC

SEQ ID NO. 11: Dof region of WPBF Protein
KPEQKVECPRCKSGNTKFCYYNNYSMSQPRYFCKACRRYWTHGGSLRNVP

IGGGCRKPKRSGT

B. WPBF Proteins

In yet another embodiment, the disclosure relates to one or more non-transgenic mutations in the WPBF gene (as discussed above in the section entitled WPBF Mutations) that result in a WPBF protein with one or more mutations as compared to wild type WPBF protein. In one embodiment, the non-transgenic mutations include but are not limited to the mutations recited in Tables 1-3, corresponding mutations in homoeologues, and combinations thereof.

In another embodiment, the disclosure relates to one or more non-transgenic mutations in the WPBF gene that inhibits production of the WPBF protein. In some embodiments, a mutation in the WPBF gene reduces expression of the WPBF protein. In other embodiments, a mutation in the WPBF gene creates an unstable or a WPBF protein with reduced function.

1. Expression Level of WPBF protein

In another embodiment, the expression level of WPBF protein with one or more mutations disclosed herein is reduced by 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, and 95-99% of the expression level of the wild type WPBF protein.

In still another embodiment, the expression level of WPBF protein with one or more mutations disclosed herein is reduced from 10-20%, or from 20-30%, or from 30-40%, or from 40-50%, or from 50-60%, or from 60-70%, or from 70-80%, or from 80-90%, or from 90-99% as compared to the expression level of the wild type WPBF protein.

2. Activity of WPBF Protein

In yet another embodiment, the activity of the WPBF protein with one or more mutations disclosed herein is reduced to 0-1, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99% and by more than 99% of the activity level of the wild type WPBF protein. In another embodiment, the WPBF protein with one or more mutations disclosed herein has no activity or zero activity as compared to wild type WPBF protein.

In yet another embodiment, the activity of the WPBF protein with one or more mutations disclosed herein is from 1-10% or from 10-30% or from 30-50% or from 50-70% or from 70-80% or from 80-90% or from 90-95% of the activity level of the wild type WPBF protein.

III. Transgenes

In one embodiment, the disclosure relates to a transgenic plant that comprises a transgene that encodes a polynucleotide, which down-regulates the expression of the WPBF gene and/or the activity of the WPBF protein. Examples of such polynucleotides include, but are not limited to, antisense polynucleotide, a sense polynucleotide, a catalytic polynucleotide, an artificial microRNA or a duplex RNA molecule.

In one embodiment, the disclosure relates to a wheat plant comprising a transgene that reduces the expression of the WPBF gene and/or activity of the WPBF protein, wherein the wheat plant has reduced gluten grains as compared to grains from a wild type plant.

A. Antisense Polynucleotides

The term "antisense polynucletoide" shall be taken to refer to a DNA or RNA, or combination thereof, molecule that is complementary to at least a portion of a specific mRNA molecule encoding WPBF and capable of interfering with a post-transcriptional event such as mRNA translation.

An antisense polynucleotide in a plant will hybridize to a target polynucleotide under physiological conditions. As used herein, the term "an antisense polynucleotide which hybridizes under physiological conditions" means that the polynucleotide (which is fully or partially single stranded) is at least capable of forming a double stranded polynucleotide with mRNA encoding a protein.

Antisense molecules may include sequences that correspond to the structural gene or for sequences that effect control over the gene expression or splicing event. For example, the antisense sequence may correspond to the targeted coding region of WPBF or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition.

The length of the antisense sequence should be at least 19 contiguous nucleotides, preferably at least 50 nucleotides, and more preferably at least 100, 200, 500 or 1000 nucleotides. The full-length sequence complementary to the entire gene transcript may be used. The length is most preferably 100-2000 nucleotides. The degree of identity of the antisense sequence to the targeted transcript should be at least 90% and more preferably 95-100%. The antisense RNA molecule may of course comprise unrelated sequences, which may function to stabilize the molecule.

B. Catalytic Polynucleotides The term catalytic polynucleotide/nucleic acid refers to a DNA molecule or DNA-containing molecule (also known in the art as a "deoxyribozyme") or an RNA or RNA-containing molecule (also known as a "ribozyme") which specifically recognizes a distinct substrate and catalyzes the chemical modification of this substrate. The nucleic acid bases in the catalytic nucleic acid can be bases A, C, G, T (and U for RNA).

Typically, the catalytic nucleic acid contains an antisense sequence for specific recognition of a target nucleic acid, and a nucleic acid cleaving enzymatic activity (also referred to herein as the "catalytic domain").

The ribozymes in plants disclosed herein and DNA encoding the ribozymes can be chemically synthesized using methods well known in the art. The ribozymes can also be prepared from a DNA molecule (that upon transcription, yields an RNA molecule) operably linked to an RNA polymerase promoter, e.g., the promoter for T7 RNA polymerase or SP6 RNA polymerase. When the vector also contains an RNA polymerase promoter operably linked to the DNA molecule, the ribozyme can be produced in vitro upon incubation with RNA polymerase and nucleotides. In a separate embodiment, the DNA can be inserted into an expression cassette or transcription cassette. After synthesis, the RNA molecule can be modified by ligation to a DNA molecule having the ability to stabilize the ribozyme and make it resistant to RNase.

As with antisense polynucleotides described herein, the catalytic polynucleotides should also be capable of hybridizing a target nucleic acid molecule (for example mRNA encoding WPBF) under "physiological conditions," namely those conditions within a plant cell.

C. RNA Interference

RNA interference (RNAi) is particularly useful for specifically inhibiting the production of a particular protein. This technology relies on the presence of dsRNA molecules that contain a sequence that is essentially identical to the mRNA of the gene of interest or part thereof. Conveniently, the dsRNA can be produced from a single promoter in a recombinant vector or host cell, where the sense and anti-sense sequences are flanked by an unrelated sequence which enables the sense and anti-sense sequences to hybridize to form the dsRNA molecule with the unrelated sequence forming a loop structure. The design and production of suitable dsRNA molecules for the present invention is well within the capacity of a person skilled in the art, particularly considering, WO 99/32619, WO 99/53050, WO 99/49029, and WO 01/34815.

In one example, a DNA is introduced that directs the synthesis of an at least partly double stranded (duplex) RNA product(s) with homology to the target gene to be inactivated. The DNA therefore comprises both sense and anti-sense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule is thought to trigger a response from an endogenous plant system that destroys both the double stranded RNA and also the homologous RNA transcript from the target plant gene, efficiently reducing or eliminating the activity of the target gene.

The length of the sense and antisense sequences that hybridize should each be at least 19 contiguous nucleotides, preferably at least 30 or 50 nucleotides, and more preferably at least 100, 200, 500 or 1000 nucleotides. The full-length sequence corresponding to the entire gene transcript may be used. The lengths are most preferably 100-2000 nucleotides. The degree of identity of the sense and antisense sequences to the targeted transcript should be at least 85%, preferably at least 90% and more preferably 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters.

In one embodiment, small interfering RNA ("siRNA") molecules comprise a nucleotide sequence that is identical to about 19-21 contiguous nucleotides of the target mRNA. Preferably, the target mRNA sequence commences with the dinucleotide AA, comprises a GC-content of about 30-70% (preferably, 30-60%, more preferably 40-60% and more preferably about 45%-55%), and does not have a high percentage identity to any nucleotide sequence other than the target in the genome of the barley plant in which it is to be introduced, e.g., as determined by standard BLAST search.

D. microRNA

MicroRNA regulation is a clearly specialized branch of the RNA silencing pathway that evolved towards gene regulation, diverging from conventional RNAi/Post transcriptional Gene Silencing (PTGS). MicroRNAs are a specific class of small RNAs that are encoded in gene-like elements organized in a characteristic inverted repeat. When transcribed, microRNA genes give rise to stem-looped precursor RNAs from which the microRNAs are subsequently processed. MicroRNAs are typically about 21 nucleotides in length. The released miRNAs are incorporated into RISC-like complexes containing a particular subset of Argonaute proteins that exert sequence-specific gene repression.

E. Co-Suppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to WO 97/20936 and EP 0465572 for methods of implementing co-suppression approaches.

IV. Genomic Editing

In one embodiment, the disclosure relates to a plant with reduced expression of the WPBF gene and/or reduced activity of the WPBF protein, wherein reduced expression of the WPBF gene and/or reduced activity of the WPBF protein is achieved by genomic editing.

In one embodiment, the disclosure relates to a wheat plant with a genomically edited WPBF gene, wherein the wheat plant has reduced gluten grains as compared to a wild type plant.

Genome editing, or genome editing with engineered nucleases (GEEN), is a type of genetic engineering in which DNA is inserted, replaced, or removed from a genome using artificially engineered nucleases, or "molecular scissors." The nucleases create specific double-stranded breaks (DSBs) at desired locations in the genome, and harness the cell's endogenous mechanisms to repair the induced break by natural processes of homologous recombination (HR) and nonhomologous end-joining (NHEJ). There are currently four main families of engineered nucleases being used: Zinc finger nucleases (ZFNs), Transcription Activator-Like Effector Nucleases (TALENs), the CRISPR/Cas system, and engineered meganuclease with a re-engineered homing endonucleases.

A. Zinc Finger Nucleases (ZFNs)

Zinc-finger nucleases (ZFNs) are artificial restriction enzymes generated by fusing a zinc finger DNA-binding domain to a DNA-cleavage domain. Zinc finger domains can be engineered to target specific desired DNA sequences and this enables zinc-finger nucleases to target unique sequences within complex genomes. By taking advantage of endogenous DNA repair machinery, these reagents can be used to precisely alter the genomes of higher organisms.

ZFNs consist of an engineered zinc finger DNA-binding domain fused to the cleavage domain of the FokI restriction endonuclease. ZFNs can be used to induce double-stranded breaks (DSBs) in specific DNA sequences and thereby promote site-specific homologous recombination with an exogenous template. The exogenous template contains the sequence that is to be introduced into the genome.

Publicly available methods for engineering zinc finger domains include: (1) Context-dependent Assembly (CoDA), (2) Oligomerized Pool Engineering (OPEN), and (3) Modular Assembly.

In one embodiment, the disclosure relates to reducing expression of the WPBF gene and/or reducing activity of the WPBF protein using ZFNs.

B. Transcription Activator-Like Effector Nucleases (TALENs)

TALEN is a sequence-specific endonuclease that consists of a transcription activator-like effector (TALE) and a FokI endonuclease. TALE is a DNA-binding protein that has a highly conserved central region with tandem repeat units of 34 amino acids. The base preference for each repeat unit is determined by two amino acid residues called the repeat-variable di-residue (RVD), which recognizes one specific nucleotide in the target DNA. Arrays of DNA-binding repeat units can be customized for targeting specific. DNA sequences. As with ZFNs, dimerization of two TALENs on targeted specific sequences in a genome results in FokI-dependent introduction of DSBs, stimulating homology directed repair (HDR) and Non-homologous end joining (NHEJ) repair mechanisms.

In one embodiment, the disclosure relates to reducing expression of the WPBF gene and/or reducing activity of the WPBF protein using TALENs.

C. CRISPR/Cas System

The Clustered Regularly Interspaced Short Palindromic Repeats (CRISPR) Type II system is an RNA-Guided Endonuclease technology for genome engineering. There are two distinct components to this system: (1) a guide RNA and (2) an endonuclease, in this case the CRISPR associated (Cas) nuclease, Cas9.

The guide RNA is a combination of the endogenous bacterial crRNA and tracrRNA into a single chimeric guide. RNA (gRNA) transcript. The gRNA combines the targeting specificity of the crRNA with the scaffolding properties of the tracrRNA into a single transcript. When the gRNA and the Cas9 are expressed in the cell, the genomic target sequence can be modified or permanently disrupted.

The gRNA/Cas9 complex is recruited to the target sequence by the base-pairing between the gRNA sequence and the complementarity to the target sequence in the genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the wild-type Cas9 can cut both strands of DNA causing a Double Strand Break (DSB). Cas9 will cut 3-4 nucleotides upstream of the PAM sequence. A DSB can be repaired through one of two general repair pathways: (1) NHEJ DNA repair pathway or (2) the HDR pathway. The NHEJ repair pathway often results in insertions/deletions (InDels) at the DSB site that can lead to frameshifts and/or premature stop codons, effectively disrupting the open reading frame (ORF) of the targeted gene.

The HDR pathway requires the presence of a repair template, which is used to fix the DSB, HDR faithfully copies the sequence of the repair template to the cut target sequence. Specific nucleotide changes can be introduced into a targeted gene by the use of HDR with a repair template.

In one embodiment, the disclosure relates to reducing expression of the WPBF gene and/or reducing activity of the WPBF protein using the CRISPR/cas9 system.

D. Meganuclease with Re-Engineered Homing Nuclease

Meganucleases are endodeoxyribonucleases characterized by a large recognition site (double-stranded DNA sequences of 12 to 40 base pairs); as a result this site generally occurs only once in any given genome. For example, the 18-base pair sequence recognized by the I-SeeI meganuclease would on average require a genome twenty times the size of the human genome to be found once by chance (although sequences with a single mismatch occur about three times per human-sized genome). Meganucleases are therefore considered to be the most specific naturally occurring restriction enzymes.

Among meganucleases, the LAGLIDADG family of homing endonucleases has become a valuable tool for the study of genomes and genome engineering over the past fifteen years. By modifying their recognition sequence through protein engineering, the targeted sequence can be changed.

In one embodiment, the disclosure relates to reducing expression of the WPBF gene and/or reducing activity of the WPBF protein using a meganuclease with a re-engineered homing nuclease.

V. Wheat Cultivars

In one embodiment, a wheat cultivar having at least one WPBF gene that is diploid, polyploid, tetraploid, and hexaploid may be used.

In another embodiment, the wheat is *Triticum aestivum*.

In one embodiment, any cultivar of wheat can be used to create mutations in an WPBF gene. In one embodiment, any cultivar of wheat can be used to create mutations in the WPBF gene of the A genome. In another embodiment, any cultivar of wheat can be used to create mutations in the WPBF gene of the B genome. In another embodiment, any cultivar of wheat can be used to create mutations in the WPBF gene of the D genome.

In one embodiment, any cultivar of wheat can be used as lines to cross WPBF mutations into different cultivars. In another embodiment, any cultivar of wheat having at least one WPBF gene may be used including but not limited to hard red spring wheat, hard white wheat, *durum* wheat, soft white spring wheat, soft white winter wheat, hard red winter wheat, common wheat, club wheat, spelt wheat, emmer wheat, pasta wheat and turgidum wheat.

In one embodiment, hard red spring wheat includes but is not limited to Bullseye, Cabernet, Cal Rojo, Hank, Joaquin, Kelse, Lariat, Lassik, Malbec, Mika, PR 1404, Redwing, Summit 515, SY 314, Triple IV, Ultra, WB-Patron, WB-Rockland, Yecora Rojo, Accord, Aim, Anza, Baker, Beth Hashita, Bonus, Borah, Brim, Brooks, Buck Pronto, Butte 86, Cavalier, Challenger, Chief, Ciano T79, Colusa, Companion, Copper, Cuyama, Dash 12, Eldon, Enano, Express, Expresso, Jefferson, Genero F81, Grandin, Helena 554, Hollis, Imuris T79, Inia 66R, Jerome, Kern, Len, Marshall, McKay, Nomad, Northwest 10, Oslo, Pavon F76, Pegasus, Pitic 62, Poco Red, Powell, Probrand 711, Probrand 751, Probrand 771, Probrand 775, Probred, Prointa Queguay, Prointa Quintal, Rich, RSI 5, Sagittario, Scarlet, Serra, Shasta, Solano, Spillman, Sprite, Stander, Stellar, Stoa, Success, Summit, Sunstar 2, Sunstar King, Tadinia, Tammy, Tanori 71, Tara 2000, Tempo, Tesia T79, Topic, UI Winchester, Vance, Vandal, W444, Wampum, Wared, WB-Fuzion, Westbred 906R, Westbred 911, Westbred 926, Westbred 936, Westbred Discovery, Westbred Rambo, Yolo, and Zeke.

In another embodiment, hard white wheat includes but is not limited to Blanca Fuerte, Blanca Grande 515, Blanca Royale, Clear White, Patwin, Patwin 515, WB-Cristallo, WB-Paloma, WB-Perla, Alta Blanca, Blanca Grande, Delano, Golden Spike, ID377S, Klasic, Lochsa, Lolo, Macon, Otis, Phoenix, Pima 77, Plata, Pristine, Ramona 50, Siete Cerros 66, Vaiolet, and Winsome.

In yet another embodiment, *durum* wheat includes but is not limited to Crown, Desert King, Desert King HP, Duraking, Fortissimo, Havasu, Kronos, Maestrale, Normanno, Orita, Platinum, Q-Max, RSI 59, Saragolla, Tango, Tipai, Topper, Utopia, Volante, WB-Mead, Westmore, Aldente, Aldura, Altar 84, Aruba, Bittern, Bravadur, Candura, Cortez, Deluxe, Desert Titan, Durex, Durfort, Eddie, Germains 5003D, Imperial, Kofa, Levante, Matt, Mead, Mexicali 75, Minos, Modoc, Mohawk, Nudura, Ocotillo, Produra, Reva, Ria, Septre, Sky, Tacna, Titan, Trump, Ward, Westbred 803, Westbred 881, Westbred 883, Westbred 1000D, Westbred Laker, Westbred Turbo, and Yavaros 79.

In another embodiment, soft white spring wheat includes but is not limited to Alpowa, Alturas, Babe, Diva, JD, New Dirkwin, Nick, Twin, Whit, Blanca, Bliss, Calorwa, Centennial, Challis, Dirkwin, Eden, Edwall, Fielder, Fieldwin, Jubilee, Louise, Owens, Penawawa, Pomerelle, Sterling, Sunstar Promise, Super Dirkwin, Treasure, UI Cataldo, UI Pettit, Urquie, Vanna, Waduel, Waduel 94, Wakanz, Walladay, Wawawai, Whitebird, and Zak.

In still another embodiment, soft white winter wheat includes but is not limited to AP Badger, AP Legacy, Brundage 96, Bruneau, Cara, Goetze, Legion, Mary, Skiles, Stephens, SY Ovation, Tubbs, WB-Junction, WB-528, Xerpha, Yamhill, Barbee, Basin, Bitterroot, Bruehl, Castan, Chukar, Coda, Daws, Edwin, Eltan, Faro, Finch, Foote, Gene, Hill 81, Hiller, Hubbard, Hyak, Hyslop, Idaho 587, Kmor, Lambert, Lewjain, MacVicar, Madsen, Malcolm, Masami, McDermid, Moro, Nugaines, ORCF-101, ORCF-102, ORCF-103, Rod, Rohde, Rulo, Simon, Salute, Temple, Tres, Tubbs 06, UICF-Brundage, WB-523, and Weatherford.

In another embodiment, hard red winter wheat includes but is not limited to Andrews, Archer, Batum, Blizzard, Bonneville, Boundary, Declo, Deloris, Finley, Garland, Hatton, Hoff, Longhorn, Manning, Meridian, Promontory, Vona, Wanser, Winridge.

In another embodiment, common wheat (hexaploid, free threshing), *Triticum aestivum* ssp *aestivum* includes but is not limited to Sonora, Wit Wolkoring, Chiddam Blanc De Mars, India-Jammu, Foisy.

In still another embodiment, spelt wheat (hexaploid, not free threshing), *Triticum aestivum* ssp *spelta* includes but is not limited to Spanish Spelt, Swiss Spelt.

In yet another embodiment, Emmer Wheat (tetraploid), *Triticum turgidum* ssp. *dicoccum* includes but is not limited to Ethiopian Blue Tinge.

In another embodiment, pasta wheat (tetraploid, free threshing), *Triticum turgidum* ssp *durum* includes but is not limited to Blue Beard, Durum-Iraq.

In yet another embodiment, *Turgidum* Wheat (tetraploid, free threshing), *Triticum turgidum* ssp *turgidum* includes but is not limited to Akmolinka, Maparcha.

In one embodiment, a cultivar of wheat having at least one WPBF gene with substantial percent identity to SEQ ID NO: 1, SEQ ID NO: 2, SEQ ID NO: 4, SEQ ID NO: 5, SEQ ID NO. 7, or SEQ ID NO. 8 may be used with the methods and compositions disclosed herein.

As used herein with regard to the wheat cultivars, "substantial percent identity" means that the DNA sequence of the gene is sufficiently similar to SEQ ID NO: 1, 2, 4, 5, 7 and 8 at the nucleotide level to code for a substantially similar protein, allowing for allelic differences (or alternate mRNA splicing) between cultivars. In accordance with one embodiment of the invention, "substantial percent identity" may be present when the percent identity in the coding region between the WPBF gene and SEQ ID NO: 1, 2, 4, 5, 7, and 8 is as low as about 85%, provided that the percent identity in the conserved regions of the gene is higher (e.g., at least about 90%). Preferably the percent identity in the coding region is 85-90%, more preferably 90-95%, and optimally, it is above 95%. Thus, one of skill in the art may prefer to utilize a wheat cultivar having commercial popularity or one having specific desired characteristics in which to create the WPBF-mutated wheat plants, without deviating from the scope and intent of the present invention. Alternatively, one of skill in the art may prefer to utilize a wheat cultivar having few polymorphisms, such as an in-bred cultivar, in order to facilitate screening for mutations within one or more WPBF genes in accordance with the present invention.

VI. Representative Methodology for Identification of WPBF Mutations

One of ordinary skill in the art will appreciate that numerous techniques and methods are available for generating mutations and/or non-transgenic mutations. One representative methodology is described below.

In order to create and identify the WPBF mutations and wheat plants disclosed herein, a method known as TILLING was utilized. See McCallum et al., *Nature Biotechnology* 18:455-457, 2000; McCallum et al., *Plant Physiology*, 123: 439-442, 2000; U.S. Publication No. 20040053236; and U.S. Pat. No. 5,994,075, all of which are incorporated herein by reference. In the basic TILLING methodology, plant materials, such as seeds, are subjected to chemical mutagenesis, which creates a series of mutations within the genomes of the seeds' cells. The mutagenized seeds are grown into adult M1 plants and self-pollinated. DNA samples from the resulting M2 plants are pooled and are then screened for mutations in a gene of interest. Once a mutation is identified in a gene of interest, the seeds of the M2 plant carrying that mutation are grown into adult M3 plants and screened for the phenotypic characteristics associated with that mutation in the gene of interest.

In one embodiment, the tetraploid cultivar Kronos was used. In other embodiments, the hexaploid cultivar Express was used.

In one embodiment, seeds from wheat are mutagenized and then grown into M1 plants. The M1 plants are then allowed to self-pollinate and seeds from the M1 plant are grown into M2 plants, which are then screened for mutations in their WPBF loci. While M1 plants can be screened for mutations in accordance with alternative embodiments of the invention, one advantage of screening the M2 plants is that all somatic mutations correspond to germline mutations.

One of skill in the art will understand that a variety of wheat plant materials, including, but not limited to, seeds, pollen, plant tissue or plant cells, may be mutagenized in order to create the WPBF-mutated wheat plants disclosed herein. However, the type of plant material mutagenized may affect when the plant DNA is screened for mutations. For example, when pollen is subjected to mutagenesis prior to pollination of a non-mutagenized plant, the seeds resulting from that pollination are grown into M1 plants. Every cell of the M1 plants will contain mutations created in the pollen, thus these M1 plants may then be screened for WPBF mutations instead of waiting until the M2 generation.

Mutagens that create primarily point mutations and short deletions (about 1 to about 30 nucleotides), insertions, transversions, and or transitions, such as chemical mutagens or radiation, such as x-rays and fast neutrons, may be used to create the mutations. Mutagens conforming with the method of the invention include, but are not limited to, ethyl methanesulfonate (EMS), methylmethane sulfonate (MMS), N-ethyl-N-nitrosourea (ENU), triethylmelamine (TEM), N-methyl-N-nitrosourea (MNU), procarbazine, chlorambucil, cyclophosphamide, diethyl sulfate, acrylamide monomer, melphalan, nitrogen mustard, vincristine, dimethylnitrosamine, N-methyl-N'-nitro-Nitrosoguanidine (MNNG), nitrosoguanidine, 2-aminopurine, 7, 12 dimethyl-benz(a) anthracene (DMBA), ethylene oxide, hexamethylphosphoramide, bisulfan, diepoxyalkanes (diepoxyoctane (DEO), diepoxybutane (DEB), and the like), 2-methoxy-6-chloro-9 [3-(ethyl-2-chloro-ethyl)aminopropylamino] acridine dihydrochloride (ICR-170), sodium azide, and formaldehyde. Spontaneous mutations in a WPBF gene that may not have been directly caused by the mutagen can also be identified.

Any suitable method of plant DNA preparation now known or hereafter devised may be used to prepare the wheat plant DNA for WPBF mutation screening. For example, see Chen & Ronald, *Plant Molecular Biology Reporter* 17:53-57, 1999; Stewart and Via, *Bio Techniques* 14:748-749, 1993. Additionally, several commercial kits designed for this purpose are available, including kits from Qiagen (Valencia, Calif.) and Qbiogene (Carlsbad, Calif.).

In one embodiment, prepared DNA from individual wheat plants are pooled in order to expedite screening for mutations in one or more WPBF genes of the entire population of plants originating from the mutagenized plant tissue. The size of the pooled group may be dependent upon the sensitivity of the screening method used. Preferably, groups of two or more individual wheat plants are pooled.

In another embodiment, after the DNA samples are pooled, the pools are subjected to WPBF sequence-specific amplification techniques, such as Polymerase Chain Reaction (PCR). For a general overview of PCR, see *PCR Protocols: A Guide to Methods and Applications* (Innis, Gelfand, Sninsky, and White, eds.), Academic Press, San Diego, 1990.

Any primer specific to a WPBF locus or the sequences immediately adjacent to one of these loci may be utilized to amplify the WPBF sequences within the pooled DNA sample. Preferably, the primer is designed to amplify the regions of the WPBF locus where useful mutations are most likely to arise. Most preferably, the primer is designed to detect exonic regions of one or more WPBF genes. Additionally, it is preferable for the primer to target known polymorphic sites to design genome specific primers in order to ease screening for point mutations in a particular genome. To facilitate detection of PCR products on a gel, the PCR primer may be labeled using any conventional or hereafter devised labeling method.

In one embodiment, primers are designed based upon the WPBF genes (SEQ ID NOs: 1, 2, 4, 5, 7, and 8). In another embodiment, primers can be designed that are 5' or 3' to the WPBF genes.

In another embodiment, the PCR amplification products may be screened for WPBF mutations using any method that identifies nucleotide differences between wild type and mutant sequences. These may include, for example, without limitation, sequencing, denaturing high pressure liquid chromatography (dHPLC), constant denaturant capillary electrophoresis (CDCE), temperature gradient capillary electrophoresis (TGCE) (see Li et al., *Electrophoresis* 23(10):1499-1511, 2002), or by fragmentation using enzymatic cleavage, such as used in the high throughput method described by Colbert et al., *Plant Physiology* 126:480-484, 2001. Preferably, the PCR amplification products are incubated with an endonuclease that preferentially cleaves mismatches in heteroduplexes between wild type and mutant sequences.

In another embodiment, cleavage products are electrophoresed using an automated sequencing gel apparatus, and gel images are analyzed with the aid of a standard commercial image-processing program.

In yet another embodiment, once an M2 plant having a mutated WPBF gene sequence is identified, the mutations are analyzed to determine their effect on the expression, translation, and/or activity of a WPBF enzyme. In one embodiment, the PCR fragment containing the mutation is sequenced, using standard sequencing techniques, in order to determine the exact location of the mutation in relation to the overall WPBF sequence. Each mutation is evaluated in order to predict its impact on protein function (i.e., from completely tolerated to causing loss-of-function) using bioinformatics tools such as SIFT (Sorting Intolerant from Tolerant; Ng and Henikoff, *Nucleic Acids Research* 31:3812-3814, 2003), PSSM (Position-Specific Scoring Matrix; Henikoff and Henikoff, *Computer Applications in the Biosciences* 12:135-143, 1996) and PARSESNP (Taylor and Greene, *Nucleic Acids Research* 31:3808-3811, 2003). For example, a SIFT score that is less than 0.05 and a large change in PSSM score (e.g., roughly 10 or above) indicate a mutation that is likely to have a deleterious effect on protein function. These programs are known to be predictive, and it is understood by those skilled in the art that the predicted outcomes are not always accurate.

In another embodiment, if the initial assessment of a mutation in the M2 plant indicates it to be of a useful nature and in a useful position within a WPBF gene, then further phenotypic analysis of the wheat plant containing that mutation may be pursued. In hexaploid wheat, mutations in each of the A, B and D genomes usually must be combined before a phenotype can be detected. In tetraploid wheat, A and B genome mutations are combined. In addition, the mutation containing plant can be backcrossed or outcrossed two times or more in order to eliminate background mutations at any generation. Then, the backcrossed or outcrossed plant can be self-pollinated or crossed in order to create plants that are homozygous for the WPBF mutations.

Several physical characteristics of these homozygous WPBF mutant plants are assessed to determine if the mutation results in a useful phenotypic change in the wheat plant without resulting in undesirable negative effects, such as significantly reduced seed yields.

VII. Methods of Producing a Wheat Plant

In another embodiment, the disclosure relates to a method for producing a wheat plant with reduced gluten grains. In another embodiment, the disclosure relates to a method for producing a wheat plant with increased high molecular weight glutenins. In another embodiment, the disclosure relates to a method for producing plants with reduced low molecular weight glutenins. In another embodiment, the disclosure relates to a method for producing plants with reduced gliadins. In still another embodiment, the disclosure relates to a method for producing plants with reduced low molecular weight glutenins in relation to wild type plants and a level of high molecular glutenins that is comparable to wild type plants.

In another embodiment, the disclosure relates to a method of out-crossing WPBF gene mutations to wild type plants.

In still another embodiment, the disclosure relates to a method for producing a plant having reduced activity of one or more WPBF proteins as compared to the wild type wheat plants.

In one embodiment, the method comprises inducing at least one non-transgenic mutation in at least one copy of a WPBF gene in plant material or plant parts from a parent plant; growing or using the mutagenized plant material to produce progeny plants; analyzing mutagenized plant material and/or progeny plants to detect at least one mutation in at least one copy of a WPBF gene; and selecting progeny plants that have at least one mutation in at least one copy of a WPBF gene.

In another embodiment, the method further comprises crossing progeny plants that have at least one mutation in at least one copy of a WPBF gene with other progeny plants that have at least one mutation in a different copy of a WPBF gene. The process of identifying progeny plants with mutations and crossing said progeny plants with other progeny plants, which have mutations, can be repeated to produce progeny wheat plants with reduced WPBF activity.

In another embodiment, the level of activity of the WPBF protein in the wheat plant is reduced to 0-2%, 2-5%, 5-7%, 7-10%, 10-15%, 15-20%, 20-25%, 25-30%, 30-35%, 35-40%, 40-45%, 45-50%, 50-60%, 60-70%, 70-80%, 80-90%, 90-95%, or 95-99% of the level of activity of the WPBF protein in the wild type plant.

A. Methods of Producing a Plant with One or More Mutations in the WPBF Gene in More than One Genome In still another embodiment, the disclosure relates to a method for producing a plant comprising the following: inducing at least one non-transgenic mutation in at least one copy of a WPBF gene in plant material from a parent plant that comprises a mutation in a WPBF gene; growing or using the mutagenized plant material to produce progeny plants; and selecting progeny wheat plants that have at least one mutation in at least two copies of a WPBF gene. For example, the parent plant may have a mutation in a WPBF gene of the D genome. The selected progeny plants may have a mutation in a WPBF gene of the D genome and one or more mutations in the WPBF gene of the B genome. This example is provided merely for clarification and should not limit the methods disclosed herein.

In yet another embodiment, the invention relates to a method for producing a plant comprising inducing at least one non-transgenic mutation in at least one copy of a WPBF gene in plant material from a parent plant that comprises at least one mutation in two WPBF genes; growing or using the mutagenized plant material to produce progeny plants; and selecting progeny plants that have at least one mutation in three copies of a WPBF gene. In this embodiment, there would be at least one mutation in the WPBF gene of the A, B and D genomes.

In another embodiment, the disclosure relates to a method for producing a wheat plant comprising crossing a first plant that has at least one non-transgenic mutation in a first WPBF gene with a second plant that has at least one non-transgenic mutation in a second WPBF gene; and selecting progeny plants that have at least one mutation in at least two copies of a WPBF gene.

In another embodiment, the disclosure relates to a method for producing a plant comprising crossing a first plant that has at least one non-transgenic mutation in a first and second WPBF gene with a second plant that has at least one non-transgenic mutation in a third WPBF gene; and selecting progeny plants that have at least one mutation in all three copies of a WPBF gene. In this embodiment, there would be at least one mutation in the WPBF gene of the A, B and D genomes.

VIII. Wheat Plant, Wheat Seed and Parts of Wheat Plant

In one embodiment, a wheat plant with reduced gluten grains is produced according to the methods disclosed herein. In one embodiment, a wheat plant with reduced low molecular weight glutenins is produced according to the methods disclosed herein. In one embodiment, a wheat plant with reduced gliadins is produced according to the methods disclosed herein. In yet another embodiment, a wheat plant with increased or unaltered high molecular weight glutenins is produced according to the methods disclosed herein.

In another embodiment, the wheat plant, wheat seed or parts of a wheat plant have one or more mutations in a WPBF gene or a modified WPBF gene. In another embodiment, the wheat plant, wheat seed or parts of a wheat plant have one or more mutations in WPBF genes.

In another embodiment, the disclosure relates to a wheat plant, wheat seed or parts of a wheat plant comprising one or more non-transgenic mutations in the WPBF gene. In another embodiment, the disclosure relates to a wheat plant, wheat seed or parts of a wheat plant comprising at least one non-transgenic mutation in the WPBF gene in each of two genomes. In still another embodiment, the disclosure relates to a wheat plant, wheat seed or parts of a wheat plant comprising at least one non-transgenic mutation in the WPBF gene in each of three genomes.

In one embodiment, the wheat plant, wheat seed or parts of a wheat plant comprises one or more non-transgenic mutations in both alleles of the WPBF gene in the A genome. In another embodiment, the non-transgenic mutations are identical in both alleles of the WPBF gene of the A genome.

In one embodiment, the wheat plant, wheat seed or parts of a wheat plant comprises one or more non-transgenic mutations in both alleles of the WPBF gene in the B genome. In another embodiment, the non-transgenic mutations are identical in both alleles of the WPBF gene of the B genome.

In one embodiment, the wheat plant, wheat seed or parts of a wheat plant comprises one or more non-transgenic mutations in both alleles of the WPBF gene in the D genome. In another embodiment, the non-transgenic mutations are identical in both alleles of the WPBF gene of the D genome.

In another embodiment, the wheat plant, wheat seed or parts of the wheat plant comprise a polynucleotide with one or more non-transgenic mutations listed in Table 1 and has 85%, 86%, 87%, 88%, 89%, 90%, 91%, 92%, 93%, 94%, 95%, 96%, 97%, 98%, 99% or greater than 99% identity or similarity to SEQ ID NO: 2.

In still another embodiment, the wheat plant, wheat seed or parts of a wheat plant comprise a polynucleotide with one or more non-transgenic mutations listed in Table 1 that codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 3.

In another embodiment, the wheat plant, wheat seed or parts of the wheat plant comprise a polynucleotide with one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 5.

In still another embodiment, the wheat plant, wheat seed or parts of a wheat plant comprise a polynucleotide with one or more non-transgenic mutations that codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 6.

In another embodiment, the wheat plant, wheat seed or parts of the wheat plant comprise a polynucleotide with one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 8.

In still another embodiment, the wheat plant, wheat seed or parts of a wheat plant comprise a polynucleotide with one or more non-transgenic mutations that codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 9.

In another embodiment, the wheat plant, wheat seed or parts of a wheat plant has one or more mutations in the WPBF gene including but not limited to one or more mutations enumerated in Tables 1-3 and corresponding mutations in the homoeologues. A wheat plant, wheat seed or parts of a wheat plant can be generated having 1, 2, 3, 4, 5, 6, 7, 8, 9, 10, 11, 12, 13, 14, 15, 16, 17, 18, 19, 20, 21, 22, 23, 24, 25 or greater than 25 of the mutations disclosed herein including but not limited to the mutations disclosed in Tables 1-3, as well as mutations in corresponding homoeologues.

IX. Grain, Flour and Starch

In another embodiment, the disclosure relates to a wheat grain, flour or starch comprising one or more non-transgenic mutations in the WPBF gene or a modified WPBF gene. In another embodiment, the disclosure relates to wheat grain comprising an embryo, wherein the embryo comprises one or more non-transgenic mutations in a WPBF gene or a modified WPBF gene.

In another embodiment, the wheat grain, flour or starch comprises one or more non-transgenic mutations in the WPBF genes including but not limited to the mutations recited in Tables 1-3 and the corresponding mutations in homologues, and homoeologues.

In still another embodiment, the disclosure relates to a wheat grain or flour comprising at least one non-transgenic mutation in the WPBF gene in one, two or three genomes.

In still another embodiment, the disclosure relates to a wheat grain, flour or starch comprising one or more non-transgenic mutations in the WPBF gene of the A genome. In another embodiment, the non-transgenic mutations are identical in both alleles of the WPBF gene of the A genome.

In one embodiment, the wheat grain, flour or starch comprises one or more non-transgenic mutations in both alleles of the WPBF gene in the B genome. In another embodiment, the non-transgenic mutations are identical in both alleles of the WPBF gene of the B genome.

In one embodiment, the wheat grain, flour or starch comprises one or more non-transgenic mutations in both alleles of the WPBF gene in the D genome. In another embodiment, the non-transgenic mutations are identical in both alleles of the WPBF gene of the D genome.

In one embodiment, the disclosure relates to wheat grain, wheat flour or starch comprising a polynucleotide of the WPBF gene in the A genome with one or more non-transgenic mutations listed in Table 1 and corresponding to SEQ ID NO: 2. In another embodiment, the wheat grain or wheat flour comprise a polynucleotide with one or more non-transgenic mutations listed in Table 1 and has 85%, 86%, 87%, 88%, 89%, 90%, 91%, 92%, 93%, 94%, 95%, 96%, 97%, 98%, 99% or greater than 99% identity or similarity to SEQ ID NO: 2.

In still another embodiment, wheat grain, wheat flour or starch comprise a polynucleotide with one or more non-transgenic mutations listed in Table 1 that codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 3.

In one embodiment, the disclosure relates to wheat grain, wheat flour or starch comprising a polynucleotide of the WPBF gene in the B genome with one or more non-transgenic mutations listed in Table 2 and corresponding to SEQ ID NO: 5. In another embodiment, the wheat grain or wheat flour comprise a polynucleotide with one or more non-transgenic mutations listed in Table 2 and has 85%, 86%, 87%, 88%, 89%, 90%, 91%, 92%, 93%, 94%, 95%, 96%, 97%, 98%, 99% or greater than 99% identity or similarity to SEQ ID NO: 5.

In still another embodiment, wheat grain, wheat flour or starch comprise a polynucleotide with one or more non-transgenic mutations listed in Table 2 that codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 6.

In one embodiment, the disclosure relates to wheat grain, wheat flour or starch comprising a polynucleotide of the WPBF gene in the D genome with one or more non-transgenic mutations listed in Table 3 and corresponding to SEQ ID NO: 8. In another embodiment, the wheat grain or wheat flour comprise a polynucleotide with one or more non-transgenic mutations listed in Table 3 and has 85%, 86%, 87%, 88%, 89%, 90%, 91%, 92%, 93%, 94%, 95%, 96%, 97%, 98%, 99% or greater than 99% identity or similarity to SEQ ID NO: 8.

In still another embodiment, wheat grain, wheat flour or starch comprise a polynucleotide with one or more non-transgenic mutations listed in Table 3 that codes for a WPBF protein, wherein the WPBF protein comprises one or more non-transgenic mutations and has 85%, 86%, 87%, 88%, 89%, 90%, 91%, 92%, 93%, 94%, 95%, 96%, 97%, 98%, 99% or greater than 99% identity or similarity to SEQ ID NO: 9.

In still another embodiment, the disclosure relates to wheat grain or flour comprising an endosperm and a reduced gene expression level, activity or expression level and activity of the WPBF gene as compared to wild type wheat grain or flour.

In yet another embodiment, the disclosure relates to wheat grain or flour with one or more mutations in the WPBF gene or a modified WPBF gene exhibiting reduced gluten grain as compared to wild type wheat grain or flour. In another embodiment, wheat grain or flour with one or more mutations in the WPBF gene or a modified WPBF gene exhibits from 1-5%, 5-10%, 10-15%, 15-20%, 20-25%, 25-30%, 30-35%, 35-40%, 45-50%, 50-55%, 55-60%, 60-65%, 65-70%, 70-75%, 75-80%, 80-85%, 85-90%, 90-95%, and greater than 95% reduced gluten as compared to wild type grain or flour.

In another embodiment, wheat grain or flour with one or more mutations in the WPBF gene or a modified WPBF gene exhibits a reduced level of gluten as compared to wild type grain, wherein the grain with mutation or modification has about 80%, or about 70%, or about 60% or about 50%, or about 40%, or about 30%, or about 20%, or about 10%, or about 5% or about 3% less gluten as compared to wild type grain.

In another embodiment, the wheat grain or flour comprises from about 5% to about 15%, or from about 15% to 25%, or from about 25% to 45%, or from about 45% to about 65%, or from about 65% to about 85%, or from about 85% to 97% less gluten as compared to wild type grain or flour.

In another embodiment, the wheat grain or flour comprises about 80% or less, about 70% or less, about 60% or less, about 50% or less, about 40% or less, about 30% or less, about 25% or less, about 20% or less, about 15% or less, about 10% or less, about 7.5% or less, about 5% or less or about 2.5% or less or about 1% or less, or about 0.5% or less of the level of low molecular weight glutenins as compared to wild type grain or flour In another embodiment, the wheat grain or flour comprises from about 5% to about 15%, or from about 15% to 25%, or from about 25% to 45%, or from about 45% to about 65%, or from 65% to about 85%, or from about 85% to 97% less gliadins as compared to wild type grain or flour.

In one embodiment, grains disclosed herein may contain embryos that are larger than wild type grains. In one embodiment, the grains disclosed herein may contain embryos that are from 1-5%, or from 5-10%, or 10-15%, or from 15-20%, or from 20-25%, or from 25-50%, or from 50-75%, or from 75-95% larger than embryos of wild type grains In one embodiment, the grains disclosed herein may contain embryos that are at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, and at least 90% greater in size than embryos of wild type grains.

In yet another embodiment, the grains disclosed herein may contain more lipid as compared to wild type grains. In one embodiment, the grains disclosed herein may contain from 1-5%, or from 5-10%, or 10-15%, or from 15-20%, or from 20-25%, or from 25-50%, or from 50-75%, or from 75-95% more lipid than wild type grains.

In one embodiment, the grains disclosed herein may contain at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, and at least 90% more lipid than wild type grains.

In still another embodiment, the grains disclosed herein may contain more free lysine or lysine incorporated into proteins as compared to wild type grain. This may result in these grains providing a higher level of the essential amino acid lysine to mono-gastric animals including humans than the corresponding wild type grain.

In one embodiment, the grains disclosed herein may contain from 1-5%, or from 5-10%, or 10-1.5%, or from 15-20%, or from 20-25% or from 25-50%, or from 50-75%, or from 75-95% more free lysine than wild type grains.

In one embodiment the grains disclosed herein may contain at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, and at least 90% more free lysine than wild type grains.

In still another embodiment, the grains disclosed herein may contain more lysine incorporated into protein as compared to wild type grain. In one embodiment, the grains disclosed herein may contain from 1-5%, or from 5-10%, or 10-15%, or from 15-20%, or from 20-25%, or from 25-50%, or from 50-75%, or from 75-95%, more lysine incorporated into proteins than wild type grains.

In one embodiment, the grains disclosed herein may contain at least 5%, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, and at least 90% more lysine incorporated into proteins than wild type grains.

In one embodiment, grains disclosed herein may contain less starch as compared to wild type grains. In one embodiment, grains disclosed herein may contain from 1-5%, from 5-10%, from 10-15%, from 15-20%, from 20-25% less starch as compared to wild type grains.

In one embodiment, grains disclosed herein may have a smaller endosperm as compared to wild type grains. In one embodiment, grains disclosed may have an endosperm that is from 1-5%, from 5-10%, from 10-15%, from 15-20%, from 20-25% smaller than the endosperm of wild type grains.

In a further embodiment, the coeliac toxicity of wheat or barley grain or flour produced from the grain is less than about 50%, less than about 25%, less than about 10%, of flour produced from grain of a corresponding wild-type wheat or barley plant.

X. Food Products

In one embodiment, the disclosure is directed to a flour or other product produced from the grain or flour discussed above. In another embodiment, the flour, the coarse fraction or purified starch may be a component of a food product.

The food product includes but is not limited to a bagel, a biscuit, a bread, a bun, a croissant, a dumpling, an English muffin, a muffin, a pita bread, a quickbread, a flat bread, a sourdough bread, a refrigerated/frozen dough product, dough, baked beans, a burrito, chili, a taco, a tamale, a tortilla, a pot pie, a ready to eat cereal, a ready to eat meal, stuffing, a microwaveable meal, a brownie, a cake, a cheesecake, a coffee cake, a cookie, a dessert, a pastry, a sweet roll, a candy bar, a pie crust, pie filling, baby food, a baking mix, a batter, a breading, a gravy mix, a meat extender, a meat substitute, a seasoning mix, a soup mix, a gravy, a roux, a salad dressing, a soup, sour cream, a noodle, a pasta, ramen noodles, chow mein noodles, lo mein noodles, an ice cream inclusion, an ice cream bar, an ice cream cone, an ice cream sandwich, a cracker, a crouton, a doughnut, an egg roll, an extruded snack, a fruit and grain bar, a microwaveable snack product, a nutritional bar, a pancake, a par-baked bakery product, a pretzel, a pudding, a granola-based product, a snack chip, a snack food, a snack mix, a waffle, a pizza crust, animal food or pet food.

In one embodiment, the flour is a whole grain flour (ex.—an ultrafine-milled whole grain flour, such as an ultrafine-milled whole grain wheat flour). In one embodiment, the whole grain flour includes a refined flour constituent (ex.—refined wheat flour or refined flour) and a coarse fraction (ex.—an ultrafine-milled coarse fraction). Refined wheat flour may be flour which is prepared, for example, by grinding and bolting (sifting) cleaned wheat. The Food and Drug Administration (FDA) requires flour to meet certain particle size standards in order to be included in the category of refined wheat flour. The particle size of refined wheat flour is described as flour in which not less than 98% passes through a cloth having openings not larger than those of woven wire cloth designated "212 micrometers (U.S. Wire 70)."

In another embodiment, the coarse fraction includes at least one of: bran and germ. For instance, the germ is an embryonic plant found within the wheat kernel. The germ includes lipids, fiber, vitamins, protein, minerals and phytonutrients, such as flavonoids. The bran may include several cell layers and has a significant amount of lipids, fiber, vitamins, protein, minerals and phytonutrients, such as flavonoids.

For example, the coarse fraction or whole grain flour or refined flour of the present invention may be used in various amounts to replace refined or whole grain flour in baked goods, snack products, and food products. The whole grain flour (i.e.—ultrafine-milled whole grain flour) may also be marketed directly to consumers for use in their homemade baked products. In an exemplary embodiment, a granulation profile of the whole grain flour is such that 98% of particles by weight of the whole grain flour are less than 212 micrometers.

In another embodiment, the whole grain flour or coarse fraction or refined flour may be a component of a nutritional supplement. The nutritional supplement may be a product that is added to the diet containing one or more ingredients, typically including: vitamins, minerals, herbs, amino acids, enzymes, antioxidants, herbs, spices, probiotics, extracts, prebiotics and fiber.

In a further embodiment, the nutritional supplement may include any known nutritional ingredients that will aid in the overall health of an individual, examples include but are not limited to vitamins, minerals, other fiber components, fatty acids, antioxidants, amino acids, peptides, proteins, lutein, ribose, omega-3 fatty acids, and/or other nutritional ingredients. Because of the high nutritional content of the endosperm of the present invention, there may be many uses that confer numerous benefits to an individual, including, delivery of fiber and other essential nutrients, increased digestive function and health, weight management, blood sugar management, heart health, diabetes risk reduction, potential arthritis risk reduction, and overall health and wellness for an individual.

In still another embodiments, the whole grain flour or coarse fraction or refined flour may be a component of a dietary supplement. The Code of Federal Regulations defines a dietary supplement as a product that is intended to supplement the diet and contains one or more dietary ingredients including: vitamins, minerals, herbs, botanicals, amino acids, and other substances or their constituents; is intended to be taken by mouth as a pill, capsule, tablet, or liquid; and is labeled on the front panel as being a dietary supplement.

In yet another embodiment, the whole grain flour or coarse fraction or refined flour may be a fiber supplement or a component thereof. The fiber supplement may be delivered in, but is not limited to the following forms: instant beverage mixes, ready-to-drink beverages, nutritional bars, wafers, cookies, crackers, gel shots, capsules, chews, chewable tablets, and pills. One embodiment delivers the fiber supplement in the form of a flavored shake or malt type beverage.

In another embodiment, the whole grain flour or coarse fraction or refined flour may be included as a component of a digestive supplement. The whole grain flour or coarse fraction or refined flour may be a component of a digestive supplement alone or in combination with one or more prebiotic compounds and/or probiotic organisms. Prebiotic compounds are non-digestible food ingredients that may beneficially affect the host by selectively stimulating the growth and/or the activity of a limited number of microorganisms in the colon. Examples of prebiotic compounds within the scope of the invention, may include, but are not limited to: oligosaccharides and inulins.

Probiotics are microorganisms which, when administered in adequate amounts, confer a health benefit on the host. Probiotic organisms include, but are not limited to: *Lactobacillus, Bifidobacteria, Escherichia, Clostridium, Lactococcus, Streptococcus, Enterococcus*, and *Saccharomyces*.

In yet another embodiment, the whole grain flour or coarse fraction or refined flour may be included as a component of a functional food. The Institute of Food Technologists defines functional foods as, foods and food components that provide a health benefit beyond basic nutrition. This includes conventional foods, fortified, enriched, or enhanced foods, and dietary supplements. The whole grain flour and coarse fraction or refined flour include numerous vitamins and minerals, have high oxygen radical absorption capacities, and are high in fiber, making them suited for use in/as a functional food.

In another embodiment, the whole grain flour or coarse fraction or refined flour may be used in medical foods. Medical food is defined as a food that is formulated to be consumed or administered entirely under the supervision of a physician and which is intended for the specific dietary management of a disease or condition for which distinctive nutritional requirements, based on recognized scientific principles, are established by medical evaluation. The nutrient contents and antioxidant capacities of the whole grain flour and coarse fraction or refined flour make them ideal for use in medical foods.

In yet another embodiment, the whole grain flour or coarse fraction or refined flour may also be used in pharmaceuticals. The whole grain flour and coarse fraction or refined flour are high in fiber and have a very fine granulation making them suitable for use as a carrier in pharmaceuticals.

In still another embodiment, delivery of the whole grain flour or coarse fraction or refined flour as a nutritional supplement, dietary supplement or digestive supplement is contemplated via delivery mechanisms where the whole grain flour or coarse fraction is the single ingredient or one of many nutritional ingredients. Examples include but are not limited to: instant beverage mixes, ready-to-drink beverages, nutritional bars, wafers, cookies, crackers, gel shots, capsules, and chews.

In yet another embodiment, a milling process may be used to make a multi-wheat flour, or a multi-grain coarse fraction. In one embodiment, bran and germ from one type of wheat may be ground and blended with ground endosperm or whole grain wheat flour of another type of wheat. Alternatively bran and germ of one type of grain may be ground and blended with ground endosperm or whole grain flour of another type of grain.

In still another embodiment, bran and germ from a first type of wheat or grain may be blended with bran and germ from a second type of wheat or grain to produce a multi-grain coarse fraction. It is contemplated that the invention encompasses mixing any combination of one or more of bran, germ, endosperm, and whole grain flour of one or more grains. This multi-grain, multi-wheat approach may be used to make custom flour and capitalize on the qualities and nutritional contents of multiple types of grains or wheats to make one flour.

The whole grain flour of the invention may be produced via a variety of milling processes. One exemplary process involves grinding grain in a single stream without separating endosperm, bran, and germ of the grain into separate streams. Clean and tempered grain is conveyed to a first passage grinder, such as a hammermill, roller mill, pin mill, impact mill, disc mill, air attrition mill, gap mill, or the like.

After grinding, the grain is discharged and conveyed to a sifter. Any sifter known in the art for sifting a ground particle may be used. Material passing through the screen of the sifter is the whole grain flour of the invention and requires no further processing. Material that remains on the screen is referred to as a second fraction. The second fraction requires additional particle reduction. Thus, this second fraction may be conveyed to a second passage grinder.

After grinding, the second fraction may be conveyed to a second sifter. Material passing through the screen of the second sifter is the whole grain flour. The material that remains on the screen is referred to as the fourth fraction and requires further processing to reduce the particle size. The fourth fraction on the screen of the second sifter is conveyed back into either the first passage grinder or the second passage grinder for further processing via a feedback loop.

It is contemplated that the whole grain flour, coarse fraction, purified starch and/or grain products of the invention may be produced by a number of milling processes known in the art.

XI. Glutenase

In one embodiment, the wheat plant, wheat seeds, and parts of the wheat plant disclosed herein can be mixed with a glutenase.

In still another embodiment, the grain, flour, and starch disclosed herein can be mixed with a glutenase. In another embodiment, a food product disclosed herein can be mixed with a glutenase.

In one embodiment, the disclosure is directed to a flour or other product comprised of the grain or flour discussed above and a glutenase. In another embodiment, a composition of the flour, either the coarse fraction or purified starch and a glutenase may be a component of a food product.

As used herein, the term "glutenase" refers to an enzyme that is capable, alone or in combination with endogenous or exogenously added enzymes, of cleaving toxic oligopeptides of gluten proteins of wheat, barley, oats and rye into non-toxic fragments. Gluten is the protein fraction in cereal dough, which can be subdivided into glutenins and prolamines, which are subclassified as gliadins, secalins, hordeins, and avenins from wheat, rye, barley and oat, respectively.

In one embodiment, the term "glutenase" may also refer to a protease or a peptidase enzyme. The term "protease" or "peptidase" describe a protein or fragment thereof with the capability of cleaving peptide bonds, where the scissile peptide bond may either be terminal or internal in oligopeptides or larger proteins. Prolyl-specific peptidases are glutenases.

Glutenases include protease and peptidase enzymes having at least about 20% sequence identity at the amino acid level, more usually at least about 40% sequence identity, and preferably at least about 70% sequence identity to one of the following peptidases: prolyl endopeptidase (PEP) from *F. meningosepticum* (Genbank accession number D10980), PEP from *A. hydrophila* (Genbank accession number D14005), PEP form *S. capisulata* (Genbank accession number AB010298), DCP I from rabbit (Genbank accession number X62551), DPP IV from *Aspergillus fumigatus* (Genbank accession number U87950) or cysteine proteinase B from *Hordeum vulgare* (Genbank accession number JQ1110).

In one embodiment, the glutenase is a PEP. PEPs are produced in microorganisms, plants and animals. PEPs belong to the serine protease superfamily of enzymes and have a conserved catalytic triad composed of a Ser, His, and Asp residues. Some of these homologs have been characterized, e.g. the enzymes from *F. meningoscepticum, Aeromonas hydrophila, Aeromonas punctata, Novosphingobium capsulatum, Pyrococcus furiosus and from mammalian sources are biochemically characterized PEPs. Others such as the Nostoc and Arabidopsis enzymes are likely to be PEPs but have not been fully characterized to date. Yet others, such as the E. coli and M. xanthus enzymes*, may not be PEPs but are homologous members of the serine protease superfamily, and can be useful starting materials in protein engineering to make a PEP. Relative to the *F. meningoscepticum* enzyme, the pairwise sequence identity of this family of enzymes is in the 30-60% range. Accordingly, PEPs include enzymes having >30% identity to the *F. meningoscepticum* enzyme (as in the *Pyrococcus* enzymes), or having >40% identity (as in the *Novosphingobium* enzymes), or having >50% identity (as in the *Aeromonas* enzymes) to the *F. meningoscepticum* enzyme.

In one embodiment, a glutenase includes a peptidase or protease that has a specific activity of at least 2.5 U/mg, preferably 25 U/mg and more preferably 250 U/mg for cleavage of a peptide comprising one of more of the following motifs: Gly-Pro-pNA, Z-Gly-Pro-pNA (where Z is a benzyloxycarbonyl group), and Hip-His-Leu, where is hippuric acid, pNA is para-nitroanilide, and 1 U is the amount of enzyme required to catalyze the turnover of 1 µmole of substrate per minute.

In one embodiment, the glutenase is Kuma030, which is a gliadin peptidase that rapidly degrades immunogenic gliadin peptides as described in Journal of the American Chemical Society, 137:13106-13113, 2015. In another embodiment, the glutenase is KumaMax (Kuma010).

In still another embodiment, a glutenase useful in the compositions and methods disclosed herein includes an enzyme belonging to any of the following enzyme classifications: EC 3.4.21.26, EC 3.4.14.5, or EC 3.4.15.1.

In one embodiment, the amino acid sequence of a glutenase, e.g. a naturally occurring glutenase, can be altered in various ways known in the art to generate targeted changes in sequence and additional glutenase enzymes useful in the formulations and compositions disclosed herein. Such variants will typically be functionally-preserved variants, which differ, usually in sequence, from the corresponding native or parent protein but still retain the desired biological activity.

Variants also include fragments of a glutenase that retain enzymatic activity. Various methods known in the art can be used to generate targeted changes, e.g: phage display in combination with random and targeted mutations, introduction of scanning mutations, and the like. A variant can be substantially similar to a native sequence, i.e. differing by at least one amino acid, and can differ by at least two but usually not more than about ten amino acids (the number of differences depending on the size of the native sequence). The sequence changes may be substitutions, insertions or deletions. Scanning mutations that systematically introduce alanine, or other residues, may be used to determine key amino acids. Conservative amino acid substitutions typically include substitutions within the following groups: (glycine, alanine); (valine, isoleucine, leucine); (aspartic acid, glutamic acid); (asparagine, glutamine); (serine, threonine); (lysine, arginine); and (phenylalanine, tyrosine).

In another embodiment, glutenase fragments of interest include fragments of at least about 20 contiguous amino acids, more usually at least about 50 contiguous amino acids, and may comprise 100 or more amino acids, up to the complete protein, and may extend further to comprise additional sequences. In each case, the key criterion is whether the fragment retains the ability to digest the toxic oligopeptides that contribute to the symptoms of Celiac Sprue.

XII. Plant Breeding

In another embodiment, the disclosure is directed to methods for plant breeding using wheat plants and plant parts with one or more non-transgenic mutations in the WPBF gene.

One such embodiment is the method of crossing a wheat variety with one or more non-transgenic mutations in the WPBF gene with another variety of wheat to form a first generation population of F1 plants. The population of first generation F1 plants produced by this method is also an embodiment of the invention. This first generation population of F1 plants will comprise an essentially complete set of the alleles of a wheat variety with one or more non-transgenic mutations in the WPBF gene. One of ordinary skill in the art can utilize either breeder books or molecular methods to identify a particular F1 plant produced using a wheat variety with one or more non-transgenic mutations in the WPBF gene, and any such individual plant is also encompassed by this invention. These embodiments also cover use of transgenic or backcross conversions of wheat varieties with one or more mutations in the WPBF gene to produce first generation F1 plants.

In another embodiment, the disclosure relates to a method of developing a progeny wheat plant. A method of developing a progeny wheat plant comprises crossing a wheat variety with one or more non-transgenic mutations in the WPBF gene with a second wheat plant and performing a breeding method. A specific method for producing a line derived from a wheat variety with one or more non-transgenic mutations in the WPBF gene is as follows.

One of ordinary skill in the art would cross a wheat variety with one or more non-transgenic mutations in the WPBF gene with another variety of wheat, such as an elite variety. The F1 seed derived from this cross would be grown to form a homogeneous population. The F1 seed would contain one set of the alleles from a wheat variety with one or more non-transgenic mutations in the WPBF gene and one set of the alleles from the other wheat variety.

The F1 genome would be made-up of 50% of a wheat variety with one or more non-transgenic mutations in the WPBF gene and 50% of the other elite variety. The F1 seed would be grown to form F2 seed. The F1 seed could be allowed to self, or bred with another wheat cultivar.

On average the F2 seed would have derived 50% of its alleles from a wheat variety with one or more non-transgenic mutations in the WPBF gene and 50% from the other wheat variety, but various individual plants from the population would have a much greater percentage of their alleles derived from a wheat variety with one or more non-transgenic mutations in the WPBF gene (Wang J. and R. Bernardo, 2000, Crop Sci. 40:659-665 and Bernardo, R. and A. L. Kahler, 2001, Theor. Appl. Genet. 102:986-992).

The F2 seed would be grown and selection of plants would be made based on visual observation and/or measurement of traits and/or marker assisted selection. The wheat variety with one or more non-transgenic mutations in the WPBF gene-derived progeny that exhibit gene-derived traits would be selected and each plant would be harvested separately. This F3 seed from each plant would be grown in individual rows and allowed to self. Then selected rows or plants from the rows would be harvested and threshed individually. The selections would again be based on visual observation and/or measurements for desirable traits of the plants, such as one or more of the desirable wheat variety with one or more non-transgenic mutations in the WPBF gene-derived traits.

The process of growing and selection would be repeated any number of times until a homozygous wheat variety with one or more non-transgenic mutations in the WPBF gene-derived wheat plant is obtained. The homozygous wheat variety with one or more non-transgenic mutations in the WPBF gene-derived wheat plant would contain desirable traits derived from the wheat variety with one or more non-transgenic mutations in the WPBF gene, some of which may not have been expressed by the other original wheat variety to which the wheat variety with one or more non-transgenic mutations in the WPBF gene was crossed and some of which may have been expressed by both wheat varieties but now would be at a level equal to or greater than the level expressed in the wheat variety with one or more non-transgenic mutations in the WPBF gene.

The breeding process, of crossing, selfing, and selection may be repeated to produce another population of wheat variety with one or more non-transgenic mutations in the WPBF gene-derived wheat plants with, on average, 25% of their genes derived from wheat variety with one or more non-transgenic mutations in the WPBF gene, but various individual plants from the population would have a much greater percentage of their alleles derived from the wheat variety with one or more non-transgenic mutations in the WPBF gene. Another embodiment of the invention is a homozygous wheat variety with one or more non-transgenic mutations in the WPBF gene-derived wheat plant that has been crossed with another wheat plant with one or more non-transgenic mutations in the WPBF gene-derived traits.

A. Mutations as Markers

Genetic markers are the biological features that are determined by allelic forms of genes or ge-netic loci and can be transmitted from one generation to another, and thus they can be used as experimental probes or tags to keep track of an individual, a plant, a tissue, a cell, a nucleus, a chromosome or a gene. Genetic markers used in genetics and plant breeding can be classified into two categories: classical markers and DNA markers. Classical markers include morphological markers, cytological markers and biochemical markers. DNA markers have developed into many systems based on different polymorphism detecting techniques or methods (southern blotting—nuclear acid hybridization, PCR, and DNA sequencing), such as restriction fragment length polymorphism (RFLP), amplified fragment length polymorphism (AFLP), random amplified polymorphic DNA (RAPD), simple sequence repeat (SSR), single nucleotide polymorphism (SNP), etc.

SNPs provide the ultimate/simplest form of molecular markers as a single nucleotide base is the smallest unit of inheritance, and thus they can provide the maximum number of markers. SNPs occur very commonly in animals and plants. Typically, SNP frequencies are in a range of one SNP every 100-300 base pairs in plants. SNPs may be present within coding sequences of genes, non-coding regions of genes or in the intergenic regions between genes at different frequencies in different chromosome regions.

SNPs are co-dominant markers, often linked to genes and present in the simplest/ultimate form for polymorphism, and thus they have become very attractive and potential genetic markers in genetic study and breeding. Moreover, SNPs can be very easily automated and quickly detected, with a high efficiency for detection of polymorphisms.

In one embodiment, the disclosure relates to mutations in the WPBF gene, which are single nucleotide polymorphisms, that can be used as markers in plant breeding. The mutations in the WPBF gene are causative and their segregation can be followed using, for example, KASP probes.

In another embodiment, mutations identified in Section II of this disclosure can be used as markers in plant breeding. In yet another embodiment, one or more mutations in Tables 1-3 can be used as markers in plant breeding.

In one embodiment, the mutations can be followed using techniques including but not limited to SNP-Restriction Fragment Length Polymorphism (RFLP); CAPS; Axiom SNP Arrays; iSelect Array; TaqMan Probes, and KASP Probes. In another embodiment, Next Generation Sequencing techniques can be used including but not limited to 454 Life Sciences (Roche Applied Science, Indianapolis, Ind.); HiSeq (Illumina, San Diego, Calif.); SOLiD and Ion Torrent (Life Technologies Corp., Carlsbad, Calif.).

PCR-based KASP™ genotyping assay is a homogeneous, fluorescence (FRET) based assay that enables accurate bi-allelic discrimination of known SNPs and InDels. A key feature of PCR-based KASP technology is the use of a universal FRET cassette reporter system that eliminates the need for costly dual-labelled probes. The allele-specific forward primers each have a proprietary tail sequence that corresponds with one of two FRET cassettes: one label with FAM dye and the other with HEX dye. Bi-allelic discrimination is achieved through competitive binding of two allele-specific forward primers.

XIII. Barley Transcript MLOC_12852.2, a Dof Transcription Factor

Barley is a diploid cereal that is widely grown in cooler climates for food, beverage, and animal feed production. Barley seed proteins are classified into albumin, globulin, prolamin (hordein) and glutelin according to their solubility in water, salt solution, aqueous alcohol and basic or acid solutions, respectively. Approximately half of the seed storage proteins in barley are found in the prolamin fraction. These prolamins are primarily reserve proteins that function as sources of carbon, nitrogen or sulphur for growth and development following germination. Hordein constitutes about 40% of the seed protein, although this is dependent on the nitrogen supply of the plant during growth.

The loci encoding the barley prolamins have been characterized, mostly because of their contribution to barley malting quality and foam formation and haze in beer production. There are four classes of prolamins in barley, the B, C. D and γ-hordeins encoded by the Hor2, Hor1, Hor3, and Hor5 loci, respectively, on chromosome 1H. These loci encode proteins that vary from a single prolamin (e.g. D hordein) to protein families containing 20-30 members e.g. B and C hordeins). The B and C hordeins are relatively more abundant, comprising about 70% and 24% of the total hordeins, respectively. The D and γ-hordeins represent minor components at about 2-4% each. The molecular weight of hordeins varies from about 35 kDa, to 100 kDa. There are no barley prolamins, which have close homology to wheat α-gliadins, however it is widely accepted that hordeins are toxic to coeliacs.

The B hordeins are the main protein fraction, differing from C hordeins in their sulfur content. B hordeins account for 70-80% of the total and C hordeins for 10-20%. The A hordeins are not generally considered to be a storage fraction whereas D hordeins are homologous to the high-molecular-weight glutenins. Hordeins, along with the rest of the related cereal prolamins, are not expressed in the zygotic embryo itself; unlike other storage proteins such as napins; they are believed to be expressed exclusively in the starchy endosperm during the middle-to-late stages of seed development.

In the US, the FDA definition of "gluten free" requires the product to be made from gluten-free raw materials only, i.e. containing no wheat, barley or rye whatsoever. The Codex Alimentarius permits the "gluten-free" label on foods containing no more than 20 ppm of gluten (0.02 g per kilogram or liter) and this is also the European standard for "gluten-free." Most coeliacs can tolerate up to about 10 mg of gluten per day without major effect (Thompson, 2001).

Examples of a wild-type barley plant include, but are not limited to, Bomi, Sloop, Carlsberg II, K8 or L1.

In another embodiment, the disclosure relates to barley plants with one or more non-transgenic mutations in the Barley transcript MLOC_12852.2, which is a Dof transcription factor (herein after "barley Dof transcription factor"). In another embodiment, the disclosure relates to barley plants with one or more non-transgenic mutations in the barley Dof transcription factor gene, wherein said mutations result in grains with reduced gluten.

In one embodiment, the disclosure relates to a barley plant with reduced expression of the barley Dof transcription factor gene or reduced activity of the barley DoF transcription factor protein. In one embodiment, reducing expression of the barley DoF transcription factor gene or barley Dof transcription factor protein can be accomplished by non-transgenic mutations, transgenes, or genomic editing.

In one embodiment, the disclosure relates to modifying the barley DoF transcription factor gene through non-transgenic mutations, or transgenes or genomic editing. The methods and techniques described in Sections III and IV apply equally to barley plants.

In another embodiment, the disclosure relates to barley plants with a reduced level of total hordeins as compared to the total level of hordeins in a wild type plant. In one embodiment, the barley plant has at least one of the B, C, or D hordeins reduced as compared to the B, C, or D hordeins in a wild type plant.

In still another embodiment, the disclosure relates to one or more mutations in the barley Dof transcription factor gene that reduce the level of B and/or C hordeins in grain. In yet another embodiment, the disclosure relates a barley plant with one or more mutations in the barley Dof transcription factor gene that reduce the level of B and/or C hordeins and has a wild-type level of D hordeins.

In another embodiment, the grain comprises about 75% or less, about 50% or less, about 25% or less, about 20% or less, about 15% or less, about 10% or less, about 7.5% or less, about 5% or less or about 2.5% or less of the level of B, C and/or D hordeins or any combinations thereof when compared to grain of the corresponding wild-type barley plant.

In yet another embodiment, flour produced from the grain comprises less than about 60%, or less than about 50%, or less than about 40%, or less than about 30%, or less than about 25%, or less than about 20%, or less than about 15%, or less than about 10%, or less than about 5% hordeins as compared to flour produced from wild type grain.

In a further embodiment, the coeliac, toxicity of flour produced from the grain is less than about 50%, less than about 25%, more preferably about 10% or less, of flour produced from grain of a corresponding wild-type barley plant.

In yet another embodiment, malt produced from the grain comprises less than about 200 ppm hordeins, less than about 125 ppm hordeins, more preferably less than about 75 ppm hordeins.

In yet another embodiment, the disclosure relates to one or more mutations in the barley Dof transcription factor gene. In one embodiment, the disclosure relates to multiple non-transgenic mutations in the barley Dof transcription factor gene including but not limited to 1, 2, 3, 4, 5, 6, 7, 8, 9, 10, and greater than 10 mutations.

In one embodiment, the disclosure relates to one or more mutations in the Dof region of the barley Dof transcription factor gene. In another embodiment, the disclosure relates to one or more modifications in the Dof region of the barley Dof transcription factor gene, wherein the modifications include but are not limited to mutations, non-transgenic mutations, transgenes, and modifications through genomic editing.

In still another embodiment, the disclosure relates to a barley plant with one or more mutations in the barley Dof transcription factor gene. In yet another embodiment, disclosure relates to a barley plant with one or more mutations in the Dof region of the barley Dof transcription factor gene.

In still another embodiment, the disclosure relates to a barley plant with a modified barley Dof transcription factor gene. In yet another embodiment, disclosure relates to a barley plant with a modified barley Dof transcription factor gene, wherein the modification is in the Dof region.

In one embodiment, the disclosure relates to one or more mutations in the coding sequence of SEQ ID NO. 12 for the barley Dof transcription factor. In one embodiment, the mutation is an adenine to a thymidine mutation at position 173 of SEQ ID NO. 12.

In yet another embodiment, the disclosure relates to one or more mutations in the amino acid of SEQ ID NO. 13 for the barley Dof transcription factor. One or more of the 337 amino acids shown in SEQ ID NO. 13 can be mutated. The mutations can be severe or conservative.

In one embodiment, the mutation is a Q to L mutation at amino acid 58 of SEQ ID NO. 13.

SEQ ID NO. 12: Barley (Hordeum vulgare; Hv) DOF gene:
Atggaggaagtgttttcgtccaactccaagagcaaggccggtcagatggc gggagaggcggtggcggcggccgagaagaagtctcggccgaagccagagc agaaggtggagtgccctcggtgcaagtctggtaacaccaagttctgctac tacaacaactacagcatgtcccagccgcgctacttctgcaaggcctgccg ccgctactggacccatggtggctccctccgcaacgtccccatcggtggtg gttgccgcaagcccaaacgcccggggacctctgacgcccacaagctcggc atggcctcctcatcggaacccacgggtgtcgtgcccccctcgaactgcac agggatgaacttgctaacgtcctcccgacgtttatgtctggtggctttga cattcaaagcagcctctccctgacaacttttgggtcatcatcctcatcca acccgacggggttgatgtccccggtgggacgacttcatttctggatgtg ctgagaggtggtgcaggagggcttcttgatggcagcctcggtccaaacaa tggctactactatggtgggcatgccaatggatcaggcattgggatgttga tgactccgccaacggtatcgtttggcattccaagtccgatgcaacaacat ggcggtctcgtggttggtggaaatggaataggtggcacaacttcttcaac atttcagggcaacgctggcgaggaaggagacgatggtacggggtccatta tggggctccagtggcagccacatgttggtaatggtggcggtggtggtgtt ggattaggaggcgcgcatcatcttgggactgggaacaatgtgacgatggg caacaacaacaataataacaaccagaacaacaataacggcggcggtgctg gtgatgacgacgatggtgggtcatcgagggattgctactggatcaacaat ggaggatcgaacccatggcagagcctcctcaacagcacctccctgatctc atacacacca SEQ ID NO. 13: Protein sequence of SEQ ID NO. 12
MEEVFSSNSKSKAGQMAGEAVAAAEKKSRPKPEQKVECPRCKSGNTKFCY

YNNYSMSQPRYFCKACRRYWTHGGSLRNVPIGGGCRKPKR

PGTSDAHKLGMASSSEPTGVVPPSNCTGMNFANVLPTFMSGGFDIQSSLS

LTTFGSSSSSNPTGLMSPGGTTSFLDVLRGGAGGLLDGSL

GPNNGYYYGGHANGSGIGMLMTPPTVSFGIPSPMQQHGGLVVGGNGIGGT

TSSTFQGNAGEEGDDGTGSIMGLQWQPHVGNGGGGGVGLG

GAHHLGTGNNVTMGNNNNNNNQNNNNGGGAGDDDDGGSSRDCYWINNGGS

NPWQSLLNSTSLISYTP

In one embodiment, the plants, plant parts, and compositions disclosed herein are described in non-limiting fashion in the following paragraphs:

1. A wheat plant comprising a mutation in a WPBF gene in at least one of the A, B, or D genomes, wherein the mutation contributes to grain from said wheat plant having reduced gluten as compared to grain from a wild type plant.

2. A wheat plant comprising a mutation in the Dof region of a WPBF gene in at least one of the A, B, or D genomes, wherein the mutation contributes to grain from said wheat plant having reduced gluten as compared to grain from a wild type plant.

3. A plant comprising a mutation in the Dof region of a transcription factor gene, wherein the mutation contributes to grain from said plant having reduced gluten as compared to grain from a wild type plant.

4. The wheat plant of any of the preceding paragraphs, wherein the mutation in the WPBF gene is in the B and D genomes.

5. The wheat plant of any of the preceding paragraphs, wherein the mutation in the WPBF gene is in the A and B genomes.

6. The wheat plant of any of the preceding paragraphs, wherein the mutation in the WPBF gene is in the A and D genomes.

7. The wheat plant of any of the preceding paragraphs, wherein the mutation in the WPBF gene is in the A, B, and D genomes.

8. The wheat plant of any of the preceding paragraphs, wherein the mutation results in reduced low molecular weight glutenins in grain from said wheat plant relative to a wild-type wheat plant.

9. The wheat plant of any of the preceding paragraphs, wherein the mutation results in reduced gliadins in grain from said wheat plant relative to a wild-type grain.

10. The wheat plant of any of the preceding paragraphs, wherein the mutation results in increased or unaltered high molecular weight glutenins in grain from said wheat plant relative to a wild-type grain.

11. The wheat plant of any of the preceding paragraphs, wherein the mutation results in grain from said wheat plant having reduced gluten selected from the group consisting of: about 70%, about 60%, about 50%, about 40%, about 30%, about 20%, about 10, and about 5% of the gluten found in wild type grain.

12. The wheat plant of any of the preceding paragraphs, wherein said wheat plant is homozygous for the mutation.

13. The wheat plant of any of the preceding paragraphs, which is *Triticum aestivum* ssp. *aestivum*.

14. The wheat plant of any of the preceding paragraphs, which is *Triticum turgidum* subsp. *durum*

15. The wheat plant of any of the preceding paragraphs, wherein the mutation is recited in Tables 1-3.

16. Wheat grain from the wheat plant of any of the preceding paragraphs.

17. Flour comprising the wheat grain of any of the preceding paragraphs.

18. A food product comprising a component of the wheat plant of any of the preceding paragraphs.

19. A wheat seed, plant part or progeny thereof from the wheat plant of any of the preceding paragraphs.

20. A transgenic wheat plant comprising a transgene that reduces expression of a WPBF gene and/or reduces activity of a WPBF protein, wherein the reduced expression and/or reduced activity contributes to grain from said wheat plant having reduced gluten as compared to grain from a wild type plant.

21. The wheat plant of paragraph 20, wherein the transgene results in reduced low molecular weight glutenins in grain from said wheat plant relative to a wild-type wheat plant.

22. The wheat plant of paragraph 20, wherein the transgene results in reduced gliadins in grain from said wheat plant relative to a wild-type grain.

23. The wheat plant of paragraph 20, wherein the transgene results in increased or unaltered high molecular weight glutenins in grain from said wheat plant relative to a wild-type grain.

24. The wheat plant of paragraph 20, wherein the transgene results in grain from said wheat plant having reduced gluten selected from the group consisting of: about 70%, about 60%, about 50%, about 40%, about 30%, about 20%, about 10, and about 5% of the gluten found in wild type grain.

25. The wheat plant of paragraph 20, which is *Triticum aestivum* ssp. *aestivum*.

26. The wheat plant of paragraph 20, which is *Triticum turgidum* subsp. *durum*

27. Wheat grain from the wheat plant of any of paragraphs 20-26.

28. Flour comprising the wheat grain of paragraph 27.

29. A food product comprising a component of the wheat plant of paragraphs 20-28.

30. A wheat seed, plant part or progeny thereof from the wheat plant of paragraphs 20-26.

31. A wheat plant comprising a modified WPBF gene, wherein the WPBF gene was modified by genomic editing, and said modification contributes to grain having reduced gluten as compared to grain from a wild type plant.

32. The wheat plant of paragraph 31, wherein the modified WPBF results in reduced low molecular weight glutenins in grain from said wheat plant relative to a wild-type wheat plant.

33. The wheat plant of paragraph 31, wherein the modified WPBF gene results in reduced gliadins in grain from said wheat plant relative to a wild-type grain.

34. The wheat plant of paragraph 31, wherein the modified WPBF gene results in increased or unaltered high molecular weight glutenins in grain from said wheat plant relative to a wild-type grain.

35. The wheat plant of paragraph 31, wherein the modified WPBF gene results in grain from said wheat plant having reduced gluten selected from the group consisting of: about 70%, about 60%, about 50%, about 40%, about 30%, about 20%, about 10, and about 5% of the gluten found in wild type grain.

36. The wheat plant of paragraph 31, which is *Triticum aestivum* ssp. *aestivum*.

37. The wheat plant of paragraph 31, which is *Triticum turgidum* subsp. *durum*

38. Wheat grain from the wheat plant of any of paragraphs 31-37.

39. Flour comprising the wheat grain of paragraph 38.

40. A food product comprising a component of the wheat plant of paragraphs 31-39.

41. A wheat seed, plant part or progeny thereof from the wheat plant of paragraphs 31-37.

42. A barley plant comprising one or more mutations in Barley transcript MLOC_12852.2, wherein the one or more mutations contributes to grain from said barley plant having reduced gluten as compared to grain from a wild type plant.

43. A barley plant comprising a modified Barley transcript MLOC_12852.2, wherein the modification contributes to grain from said barley plant having reduced gluten as compared to grain from a wild type plant.

44. A barley plant comprising a modified Barley transcript MLOC_12852.2, wherein Barley transcript MLOC_12852.2 is modified by a mutation, or a transgene, or genomic editing and further wherein the modification contributes to grain from said barley plant having reduced gluten as compared to grain from a wild type plant.

45. A barley plant comprising one or more mutations in the Dof region of Barley transcript MLOC_12852.2, wherein the one or more mutations contributes to grain from said barley plant having reduced gluten as compared to grain from a wild type plant.

46. A barley plant comprising a modification of a Dof region of Barley transcript MLOC_12852.2, wherein the modification contributes to grain from said barley plant having reduced gluten as compared to grain from a wild type plant.

47. A barley plant comprising a modification of a Dof region of Barley transcript MLOC_12852.2, wherein the Dof region of Barley transcript MLOC_12852.2 is modified by a mutation, or a transgene or genomic editing, and further wherein the modification contributes to grain from said barley plant having reduced gluten as compared to grain from a wild type plant.

48. A barley plant comprising one or more mutations in SEQ ID NO. 12, wherein the one or more mutations contributes to grain from said barley plant having reduced gluten as compared to grain from a wild type plant.

49. A barley plant comprising at least two mutations in SEQ ID NO. 12 for the barley Dof transcription factor, wherein one mutation is an adenine to a thymidine mutation at position 173 of SEQ ID NO. 12, and further wherein the mutations contribute to grain from said barley plant having reduced gluten as compared to grain from a wild type plant.

50. A barley plant comprising a mutation in SEQ ID NO. 12, wherein the mutation contributes to grain from said barley plant having reduced gluten as compared to grain from a wild type plant, and further wherein the mutation is not an adenine to a thymidine mutation at position 173 of SEQ ID NO. 12.

51. Grain from the barley plant of any of paragraphs 42-50.

52. Flour comprising the grain of paragraph 51.

53. A food product comprising a component of the barley plant of any of paragraphs 42-52.

54. A barley seed, plant part or progeny thereof from the barley plant of paragraphs 42-50.

55. A wheat plant comprising a mutation in a WPBF gene in B and D genomes, wherein the mutations contribute to grain from said wheat plant having reduced gluten as compared to grain from a wild type plant.

56. The wheat plant of paragraph 55, wherein the mutation in the B genome results in an alteration of a tryptophan to a stop codon at amino acid position of 70 (W70*) of SEQ ID No. 3.

57. The wheat plant of paragraph 55, wherein the mutation in the D genome results in a cysteine to tyrosine mutation at amino acid position 63 (C63Y) of SEQ ID No. 9.

58. The wheat plant of paragraph 55, wherein the mutations contribute to grain from said wheat plant having an altered seed storage protein profile in endosperm from said wheat plant.

59. The wheat plant of paragraph 55, further comprising a mutation in the WPBF gene in the A genome.

60. Wheat grain from the wheat plant of any of the preceding paragraphs and at least one glutenase enzyme.

61. Flour comprising the wheat grain of any of the preceding paragraphs and at least one glutenase enzyme.

62. A food product comprising a component of the wheat plant of any of the preceding paragraphs and at least one glutenase enzyme.

63. A wheat seed, plant part or progeny thereof from the wheat plant of any of the preceding paragraphs and at least one glutenase enzyme.

64. Grain from the barley plant of any of the preceding paragraphs and at least one glutenase enzyme.

65. Flour comprising the grain from the barley plant of any of the preceding paragraphs and at least one glutenase enzyme.

66. A food product comprising a component of the barley plant of any of the preceding paragraphs and at least one glutenase enzyme.

67. A barley seed, plant part or progeny thereof from the barley plant of any of the preceding paragraphs and at least one glutenase enzyme.

The following Examples are offered by way of illustration only, and not limitation. It is to be understood that the mutations discussed herein are merely exemplary and that similar mutations are also contemplated.

EXAMPLES

Example 1: Identification of Barley Transcript MLOC_12852.2

A reduced gluten barley plant was analyzed to identify the mutation corresponding to the reduced gluten phenotype. The low gluten barley gives an ELISA R5 antibody reading of 1,000 ppm gluten (mg/kg) as compared to wild type barley that has greater than 100,000 ppm gluten (mg/kg).

Figure 1B:
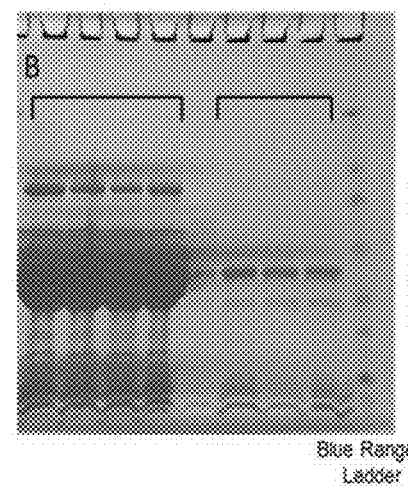

FIG. 1 is an SDS PAGE (sodium dodecyl sulphate Polyacrylamide gel Electrophoresis showing the presence or absence of the barley B, C, and D hordeins. As shown in FIG. 1A and FIGS. 1B, the B, C, and D hordeins are barely detectable in the low gluten barley.

Figure 2:
FIG. 2 is a photograph of wild type barley and mutant low gluten barley seeds.
Figure 3A:
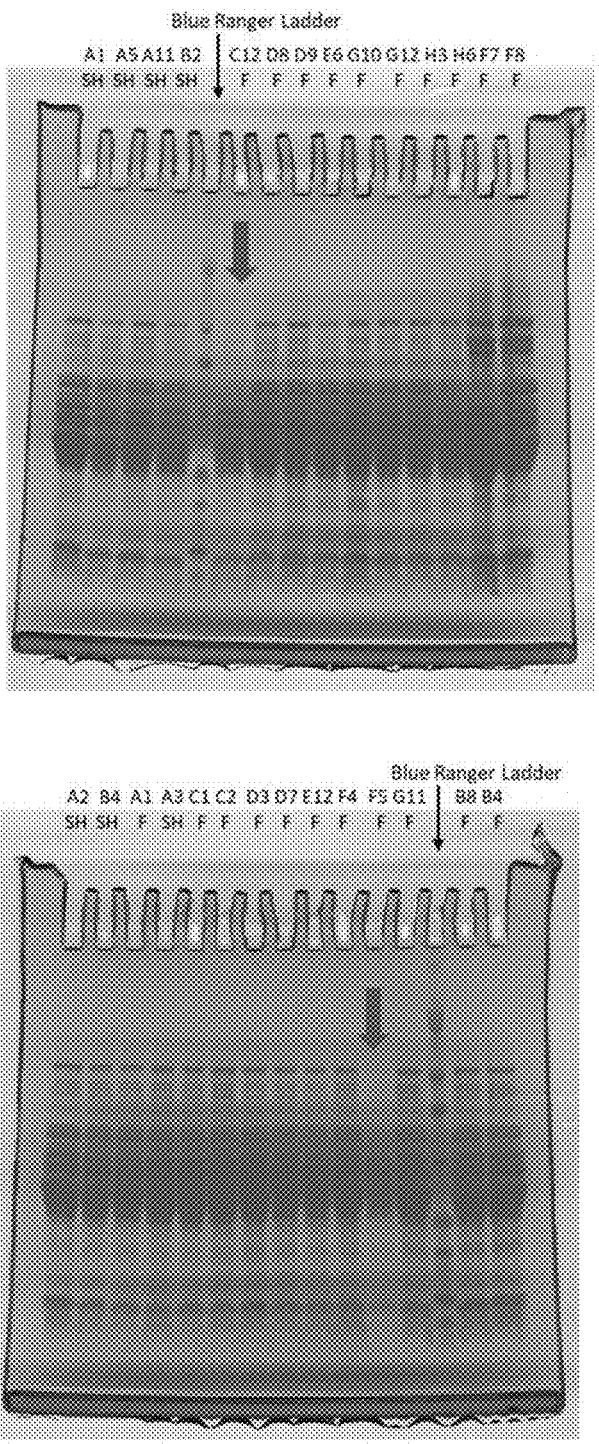
FIGS. 3A, 3B, 3C, and 3D depict digital scans of Coomassie blue stained SDS polyacrylamide gels. Each well represents alcohol-soluble grain storage proteins from the excised endosperm of a single wheat seed. Endosperm half-seeds that contain an altered seed storage protein profile with several protein bands missing and other proteins reduced in amount are indicated by arrows.
Figure 3B:
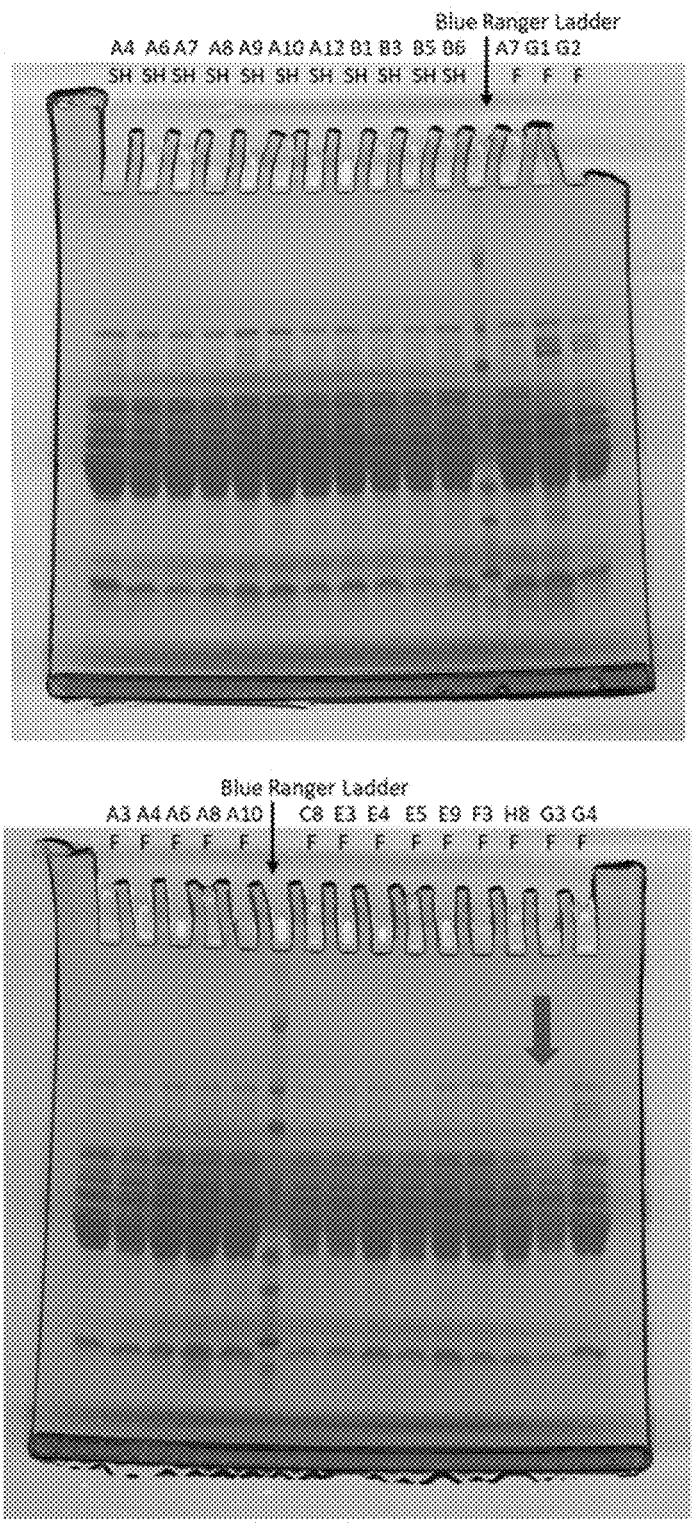
Figure 3C:
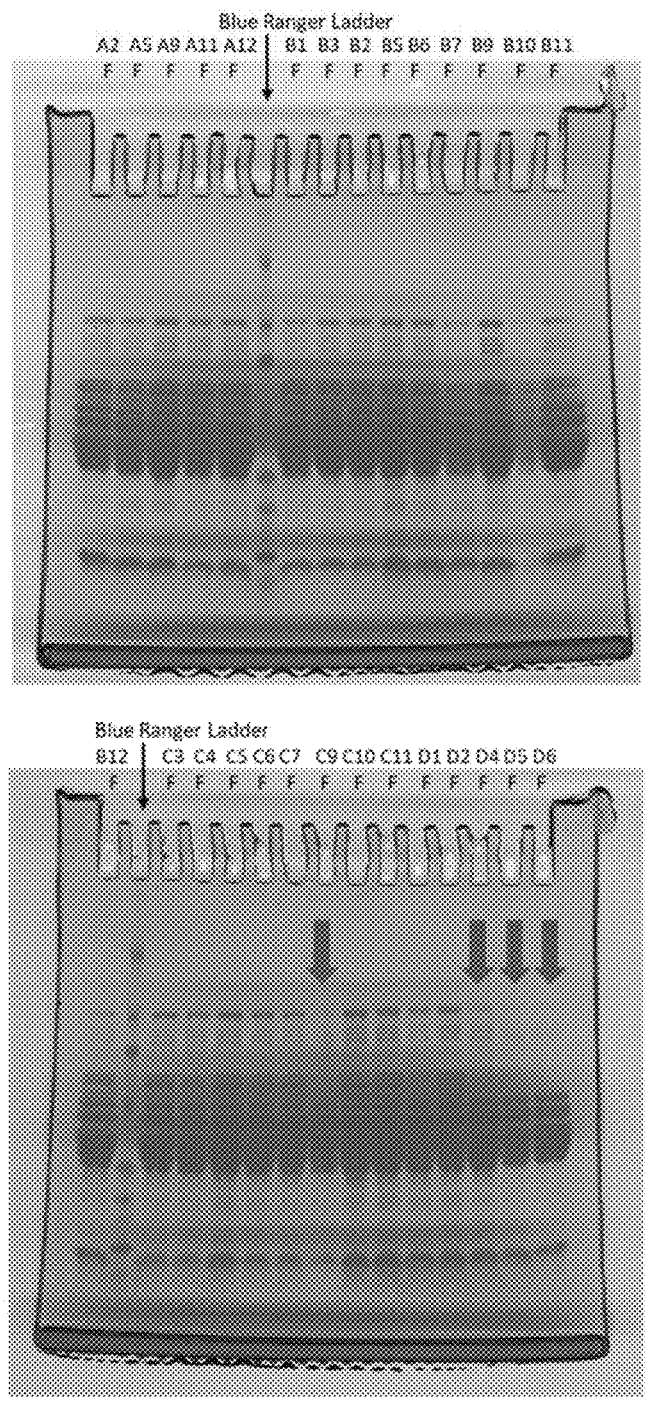
Figure 3D:
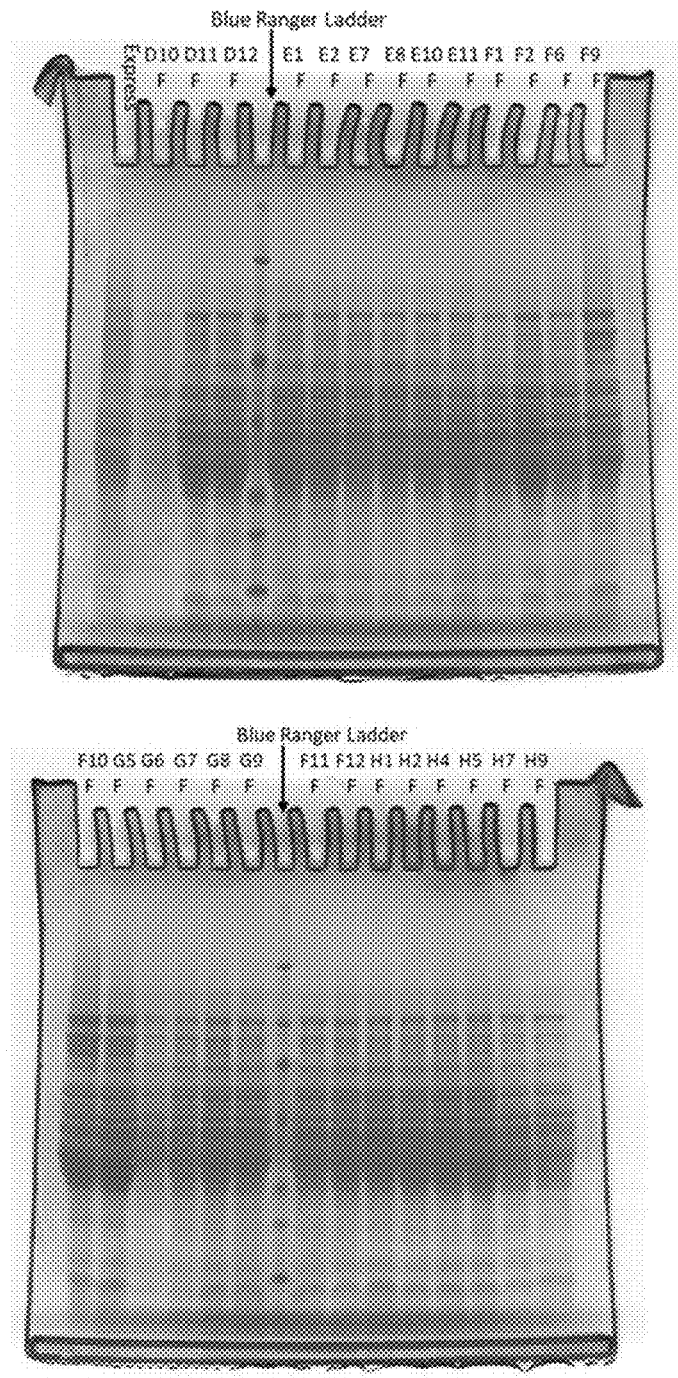

FIG. 2 is a photograph comparing the wild type barley seeds to the low gluten barley seeds, which are quite similar in physical characteristics and traits.

Bulked Segregant RNA sequencing approach was used to identify the gene corresponding to the phenotype of low gluten. A mapping population to identify the DNA SNPs in linkage with the mutation was created by crossing the mutant plant with an unrelated non-mutant barley cultivar (Bowman). F2 endosperm half-seeds were analyzed for hordein content to identify the homozygous mutant F2 segregants and the embryo half of both mutant and non-mutant seeds were grown to produce F3 seeds. In the F3, half-seed analysis was performed on about 20 non-mutant seed from each individual F2 to determine which F2 non-mutant half-seeds had been heterozygous for the single recessive mutation and which had been homozygous non-mutant. Between 20-40 individual F3 mutant seedlings, each from a different individual mutant F2, were grown and RNA was isolated in 3 replicated pools from ~7 day old whole etiolated seedlings, including both root and shoot tissue.

Likewise between 20-40 individual homozygous non-mutant seedlings, each from a different homozygous non-mutant F2 seed, were grown and RNA was isolated in three replicated pools from root and shoot tissue of whole ~7 day old etiolated homozygous non-mutant seedlings. RNA-seq analysis was conducted according to Liu et al Plos ONE 7(5): e36406 and SNPs were mapped to the barley genome.

SNPs co-segregating with the mutant localized the mutant to an approximately 4 cM region near the centromere on the long arm of chromosome 5H. Subsequently, KASP probes designed from selected SNPs were mapped in the larger mapping population and a 600 kb region in which SNPs showed no recombination with the mutant was identified. Examination of genes mapping near this region identified a mutation in barley transcript MLOC_12852.2, which is a Dof transcription factor. The coding sequence and amino acid sequence for barley transcript MLOC_12852.2 is show in SEQ ID NOS. 12, and 13 respectively. The low gluten barley plant contains a glutamine to a leucine change at position 58 of the amino acid sequence.

Example 2: Mutagenesis of Wheat Seeds

In accordance with one exemplary embodiment of the disclosure, wheat seeds of the hexaploid cultivar (*Triticum aestivum*) Express or tetraploid cultivar Kronos were vacuum infiltrated in H$_2$O (approximately 1,000 seeds/100 ml H$_2$O for approximately 4 minutes). The seeds were then placed on a shaker (45 rpm) in a fume hood at room temperature. The mutagen ethyl methanesulfonate (EMS) was added to the imbibing seeds to final concentrations ranging from about 0.75% to about 1.2% (v/v). Following an 18-hour incubation period, the EMS solution was replaced 4 times with fresh H$_2$O. The seeds were then rinsed under running water for about 4-8 hours. Finally, the mutagenized seeds were planted (96/tray) in potting soil and allowed to germinate indoors. Plants that were four to six weeks old were transferred to the field to grow to fully mature M1 plants. The mature M1 plants were allowed to self-pollinate and then seeds from the M1 plant were collected and planted to produce M2 plants.

DNA from the M2 plants produced in accordance with the above description was extracted and prepared in order to identify which M2 plants carried a mutation at one or more of their WPBF loci. The M2 plant DNA was prepared using the methods and reagents contained in the Qiagen® (Valencia, Calif.) DNeasy® 96 Plant Kit. Approximately 50 mg of frozen plant sample was placed in a sample tube with a tungsten bead, frozen in liquid nitrogen and ground 2 times for 1 minute each at 20 Hz using the Retsch® Mixer Mill MM 300. Next, 400 µl of solution AP1 [Buffer AP1, solution DX and RNAse (100 mg/ml)] at 80° C. was added to the sample. The tube was sealed and shaken for 15 seconds. Following the addition of 130 µl Buffer AP2, the tube was shaken for 15 seconds. The samples were placed in a freezer at minus 20° C. for at least 1 hour. The samples were then centrifuged for 20 minutes at 5,600×g. A 400 µl aliquot of supernatant was transferred to another sample tube. Following the addition of 600 µl of Buffer AP3/E, this sample tube was capped and shaken for 15 seconds. A filter plate was placed on a square well block and 1 ml of the sample solution was applied to each well and the plate was sealed. The plate and block were centrifuged for 4 minutes at 5,600×g. Next, 800 µl of Buffer AW was added to each well of the filter plate, sealed and spun for 15 minutes at 5,600×g in the square well block. The filter plate was then placed on a new set of sample tubes and 80 µl of Buffer AE was applied to the filter. It was capped and incubated at room temperature for 1 minute and then spun for 2 minutes at 5600×g. This step was repeated with an additional 80 µl Buffer AE. The filter plate was removed and the tubes containing the pooled filtrates were capped. The individual samples were then normalized to a DNA concentration of 5 to 10 ng/µl.

Tilling

The M2 wheat DNA was pooled into groups of two individual plants. The DNA concentration for each individual within the pool was approximately 2 ng/µl with a final concentration of 4 ng/µl for the entire pool. Then, 5 µl of the pooled DNA samples (or 20 ng wheat DNA) was arrayed on microtiter plates and subjected to gene-specific PCR.

PCR amplification was performed in 15 µl volumes containing 20 ng pooled DNA, 0.75×ExTaq buffer (Clonetech, Mountain View, Calif.), 1.1 mM additional $MgCl_2$, 0.3 mM dNTPs, 0.3 µM primers, 0.009 U Ex-Taq DNA polymerase (Clonetech, Mountain View, Calif.), 0.02 units DyNAzyme II DNA Polymerase (Thermo Scientific), and if necessary 0.33M Polymer-Aide PCR Enhancer (Sigma-Aldrich®). PCR amplification was performed using an MJ Research® thermal cycler as follows: 95° C. for 2 minutes; 8 cycles of "touchdown PCR" (94° C. for 20 second, followed by annealing step starting at 70-68° C. for 30 seconds and decreasing 1° C. per cycle, then a temperature ramp of 0.5° C. per second to 72° C. followed by 72° C. for 1 minute); 25-45 cycles of 94° C. for 20 seconds, 63 or 65° C. for 30 seconds, ramp 0.5° C./sec to 72° C., 72° C. for 1-2 minutes; 72° C. for 8 minutes; 98° C. for 8 minutes; 80° C. for 20 seconds; 60 cycles of 80° C. for 7 seconds-0.3 degrees/cycle.

PCR products (2-4 µl) were digested in 96-well plates. 3 µl of a solution containing 6 mM HEPES [4-(2-hydroxyethyl)-1-piperazineethanesulfonic acid] (pH 7.0), 6 mM $MgCl_2$, 6 mM NaCl, 0.012× Triton® X-100, 0.03 mg/ml of bovine serum albumin, 0.5× T-Digest Buffer [Advanced Analytical Technologies, Inc (AATI), Ames, Iowa], 0.912 U each of Surveyor® Endonuclease and Enhancer (Transgenomic®, Inc.), and 0.5× dsDNA Cleavage Enzyme (AATI, Ames, Iowa) was added to the PCR product. Digestion reactions were incubated at 45° C. for 45 minutes. The specific activity of the Surveyor enzyme was 800 units/µl, where a unit was defined by the manufacturer as the amount of enzyme required to produce 1 ng of acid-soluble material from sheared, heat denatured calf thymus DNA at pH 8.5 in one minute at 37° C. Reactions were stopped by addition of 20 µl of Dilution Buffer E (AATI, Ames, Iowa) or 1×TE. The reactions were stored in the freezer until they were run on the Fragment Analyzer™ (AATI, Ames, Iowa) Capillary Electrophoresis System. Samples were run on the Fragment Analyzer™ utilizing the DNF-920-K1000T Mutation Discovery Kit (AATI, Ames, Iowa) according to the manufacturer's protocol.

After electrophoresis, the assays were analyzed using PROSize® 2.0 Software (AATI, Ames, Iowa). The gel image showed sequence-specific pattern of background bands common to all 96 lanes. Rare events, such as mutations, create new bands that stand out above the background pattern. Plants with bands indicative of mutations of interest were evaluated by TILLING individual members of a pool mixed with wild type DNA and then sequencing individual PCR products. Plants carrying mutations confirmed by sequencing were grown up as described above (e.g., the M2 plant could be backcrossed or outcrossed multiple times in order to eliminate background mutations and self-pollinated in order to create a plant that was homozygous for the mutation) or crossed to another plant containing WPBF mutations in a different homoeolog.

In addition, grains from homozygous wheat plants with mutations in WPBF-A WPBF-B or WPBF-D of the A, B or D genomes were analyzed for seed storage protein content by extraction of prolamins from endosperm half-seeds. In addition, selected plants identified with severe mutations in WPBF of the A or B or D genomes (Tables 1, 2, and 3) were crossed with other plants that contained severe mutations in WPBF in the other genomes. Grains from homozygous plants resulting from these crosses were analyzed for accumulation of seed storage proteins. Severe mutations included those mutations that were predicted to have a deleterious effect on protein function by their SIFT and PSSM, as well as those mutations that resulted in the introduction of a stop codon (truncation mutation) or a mutation at a splice junction.

Example 3

Mutations in the WPBF Gene Result in Altered Seed Storage Protein Profiles in Wheat Seeds The technique of TILLING (targeting induced local lesions in genomes) was used to identify numerous mutations in the homologous transcription factor genes in wheat. These mutations have been identified in all of the homoeologous copies of the A and B genomes of tetraploid pasta wheat and all of the three homoeologous genomes of hexaploid bread wheat (A, B and D genomes).

To date, a mutation in the B genome of hexaploid bread wheat was crossed with a mutation in the D genome copy. The B genome mutation results in the alteration of a tryptophan codon into a stop codon at amino acid 70 (WPBF_B (W70*)), which may lead to a non-functional B genome copy of the gene. The D genome mutation alters cysteine at amino acid 63 into a tyrosine (WPBF_D(C63Y)), which, since the cysteine is responsible for coordinating a zinc ion in the active DNA-binding domain of the transcription factor, may also lead to a loss of function of the D genome copy of the gene.

In the F2 generation of the cross between parent plants harboring either one or the other of these mutations, ¹⁄₁₆ of the progeny are expected to be homozygous mutant at both B and D genome homoeologous copies of this gene. These progeny will have an un-mutated copy of the A genome copy of the gene, we wished to investigate alteration of the B and D genome copies of WPBF and any potential effect on the seed storage proteins of these seeds.

The experiment was carried out by cutting 111 individual F2 progeny seeds in half, saving the embryo half of the seed for planting, extracting the most abundant prolamin storage proteins from the endosperm half of the seed and electrophoresing these extracted proteins on SDS polyacrylamide gels (SDS-PAGE). As shown in FIGS. 3A-3D, 7 endosperm half-seeds (indicated by arrows) contain an altered seed storage protein profile with several protein bands missing and others apparently reduced in amount.

These results indicate that alteration of the B and D genomes of WPBF affects seed storage proteins. However, crossing a plant with an altered A genome copy of this gene to a plant with altered B and D genome copies of this gene is expected to produce larger effects on the seed storage protein profile of these plants.

The above results clearly indicate that a transcription factor in barley has been identified, which when mutated, results in drastic alterations in the seed storage protein profile of barley. Furthermore, mutations in the equivalent gene in wheat likewise lead to alterations in the storage proteins in wheat.

The above examples are provided to illustrate the invention but not limit its scope. Other variants of the invention will be readily apparent to one of ordinary skill in the art and are encompassed by the appended claims and all their equivalents. The examples above used TILLING technology to create and identify mutations in one or more WPBF genes of wheat but one of ordinary skill in the art would understand that other methods such as targeted mutagenesis (also known as site-directed mutagenesis, site-specific mutagenesis or oligonucleotide-directed mutagenesis) could be used to create the useful mutations of the present invention in one or more WPBF loci of wheat (see for example Zhang et al., *PNAS* 107(26):12028-12033, 2010; Saika et al., *Plant Physiology* 156:1269-1277, 2011). One of ordinary skill in the art would also recognize that additional methods could be used to inactivate or reduce the activity of the wheat WPBF genes. These methods include without limitation CRISPR/Cas9 mutagenesis, TALEN and zinc finger mutagenesis, RNAi, micro RNA and hairpin RNA based methods to mutate or reduce the accumulation of the WPBF transcripts. All publications, patents, and patent applications cited herein are hereby incorporated by reference.

What is claimed is:

1. Wheat grain comprising: a wheat prolamin box binding factor ("WPBF") gene with one or more non-transgenic human induced mutations encoding a WPBF protein comprising an amino acid sequence having 95% or greater identity to SEQ ID NO: 3 or having 95% or greater identity to SEQ ID NO: 6 or having 95% or greater identity to SEQ ID NO: 9, wherein the grain comprises an increase in lysine content as compared to grain from a wild type plant.

2. The wheat grain of claim 1, wherein the grain further comprises a reduced gluten content as compared to grain from a wild type plant.

3. The wheat grain of claim 1, wherein the increase in lysine content is at least 20% as compared to grain from a wild type wheat plant.

4. The wheat grain of claim 1, wherein the grain further comprises a reduction in gliadin content as compared to grain from a wild-type wheat plant.

5. The wheat grain of claim 4, wherein gliadin content is reduced at least 20% as compared to grain from a wild type wheat plant.

6. A method of altering glutenin content in a wheat plant comprising:
   (a) introducing at least one human induced mutations in a WPBF gene in plant material or plant parts from the wheat plant;
   (b) growing the plant material or plant parts to produce progeny wheat plants; and
   (c) selecting progeny wheat plants that produce wheat grain having one or more non-transgenic human induced alterations in the WPBF gene encoding a WPBF protein comprising an amino acid sequence having 95% or greater identity to SEQ ID NO: 3 or having 95% or greater identity to SEQ ID NO: 6 or having 95% or greater identity to SEQ ID NO: 9, wherein the grain comprises an increase in lysine content as compared to grain from a wild type plant.

7. The method of claim 6, wherein the WPBF gene comprises a nucleic acid sequence having 95% or greater identity to SEQ ID NO: 2.

8. The method of claim 6, wherein the WPBF gene comprises a nucleic acid sequence having 95% or greater identity to SEQ ID NO: 5.

9. The method of claim 6, wherein the WPBF gene comprises a nucleic acid sequence having 95% or greater identity to SEQ ID NO: 8.

10. The method of claim 6, wherein the grain further comprises a reduced gluten content as compared to grain from a wild type plant.

11. The method of claim 6, wherein the increase in lysine content is at least 20% as compared to grain from a wild type wheat plant.

12. The method of claim 6, wherein the grain further comprises a reduction in gliadin content as compared to grain from a wild-type wheat plant.

13. The method of claim 6, wherein gliadin content is reduced at least 20% as compared to grain from a wild type wheat plant.

14. The method of claim 6, further comprising harvesting the wheat grain from the selected progeny wheat plants.

15. The wheat grain of claim 1, wherein the WPBF protein encoded by the WPBF gene of the B genome has a tryptophan to a stop codon substitution at position 70 of SEQ ID NO. 6.

\* \* \* \* \*